US006858706B2

(12) United States Patent
Tuomanen et al.

(10) Patent No.: US 6,858,706 B2
(45) Date of Patent: Feb. 22, 2005

(54) POLYPEPTIDE COMPRISING THE AMINO ACID OF AN N-TERMINAL CHOLINE BINDING PROTEIN A TRUNCATE, VACCINE DERIVED THEREFROM AND USES THEREOF

(75) Inventors: Elaine I. Tuomanen, Germantown, TN (US); Theresa M. Wizemann, North Potamac, MD (US); H. Robert Masure, Germantown, TN (US); Leslie Sydnor Johnson, Germantown, MD (US); Scott Koenig, Rockville, MD (US)

(73) Assignees: St. Jude Children's Research Hospital, Memphis, TN (US); MedImmune, Inc., Gaithersburg, MD (US)

(*) Notice: Subject to any disclaimer, the term of this patent is extended or adjusted under 35 U.S.C. 154(b) by 0 days.

(21) Appl. No.: 09/056,019

(22) Filed: Apr. 7, 1998

(65) Prior Publication Data

US 2003/0096950 A1 May 22, 2003

(51) Int. Cl.[7] .................. A61K 38/00; A61K 39/09; A61K 39/38; A61K 39/02; A61K 39/00; C07K 16/00; C07K 17/00; C07K 7/00; C07K 5/00; C07K 1/00

(52) U.S. Cl. .............. 530/350; 530/324; 424/184.1; 424/185.1; 424/190.1; 424/244.1; 424/234.1

(58) Field of Search .................. 530/350, 324; 424/184.1, 185.1, 190.1, 244.1, 234.1

(56) References Cited

U.S. PATENT DOCUMENTS

| | | | |
|---|---|---|---|
| 4,925,673 A | 5/1990 | Steiner et al. | |
| 5,013,556 A | 5/1991 | Woodle et al. | |
| 5,284,656 A | 2/1994 | Platz et al. | |
| 5,451,569 A | 9/1995 | Wong et al. | |
| 6,245,335 B1 | 6/2001 | Masure et al. | |
| 6,291,654 B1 | 9/2001 | Hostetter et al. | |
| 6,420,135 B1 | 7/2002 | Kunsch et al. | |
| 6,500,613 B1 * | 12/2002 | Briles et al. ............. | 435/6 |
| 6,503,511 B1 | 1/2003 | Wizemann et al. | |
| 6,573,082 B1 * | 6/2003 | Choi et al. ............. | 435/252.3 |
| 6,689,369 B2 * | 2/2004 | Koenig et al. ............. | 424/244.1 |
| 6,784,164 B2 * | 8/2004 | Masure et al. ............. | 514/44 |
| 2002/0061545 A1 * | 5/2002 | Choi et al. ............. | 435/7.34 |
| 2003/0059438 A1 * | 3/2003 | Briles et al. ............. | 424/190.1 |
| 2003/0091577 A1 * | 5/2003 | Gilbert et al. ............. | 424/184.1 |
| 2003/0096950 A1 * | 5/2003 | Tuomanen et al. ............. | 530/350 |
| 2003/0138447 A1 * | 7/2003 | Wizemann et al. ............. | 424/190.1 |

FOREIGN PATENT DOCUMENTS

| | | |
|---|---|---|
| EP | 401384 | 3/1996 |
| WO | WO 97/09994 | 3/1997 |
| WO | WO 97/41151 | 11/1997 |
| WO | WO 98/18930 | 5/1998 |
| WO | WO 98/21337 | 5/1998 |
| WO | WO 99/51187 | 10/1999 |
| WO | WO 99/52166 | 10/1999 |

OTHER PUBLICATIONS

Tettelin et al, Science, 2001, 293:498–506.*
Brooks–Walker et al, Infection and Immunity, 1999, 67:6533–6542.*
Hoskins et al, J. Bacteriol, 2001, 183:5709–5717.*
Cheng et al, Biochemistry, 2000, 39:5450–5457.*
Iannelli et al, Gene, 2002, 284:63–71.*
Adjei et al., Pharma Res, 7:565–9.
Cundell et al., 1994, Micro Pathog, 17:361–74.
Cundell et al., 1995, Nature, 377:435–8
Hammerschmidit et al., 1997, Mol Microbiol, 25:1113–24.
Idanpaan–Heikkela I, et al., 1997, J Infect Dis, 176:704–12.
Langer, 1990, Science, 249:1527–33.
Malik et al., 1992, Exp Hematol, 20:1028–35.
McDaniel et al., 1992, Microb Pathog, 13:261–9.
Newmark et al., 1982, J Appl Biochem, 4:185–9.
Remington's Pharmaceutical Sciences, 18th ed., 1990, Mack Publishing Co., Easton, PA18042, Chapter 89.
Ronda et al., 1987, Eur J Biochem, 164:621–4.
Rosenow et al., 1997, Mol Microbiol, 25:819–1–29.
Shapiro et al., 1991, NJEM, 325:1453.
Tumanen et al., 1986, Rev Infect Dis, 8:Suppl 3:s279–91.
Tumanen et al., 1988, J Infect Dis, 158:36–43.
Tumanen et al., 1995, NEJM, 322:1280–4.
Wearly, 1991, Crit Rev in Ther Drug Carrier System, 8:333.

\* cited by examiner

*Primary Examiner*—N. M. Minnifield
(74) *Attorney, Agent, or Firm*—Alston & Bird LLP

(57) ABSTRACT

This invention provides an isolated polypeptide comprising an amino acid sequence of a N-terminal choline binding protein A truncate in which the amino acid sequence is set forth in any of SEQ ID NOS: 1, 3–7, or 9–11, including fragments, mutants, variants, analogs, or derivatives, thereof. Also, this invention provides a isolated polypeptide comprising an amino acid sequence of a N-terminal choline binding protein A truncate, wherein the amino acid is set forth in SEQ ID NO 24, wherein the polypeptide retains its native tertiary structure and methods of preparation. This invention provides an isolated polypeptide comprising an amino acid sequence of a N-terminal choline binding protein A truncate, wherein the polypeptide has lectin activity and does not bind to choline. This invention provides an isolated immunogenic polypeptide comprising an amino acid sequence of a N-terminal choline binding protein A truncate. This invention provides an isolated nucleic acid encoding a polypeptide comprising an amino acid sequence of a N-terminal choline binding protein A truncate. Lastly, this invention provides pharmaceutical compositions, vaccines, and diagnostic and therapeutic methods of use.

54 Claims, 11 Drawing Sheets

FIG. 2A-1

```
                                   10         20         30         40         50         60       70
SPB328(23F) CbpA       -AVASLVMGSVVHATENEVTTQVATSSNRANESQTEHRKAAKQ--------------------VDEYIKKML---Q--L  53
SPB365(23F) CbpA       -AVASLFMGSVVHATEKEVTTQVATSSNRANKSQTEHMKAAKQ--------------------VDEYIKKKL---Q--L  53
SPB105(6B)  CbpA       -AVASLFMGSVVHATEKEVTTQVATSSNRANKSQTEHMKAAKQ--------------------VDEYIKKKL---Q--L  53
SPSJ12(19A) CbpA       VAVASLVMGSVVHATEKEVTENEGTTQVATSSNRANESQAGHRKAAEQF--------------DEYIKTMI----Q--L  54
SPB331(14)  CbpA       -AVASLFMGSVVHATEKEVTTQVATSSNRANKSQTEHMKAAKQ--------------------DEYIEKML----Q--L  53
SPR332(9V)  CbpA       --VASLFMGSVVHATEKEVTENERTTQVPTSSNRGK---PERRKAAEQF--------------VDEYIKKKL---Q--L  52
ATCC2 CbpA trunc       CTVASLVMGSVVHATENEKTTQVPTYSNMAK---TEHRKAAKQV-------------------DEYINKMI----Q--L  51
R6X(2) CbpA trun       VAVASLVMGSVVHATENEKTTQVPTYSNMAK---TEHRKAAKQV-------------------VDEYIEKMLREIQ--L  55
SPSJ9(14) CbpA t       --------ENEGSTOAATSSNMAK---TEHRKAAKQV--------------------------VDEYIEKMLREIQ--L  40
ATCC6B CbpA trun       Y-IASLFLGGVVHAE----GVRSENNPTVTSSGQDISKKYADE--------------------VKSHLEKILSEIQTNL  54
Ntype4 CbpA trun       ---ASLFLGGVVHAE----GVRSGNNSTVTSSGQDISKKYADE--------------------VESHLQSILKDVNKNL  52
ATCC4 CbpA trunc       CIVASLVMGSVVHATENEGATQVPTSSNRANESQAEQGEQPKKLDSERDKARKEVEEYVKKIVGESYAKS          70
                       -IVASLVMGSVVHATENEGATQVPTSSNRANESQAEQGEQPKKLDSERDKARKEVEEYVKKIVGESYAKS          69

80         90        100        110        120        130       140
SPB328(23F) CbpA       DRRKHTQNVALNTKLSAIKTEYLHGLSVIKTEYLHGLSVSKKKSEAAELPSEIKA---KLDAAFEQFKKDTL--------  111
SPB365(23F) CbpA       DRRKHTQNVGLLTKLGVIKTEYLHGLSVIKTEYLHGLSVSKKKSEAELPSEIKA----KLDAAFEQFKKDTL--------  111
SPB105(6B)  CbpA       DRRKHTQNVGLLTKLGVIKTEYLHGLSVIKTEYLHGLSVSKKKSEAELPSEIKA----KLDAAFEQFKKDTL--------  113
SPSJ12(19A) CbpA       DRRKHTQNFALNIKLSRIKTEYLRKLNVLEEKSKELNVLEEKSKAELPSETKK-----EIDAAFEQFKKDTNR-------  111
SPB331(14)  CbpA       DRRKHTQNVGLLTKLGAIKTEYLRGLSVSKEKSTAELPSEIKE---------------KLTAAFKQFKKDTL--------  110
SPR332(9V)  CbpA       DRRKHTQNLAFNIQLSRIKTEYLNGL---KEKSEAELPSKIKA---KEKSEAELPSKIKA---ELDAAFQFKKDTL-----  106
ATCC2 CbpA trunc       DKRKHTQNLAFNMKLSAIKTEYLYGLK---EKSEAELPSEVKA---EKSEAELPSEVKA----KLDAAFEKFKKDTL----  110
R6X(2) CbpA trun       DRRKHTQNVALNIKLSAIKTYLRELNVLEEKSKDELPSEIKA--------------------KLDAAFEQFKKDTL-----  98
SPSJ9(14) CbpA t       DRSKHIKTVNLINKLQDIKRTYLYELNVLEDKSKAELPSKIKA---KEAELTSKTKETKEELTAAFEQFKKDTL-------  112
ATCC6B CbpA trun       KKVQHTQNADFNKKLSKIKTKYLYLELNVLEEKSEAELTSKTKETKEELTAAFEQFKKDTL-----------------  113
Ntype4 CbpA trun       TKKRHTQNVELNNIKNEYLN--KIVESTSESQLQILMMESRKVDEAVSKFEKDSSSSSQSSSTK-----------------  138
ATCC4 CbpA trunc       TKKRHTITVALVNELNNIKNEYLN--KIVESTSESQLQILMMESRKVDEAVSKFEKDSSSSSSSSDSSTK-----------  137
```

FIG. 2A-2

```
                                    150           160           170           180           190           200           210
                                    |             |             |             |             |             |             |
SPB328(23F) CbpA      ------------PTEPGKKVAEAEKKVEEAKKK--------AEDQKEEDKEKDLRNYPTNTYKTLELDIAESDVEV 162
SPB365(23F) CbpA      ------------PTEPGKKVAEAEKKVEEAKKK--------AEDQKEKDLRNYPTNTYKTLELDIAESDVEV 162
SPB105(6B) CbpA       ------------TK--KTVAEAEKKVEEAKKK--------AKAQKEEDHRNYPTNTYKTLELDIAESDVEV 161
SPSJ12(19A) CbpA      ------------KPEKKVAEAEKKVEEAKKK---------AEDQKEEDRRNYPTNTYKTLELEIAESDVEV 160
SPB331(14) CbpA       ------------PTEPGKKVAEAEKKVEEAKKK--------AEDQKEKDLRNYPTNTYKTLELDIAESDVEV 161
SPR332(9V) CbpA       ------------PTEPEKKVAEAEKKVEEAEKKVAEAKKKAKAQKEEDRRNYPTIYKTLDLEIAEFDVKV 164
ATCC2 CbpA trunc      ------------KLGEKVAEAEKKVAEAEKK---------AKAQKEEDRRNYPTNTYKTLELEIAESDVEV 159
R6X(2) CbpA trun      ------------KPGEKVAEAEKKKVEEAKKK--------AEDQKEEDYRNYPTNTYKTLELEIAEFDVKV 147
SPSJ9(14) CbpA t      ------------PTEPGKKVAEAEKKKKVEEAEKK-----AKAQKEEDYRNYPTIYKTLELEIAESDVKV 163
ATCC6B Cbpa trun      ------------STEPEKKVAEAEKKVEEAKKK--------AEDQKEEDRRNYPTIYKTLELEIAESDVEV 164
Ntype4 CbpA trun      PEASDTAKPNKPTEPGEKVAEAKKKVEEAEKK---------AKDQKEEDRRNYPTIYKTLELEIAESDVEV 201
ATCC4 CbpA trunc      PEASDTAKPNKPTEPGEKVAEAKKKVEEVEKK---------AKDQKEEDRRNYPTIYKTLELEIAESDVEV 200
```

FIG. 2B-1

```
                        ▢                                                                                            ▢
                       210                 220                230                240                250                260                270                280
                        |                   |                  |                  |                  |                  |                  |                  |
SPB328(23F)  CbpA   KKAELELVKEEAKESROEGKINOAKAKVESKKAEATRLKKIKTDREKAEEE-AKRRADAKLQEA---NVA  227
SPB365(23F)  CbpA   KKAELELVKEEAKESROEKKINOAKAKVENKKAEATRLKNIKTDREKAEE--AKRRADAKLQEA---NVA  227
SPB105(6B)   CbpA   KKAELELVKEEAKESRODEKKINOAKAKVENKKAEATRLKNIKTDREKAEE--AKRRADAKLQEA---NVA  230
SPSJ12(19A)  CbpA   KKAELELVKVKANEPRDEEKIKOAEAKVESKKAEATRLENIKTDREKAEEE-AKRRAEAKLKEAVEKNVA  224
SPB331(14)   CbpA   KKAELELVKEEAKESROEKKINOAKAKVENKKAEATRLKKIKTDREKAEEE--AKRRVDAKEQDE-----  226
SPR332(9V)   CbpA   KEAELELVKEEAKEADESRNEGTINOAKAKVESEKAEATRLKKIKTDREKAEEEEAKRRADAKLQEA--- 229
ATCC2  CbpA trunc   KKAELELVKEELLKEEAK-TRNEDTINOAKAKVESKKAEATKLEEIKTDRKKAEEE-AKRKAEAE-D--- 222
R6X(2) CbpA trun    KEAELELVKEEAKESRNEGTIKOAEKVESKAEATRLENIKTDREKAEEE-AKRKADAKLKEA---NVA    213
SPSJ9(14)  CbpA t   KEAELELVKEEADESRNEGTINOAKAKVESEQAEATRLKKIKTDREKAEEE-EAKRRADAKEQDE-----  227
ATCC6B Cbpa trun    KKAELELVKVKANEPRDEEKIKOAEATRLKKIKTDREQAEATRLENIKTDREQAEEEAKVK--------- 234
Ntype4 CbpA trun    KKAELELVKVKANEPROEOKIKOAEAKVESKQAEATRLKKIKTDREEAEEE-AKRRADAK---------- 261
ATCC4 CbpA trunc    KKAELELVKVKANEPRDKQKIKOAEAEVESKOAEATRLKKIKTDREEAEEE-AKRRADAK---------- 260

▯                                          ▯         ▯                      ▯
                           290                300               310                320                330                340                350
                            |                  |                 |                  |                  |                  |                  |
SPB328(23F)  CbpA   -SEQDKPKGRAKRGVPGELATPDKKENDAKSSDSSVGEETLPSPSLKPEKKVAEAEKKVEEAKKKAEDQK 297
SPB365(23F)  CbpA   TSEQDKSKRRAKREVXGELATPDKKENDAKSSDSSVGEETLTSPSLKPEKKVAEAEKKVEEAKKKAEDQK 297
SPB105(6B)   CbpA   TSEQDKSKRRAKREVLGELATPDKKENDAKSSDSSVGEETLTSPSLKPEKKVAEAEKKVEEAKKKAEDQK 300
SPSJ12(19A)  CbpA   TSEQDKPKGRRKRGVPGEQATPDKKENDAKSSDSSVGEEALPSPSLKPEKKVAEAEKKVEEAKKAKAQK  291
SPB331(14)   CbpA   -S-SKRRKSRXKRGDVGEOATPDKKENDAKSSDSSVGEETLPSPSLKPGKKVAEAEKKVEEADKKAKAQK 296
SPR332(9V)   CbpA   TSEQDKSKRRAKREVFGELATPDKKENDAKSSDSSVGEETLTSPSLKPEKKVAEAEKKVEEAKKKAEDQK 295
ATCC2  CbpA trunc   ---SKRRKSRGKRGALGEOATPDKKENDAKSSDSSVGEETLPSPSLKPGKKVAEAEKKVAEAEKKAKAQK 288
R6X(2) CbpA trun    ----DKLKRRTKRAVPGEATPDKKENDAKSSDSSVGEETLPSPSLKSGKKVAEAEKKVEEADKKAKAQK  283
SPSJ9(14)  CbpA t   TSDQGKPKGRAKRGVPGEATPDKKENDAKSSDSSVGEETLPSSSLKSGKKVAEAEKKVEEAEKKAKDQK  293
ATCC6B Cbpa trun    -S--KRRKSRVKRGDFGEPATPDKKENDAKSSDSSVGEETLPSPSLKPGKKVAEAEKKVEEAEKKAKDQK 300
Ntype4 CbpA trun    ----DEPKKRTKRGVLGEPATPDKKENDAKSSDSSVGEETLPSPSLKPEKKVAEAEKKVEEAKKKAEDQK 328
ATCC4 CbpA trunc    --EQGKPKGRAKRGVPGELATPDKKENDAKSSDSSVGEETLPSPSLKPEKKVAEAEKKVEEAKKKAEDQK 327
```

FIG. 2B-2

```
                  EEDRRNYPTNTYKTLELEIAESDVEVKKAELELVKEEAKESRNEEKVKQAKAEVESKKAEATRLEKIKTD
                          360       370       380       390       400       410       420
SPB328(23F)  CbpA      EEDRRNYPTNTYKTLELEIAESDVEVKKAELELVKEEAKESRNEEKIKQVKAKVESKKAEATRLENIKTD 367
SPB365(23F)  CbpA      EEDRRNYPTNTYKTLELEIAESDVEVKKAELELVKEEAKESRNEEKIKQVKAKVESKKAEATRLENIKTD 367
SPB105(6B)   CbpA      EEDRRNYPTNTYKTLELEIAESDVKVKEAELELVKEEAKESRNEEKVNQAKAKVESKKAEATRLEKIKTD 370
SPSJ12(19A)  CbpA      EEDRRNYPTNTYKTLELEIAESDVEVKKAELELVKEEAKEPRNEEKVKQAKAEVESKKAEATRLEKIKTD 361
SPB331(14)   CbpA      EEDRRNYPTNTYKTLELEIAESDVKVKEAELELVKEEAKESRNEEKIKQVKAKVESKKAEATRLENIKTD 366
SPR332(9V)   CbpA      EEDRRNYPTNTYKTLELEIAESDVKVKEAELELVKEEAKESRNEEKIKQAKAKVESKKAEATRLENIKTD 365
ATCC2 CbpA trunc      EEDRRNYPTNTYKTLDLEIAESDVEVKKAELELVKEEAKEPRDEEKIKQAKAKVESKKAEATRLENIKTD 358
R6X(2) CbpA trun      EEDRRNYPTNTYKTLTLOLEIAESDVEVKKAELELVKEEAKEAKGSRNEEKIKQAKAKVESKKAEATRLEKIKTD 353
SPSJ9(14) CbpA t      EEDHRNYPTITYKTLELEIAESDVEVKKAELELVKEEAKEAKGSRNEEKIKQAKAKVESKKAEATRLEKIKTD 363
ATCC6B Cbpa trun      EEDRRNYPTNTYKTLELEIAESDVEVKKAELELVKEEAKEPRNEEKVKQAKAEVESKQAEATRLEKIKTD 370
Ntype4 CbpA trun      EEDRRNYPTNTYKTLELEIAESDVEVKKAELELVKEEAKEPRNEEKVKQAKAEVESKKAEATRLEKIKTD 398
ATCC4 CbpA trunc      EEDRRNYPTNTYKTLELEIAESDVEVKKAELELVKEEAKEPRNEEKVKQAKAEVESKKAEATRLEKIKTD 397

RKKAEEE-AKRKAAEEDKVKEKPAEQPQPAPAPQPEKPAEEPENPAPAP-PKPENPAEQPKAEKPADQQA
                          430       440       450       460       470       480       490
SPB328(23F)  CbpA      RKKAEEEEAKRRAAEEEDKVKEKPAEQPQPAPAPQPEKPTEEPENPAPAPAPKPENPAEKPKAEKPADQQA 437
SPB365(23F)  CbpA      RKKAEEEEAKRRAAEEEDKVKEKPAEQPQPAPAPQPEKPTEEPENPAPAPAPKPENPAEKPKAEKPADQQA 437
SPB105(6B)   CbpA      RKKAEEE-AKRKAAEEEDKVKEKPAEQPQPAPAPQPEKPTEEPENPAPAPAPKPAEKPKAEKPADQQA 437
SPSJ12(19A)  CbpA      RKKAEEE-AKRKAAEEEDKVKEKPAEQPQPAPAPQPEKPTEEPENPAPAP--KPEKPAEQPKAEKPTDDQQA 419
SPB331(14)   CbpA      RKKAEEE-AKRKAAEEEDKVKEKPAEQPQPAPAPQPEKPAPAPQPEKPA-------P--KPENPAEQPKAEKPADQQA 436
SPR332(9V)   CbpA      RKKAEEE-AKRKAAEEEDKVKEKPAEQPQPAPAPQPEKPAPAPQPEKPAEEPENPAPAP--KPENPAEQPKAEKPADQQA 432
ATCC2 CbpA trunc      RKKAEEE-AKRKAAEEEDKVKEKPAEQPQPAPAPQPEKPAPAPQPEKPAEEPENPVPAP--PKPEKPAEQPKAEKTDDQQA 425
R6X(2) CbpA trun      RKKAEEE-AKRKAAEEEDKVKEKPAEQPQPAPAPQPEKPAPAPQPEKPTEEPENPAPA---A--PKPEKPAEQPKAEKPADQQA 411
SPSJ9(14) CbpA t      RKKAEEE-AKRKAAEEEDKVKEKPAEQPQPAPAPQPEKPATOPEKPAP---------A--PKPEKPAEQPKAEKPADQQA 423
ATCC6B Cbpa trun      RKKAEEE-AKRKAAEEEDKVKEKPAEQPQPAPAPQPEKPAPEKPAPA---PKPEKPAEQPKAEKPADQQA 437
Ntype4 CbpA trun      RKKAEEE-AKRKAAEEEDKVKEKPAEQPQPAPAPKAEKPA-------PAPKPENPAEQPKAEKPADQQA 458
ATCC4 CbpA trunc      RKKAEEE-AKRKAAEEEDKVKEKPAEQPQPAPAPKTEKPA-------PAPKPENPAEQPKAEKPADQQA 457
```

| | | |
|---|---|---|
| SPB328(23F) | CbpA | EE 439 |
| SPB365(23F) | CbpA | EE 437 |
| SPB105(6B) | CbpA | EE 439 |
| SPSJ12(19A) | CbpA | E 419 |
| SPB331(14) | CbpA | EE 437 |
| SPR332(9V) | CbpA | E 433 |
| ATCC2 | CbpA trunc | EE 427 |
| R6X(2) | CbpA trun | EE 413 |
| SPSJ9(14) | CbpA t | EE 425 |
| ATCC6B | Cbpa trun | EE 439 |
| Ntype4 | CbpA trun | EE 460 |
| ATCC4 | CbpA trunc | EE 459 |

FIG. 7

Active Protection

EPT: 4,096,000
Challenge: 560 cfu serotype 6B
n=10

- Sham
- CbpA truncate NR1X

SEQUENCE LISTING

<160> NUMBER OF SEQ ID NOS: 42

<210> SEQ ID NO 1
<211> LENGTH: 406
<212> TYPE: PRT
<213> ORGANISM: Streptococcus pneumoniae

<400> SEQUENCE: 1

Glu Asn Glu Gly Ala Thr Gln Val Pro Thr Ser Ser Asn Arg Ala Asn
 1               5                  10                  15

-continued

```
Glu Ser Gln Ala Glu Gln Gly Glu Gln Pro Lys Lys Leu Asp Ser Glu
             20                  25                  30
Arg Asp Lys Ala Arg Lys Glu Val Glu Glu Tyr Val Lys Lys Ile Val
             35                  40                  45
Gly Glu Ser Tyr Ala Lys Ser Thr Lys Lys Arg His Thr Ile Thr Val
             50                  55                  60
Ala Leu Val Asn Glu Leu Asn Asn Ile Lys Asn Glu Tyr Leu Asn Lys
 65                  70                  75                  80
Ile Val Glu Ser Thr Ser Glu Ser Gln Leu Gln Ile Leu Met Met Glu
                 85                  90                  95
Ser Arg Ser Lys Val Asp Glu Ala Val Ser Lys Phe Glu Lys Asp Ser
             100                 105                 110
Ser Ser Ser Ser Ser Ser Asp Ser Ser Thr Lys Pro Glu Ala Ser Asp
             115                 120                 125
Thr Ala Lys Pro Asn Lys Pro Thr Glu Pro Gly Glu Lys Val Ala Glu
 130                 135                 140
Ala Lys Lys Lys Val Glu Glu Ala Gly Lys Lys Ala Lys Asp Gln Lys
145                 150                 155                 160
Glu Glu Asp Arg Arg Asn Tyr Pro Thr Ile Thr Tyr Lys Thr Leu Glu
                 165                 170                 175
Leu Glu Ile Ala Glu Ser Asp Val Glu Val Lys Lys Ala Glu Leu Glu
             180                 185                 190
Leu Val Lys Val Lys Ala Asn Glu Pro Arg Asp Glu Gln Lys Ile Lys
             195                 200                 205
Gln Ala Glu Ala Glu Val Glu Ser Lys Gln Ala Glu Ala Thr Arg Leu
 210                 215                 220
Lys Lys Ile Lys Thr Asp Arg Glu Glu Ala Glu Glu Ala Lys Arg
225                 230                 235                 240
Arg Ala Asp Ala Lys Glu Gln Gly Lys Pro Lys Gly Arg Ala Lys Arg
                 245                 250                 255
Gly Val Pro Gly Glu Leu Ala Thr Pro Asp Lys Lys Glu Asn Asp Ala
             260                 265                 270
Lys Ser Ser Asp Ser Ser Val Gly Glu Glu Thr Leu Pro Ser Pro Ser
             275                 280                 285
Leu Lys Pro Glu Lys Lys Val Ala Glu Ala Lys Lys Val Glu Glu
 290                 295                 300
Ala Lys Lys Lys Ala Glu Asp Gln Lys Glu Glu Asp Arg Arg Asn Tyr
305                 310                 315                 320
Pro Thr Asn Thr Tyr Lys Thr Leu Glu Leu Glu Ile Ala Glu Ser Asp
                 325                 330                 335
Val Glu Val Lys Lys Ala Glu Leu Glu Leu Val Lys Glu Glu Ala Lys
             340                 345                 350
Glu Pro Arg Asn Glu Glu Lys Val Lys Gln Ala Lys Ala Glu Val Glu
             355                 360                 365
Ser Lys Lys Ala Glu Ala Thr Arg Leu Glu Lys Ile Lys Thr Asp Arg
 370                 375                 380
Lys Lys Ala Glu Glu Ala Lys Arg Lys Ala Glu Glu Asp Lys
385                 390                 395                 400
Val Lys Glu Lys Pro Ala
             405
```

<210> SEQ ID NO 2
<211> LENGTH: 655
<212> TYPE: PRT

<213> ORGANISM: Streptococcus pneumoniae

<400> SEQUENCE: 2

```
Glu Asn Glu Gly Ala Thr Gln Val Pro Thr Ser Ser Asn Arg Ala Asn
  1               5                  10                  15
Glu Ser Gln Ala Glu Gln Gly Glu Gln Pro Lys Lys Leu Asp Ser Glu
             20                  25                  30
Arg Asp Lys Ala Arg Lys Glu Val Glu Tyr Val Lys Lys Ile Val
         35                  40                  45
Gly Glu Ser Tyr Ala Lys Ser Thr Lys Arg His Thr Ile Thr Val
     50                  55                  60
Ala Leu Val Asn Glu Leu Asn Asn Ile Lys Asn Glu Tyr Leu Asn Lys
 65                  70                  75                  80
Ile Val Glu Ser Thr Ser Glu Ser Gln Leu Gln Ile Leu Met Met Glu
                 85                  90                  95
Ser Arg Ser Lys Val Asp Glu Ala Val Ser Lys Phe Glu Lys Asp Ser
            100                 105                 110
Ser Ser Ser Ser Ser Asp Ser Ser Thr Lys Pro Glu Ala Ser Asp
        115                 120                 125
Thr Ala Lys Pro Asn Lys Pro Thr Glu Pro Gly Glu Lys Val Ala Glu
    130                 135                 140
Ala Lys Lys Lys Val Glu Glu Ala Glu Lys Lys Ala Lys Asp Gln Lys
145                 150                 155                 160
Glu Glu Asp Arg Arg Asn Tyr Pro Thr Ile Thr Tyr Lys Thr Leu Glu
                165                 170                 175
Leu Glu Ile Ala Glu Ser Asp Val Glu Val Lys Lys Ala Glu Leu Glu
            180                 185                 190
Leu Val Lys Val Lys Ala Asn Glu Pro Arg Asp Glu Gln Lys Ile Lys
        195                 200                 205
Gln Ala Glu Ala Glu Val Glu Ser Lys Gln Ala Glu Ala Thr Arg Leu
    210                 215                 220
Lys Lys Ile Lys Thr Asp Arg Glu Glu Ala Glu Glu Ala Lys Arg
225                 230                 235                 240
Arg Ala Asp Ala Lys Glu Gln Gly Lys Pro Lys Gly Arg Ala Lys Arg
                245                 250                 255
Gly Val Pro Gly Glu Leu Ala Thr Pro Asp Lys Lys Glu Asn Asp Ala
            260                 265                 270
Lys Ser Ser Asp Ser Ser Val Gly Glu Glu Thr Leu Pro Ser Pro Ser
        275                 280                 285
Leu Lys Pro Glu Lys Lys Val Ala Glu Ala Glu Lys Lys Val Glu Glu
    290                 295                 300
Ala Lys Lys Lys Ala Glu Asp Gln Lys Glu Glu Asp Arg Arg Asn Tyr
305                 310                 315                 320
Pro Thr Asn Thr Tyr Lys Thr Leu Glu Leu Glu Ile Ala Glu Ser Asp
                325                 330                 335
Val Glu Val Lys Lys Ala Glu Leu Glu Leu Val Lys Glu Glu Ala Lys
            340                 345                 350
Glu Pro Arg Asn Glu Glu Lys Val Lys Gln Ala Lys Ala Glu Val Glu
        355                 360                 365
Ser Lys Lys Ala Glu Ala Thr Arg Leu Glu Lys Ile Lys Thr Asp Arg
    370                 375                 380
Lys Lys Ala Glu Glu Glu Ala Lys Arg Lys Ala Ala Glu Glu Asp Lys
385                 390                 395                 400
```

-continued

```
Val Lys Glu Lys Pro Ala Glu Pro Gln Pro Ala Pro Ala Pro Lys
            405                 410                 415

Ala Glu Lys Pro Ala Pro Ala Lys Pro Glu Asn Pro Ala Glu Gln
            420                 425                 430

Pro Lys Ala Glu Lys Pro Ala Asp Gln Gln Ala Glu Glu Asp Tyr Ala
            435                 440                 445

Arg Arg Ser Glu Glu Glu Tyr Asn Arg Leu Thr Gln Gln Pro Pro
    450                 455                 460

Lys Thr Glu Lys Pro Ala Gln Pro Ser Thr Pro Lys Thr Gly Trp Lys
465                 470                 475                 480

Gln Glu Asn Gly Met Trp Tyr Phe Tyr Asn Thr Asp Gly Ser Met Ala
                485                 490                 495

Thr Gly Trp Leu Gln Asn Asn Gly Ser Trp Tyr Tyr Leu Asn Ser Asn
                500                 505                 510

Gly Ala Met Ala Thr Gly Trp Leu Gln Asn Asn Gly Ser Trp Tyr Tyr
            515                 520                 525

Leu Asn Ala Asn Gly Ser Met Ala Thr Gly Trp Leu Gln Asn Asn Gly
530                 535                 540

Ser Trp Tyr Tyr Leu Asn Ala Asn Gly Ser Met Ala Thr Gly Trp Leu
545                 550                 555                 560

Gln Tyr Asn Gly Ser Trp Tyr Tyr Leu Asn Ala Asn Gly Ser Met Ala
                565                 570                 575

Thr Gly Trp Leu Gln Tyr Asn Gly Ser Trp Tyr Tyr Leu Asn Ala Asn
                580                 585                 590

Gly Asp Met Ala Thr Gly Trp Val Lys Asp Gly Asp Thr Trp Tyr Tyr
            595                 600                 605

Leu Glu Ala Ser Gly Ala Met Lys Ala Ser Gln Trp Phe Lys Val Ser
    610                 615                 620

Asp Lys Trp Tyr Tyr Val Asn Gly Ser Gly Ala Leu Ala Val Asn Thr
625                 630                 635                 640

Thr Val Asp Gly Tyr Gly Val Asn Ala Asn Gly Glu Trp Val Asn
                645                 650                 655

<210> SEQ ID NO 3
<211> LENGTH: 284
<212> TYPE: PRT
<213> ORGANISM: Streptococcus pneumoniae

<400> SEQUENCE: 3

Glu Asn Glu Gly Ala Thr Gln Val Pro Thr Ser Ser Asn Arg Ala Asn
 1               5                  10                  15

Glu Ser Gln Ala Glu Gln Gly Glu Gln Pro Lys Lys Leu Asp Ser Glu
                20                  25                  30

Arg Asp Lys Ala Arg Lys Glu Val Glu Glu Tyr Val Lys Lys Ile Val
            35                  40                  45

Gly Glu Ser Tyr Ala Lys Ser Thr Lys Lys Arg His Thr Ile Thr Val
        50                  55                  60

Ala Leu Val Asn Glu Leu Asn Asn Ile Lys Asn Glu Tyr Leu Asn Lys
65                  70                  75                  80

Ile Val Glu Ser Thr Ser Glu Ser Gln Leu Gln Ile Leu Met Met Glu
                85                  90                  95

Ser Arg Ser Lys Val Asp Glu Ala Val Ser Lys Phe Glu Lys Asp Ser
            100                 105                 110

Ser Ser Ser Ser Ser Ser Asp Ser Thr Lys Pro Glu Ala Ser Asp
        115                 120                 125
```

```
Thr Ala Lys Pro Asn Lys Pro Thr Glu Pro Gly Glu Lys Val Ala Glu
    130                 135                 140

Ala Lys Lys Lys Val Glu Glu Ala Glu Lys Lys Ala Lys Asp Gln Lys
145                 150                 155                 160

Glu Glu Asp Arg Arg Asn Tyr Pro Thr Ile Thr Tyr Lys Thr Leu Glu
                165                 170                 175

Leu Glu Ile Ala Glu Ser Asp Val Glu Val Lys Ala Glu Leu Glu
            180                 185                 190

Leu Val Lys Val Lys Ala Asn Glu Pro Arg Asp Glu Lys Ile Lys
            195                 200                 205

Gln Ala Glu Ala Glu Val Glu Ser Lys Gln Ala Glu Ala Thr Arg Leu
    210                 215                 220

Lys Lys Ile Lys Thr Asp Arg Glu Glu Ala Glu Glu Ala Lys Arg
225                 230                 235                 240

Arg Ala Asp Ala Lys Glu Gln Gly Lys Pro Lys Gly Arg Ala Lys Arg
                245                 250                 255

Gly Val Pro Gly Glu Leu Ala Thr Pro Asp Lys Lys Glu Asn Asp Ala
                260                 265                 270

Lys Ser Ser Asp Ser Ser Val Gly Glu Glu Thr Leu
    275                 280

<210> SEQ ID NO 4
<211> LENGTH: 106
<212> TYPE: PRT
<213> ORGANISM: Streptococcus pneumoniae

<400> SEQUENCE: 4

Lys Pro Glu Lys Lys Val Ala Glu Ala Glu Lys Val Glu Glu Ala
1               5                   10                  15

Lys Lys Lys Ala Glu Asp Gln Lys Glu Glu Asp Arg Arg Asn Tyr Pro
                20                  25                  30

Thr Asn Thr Tyr Lys Thr Leu Glu Leu Glu Ile Ala Glu Ser Asp Val
            35                  40                  45

Glu Val Lys Lys Ala Glu Leu Glu Leu Val Lys Glu Glu Ala Lys Glu
    50                  55                  60

Pro Arg Asn Glu Glu Lys Val Lys Gln Ala Lys Ala Glu Val Glu Ser
65                  70                  75                  80

Lys Lys Ala Glu Ala Thr Arg Leu Glu Lys Ile Lys Thr Asp Arg Lys
                85                  90                  95

Lys Ala Glu Glu Glu Ala Lys Arg Lys Ala
            100                 105

<210> SEQ ID NO 5
<211> LENGTH: 109
<212> TYPE: PRT
<213> ORGANISM: Streptococcus pneumoniae

<400> SEQUENCE: 5

Thr Glu Pro Gly Glu Lys Val Ala Glu Ala Lys Lys Val Glu Glu
1               5                   10                  15

Ala Glu Lys Lys Ala Lys Asp Gln Lys Glu Glu Asp Arg Arg Asn Tyr
                20                  25                  30

Pro Thr Ile Thr Tyr Lys Thr Leu Glu Leu Glu Ile Ala Glu Ser Asp
            35                  40                  45

Val Glu Val Lys Lys Ala Glu Leu Glu Leu Val Lys Val Lys Ala Asn
    50                  55                  60
```

```
Glu Pro Arg Asp Glu Gln Lys Ile Lys Gln Ala Glu Ala Val Glu
 65                  70                  75                  80

Ser Lys Gln Ala Glu Ala Thr Arg Leu Lys Lys Ile Lys Thr Asp Arg
                 85                  90                  95

Glu Glu Ala Glu Glu Ala Lys Arg Arg Ala Asp Ala
            100                 105
```

<210> SEQ ID NO 6
<211> LENGTH: 4
<212> TYPE: PRT
<213> ORGANISM: Streptococcus pneumoniae
<220> FEATURE:
<221> NAME/KEY: NON_CONS
<222> LOCATION: (2)..(3)
<223> OTHER INFORMATION: They could be any amino acid at these two
      locations.

<400> SEQUENCE: 6

```
Lys Xaa Xaa Glu
  1
```

<210> SEQ ID NO 7
<211> LENGTH: 376
<212> TYPE: PRT
<213> ORGANISM: Streptococcus pneumoniae

<400> SEQUENCE: 7

```
Glu Asn Glu Gly Ser Thr Gln Ala Ala Thr Ser Ser Asn Met Ala Lys
  1               5                  10                  15

Thr Glu His Arg Lys Ala Ala Lys Gln Val Val Asp Glu Tyr Ile Glu
                 20                  25                  30

Lys Met Leu Arg Glu Ile Gln Leu Asp Arg Arg Lys His Thr Gln Asn
             35                  40                  45

Val Ala Leu Asn Ile Lys Leu Ser Ala Ile Lys Thr Lys Tyr Leu Arg
     50                  55                  60

Glu Leu Asn Val Leu Glu Glu Lys Ser Lys Asp Glu Leu Pro Ser Glu
 65                  70                  75                  80

Ile Lys Ala Lys Leu Asp Ala Ala Phe Glu Lys Phe Lys Lys Asp Thr
                 85                  90                  95

Leu Lys Pro Gly Glu Lys Val Ala Glu Ala Lys Lys Val Glu Glu
            100                 105                 110

Ala Lys Lys Lys Ala Glu Asp Gln Lys Glu Glu Asp Arg Arg Asn Tyr
            115                 120                 125

Pro Thr Asn Thr Tyr Lys Thr Leu Glu Leu Glu Ile Ala Glu Phe Asp
            130                 135                 140

Val Lys Val Lys Glu Ala Leu Glu Leu Val Lys Glu Glu Ala Lys
145                 150                 155                 160

Glu Ser Arg Asn Glu Gly Thr Ile Lys Gln Ala Lys Glu Lys Val Glu
                165                 170                 175

Ser Lys Lys Ala Glu Ala Thr Arg Leu Glu Asn Ile Lys Thr Asp Arg
            180                 185                 190

Lys Lys Ala Glu Glu Ala Lys Arg Lys Ala Asp Ala Lys Leu Lys
            195                 200                 205

Glu Ala Asn Val Ala Thr Ser Asp Gln Gly Lys Pro Lys Gly Arg Ala
        210                 215                 220

Lys Arg Gly Val Pro Gly Glu Leu Ala Thr Pro Asp Lys Lys Glu Asn
225                 230                 235                 240
```

-continued

Asp Ala Lys Ser Ser Asp Ser Val Gly Glu Glu Thr Leu Pro Ser
                245                 250                 255

Ser Ser Leu Lys Ser Gly Lys Lys Val Ala Glu Ala Glu Lys Lys Val
            260                 265                 270

Glu Glu Ala Glu Lys Lys Ala Lys Asp Gln Lys Glu Glu Asp Arg Arg
        275                 280                 285

Asn Tyr Pro Thr Asn Thr Tyr Lys Thr Leu Asp Leu Glu Ile Ala Glu
    290                 295                 300

Ser Asp Val Lys Val Lys Glu Ala Glu Leu Glu Leu Val Lys Glu Glu
305                 310                 315                 320

Ala Lys Glu Pro Arg Asp Glu Glu Lys Ile Lys Gln Ala Lys Ala Lys
                325                 330                 335

Val Glu Ser Lys Lys Ala Glu Ala Thr Arg Leu Glu Asn Ile Lys Thr
            340                 345                 350

Asp Arg Lys Lys Ala Glu Glu Ala Lys Arg Lys Ala Ala Glu Glu
        355                 360                 365

Asp Lys Val Lys Glu Lys Pro Ala
    370                 375

<210> SEQ ID NO 8
<211> LENGTH: 663
<212> TYPE: PRT
<213> ORGANISM: Streptococcus pneumoniae

<400> SEQUENCE: 8

Glu Asn Glu Gly Ser Thr Gln Ala Ala Thr Ser Ser Asn Met Ala Lys
1               5                   10                  15

Thr Glu His Arg Lys Ala Ala Lys Gln Val Val Asp Glu Tyr Ile Glu
            20                  25                  30

Lys Met Leu Arg Glu Ile Gln Leu Asp Arg Arg Lys His Thr Gln Asn
        35                  40                  45

Val Ala Leu Asn Ile Lys Leu Ser Ala Ile Lys Thr Lys Tyr Leu Arg
    50                  55                  60

Glu Leu Asn Val Leu Glu Glu Lys Ser Lys Asp Glu Leu Pro Ser Glu
65                  70                  75                  80

Ile Lys Ala Lys Leu Asp Ala Ala Phe Glu Lys Phe Lys Lys Asp Thr
                85                  90                  95

Leu Lys Pro Gly Glu Lys Val Ala Glu Ala Lys Lys Val Glu Glu
            100                 105                 110

Ala Lys Lys Ala Glu Asp Gln Lys Glu Glu Asp Arg Arg Asn Tyr
        115                 120                 125

Pro Thr Asn Thr Tyr Lys Thr Leu Glu Leu Glu Ile Ala Glu Phe Asp
    130                 135                 140

Val Lys Val Lys Glu Ala Glu Leu Glu Leu Val Lys Glu Glu Ala Lys
145                 150                 155                 160

Glu Ser Arg Asn Glu Gly Thr Ile Lys Gln Ala Lys Glu Lys Val Glu
                165                 170                 175

Ser Lys Lys Ala Glu Ala Thr Arg Leu Glu Asn Ile Lys Thr Asp Arg
            180                 185                 190

Lys Lys Ala Glu Glu Ala Lys Arg Lys Ala Asp Ala Lys Leu Lys
        195                 200                 205

Glu Ala Asn Val Ala Thr Ser Asp Gln Gly Lys Pro Lys Gly Arg Ala
    210                 215                 220

Lys Arg Gly Val Pro Gly Glu Leu Ala Thr Pro Asp Lys Lys Glu Asn
225                 230                 235                 240

-continued

```
Asp Ala Lys Ser Ser Asp Ser Ser Val Gly Glu Glu Thr Leu Pro Ser
            245                 250                 255
Ser Ser Leu Lys Ser Gly Lys Lys Val Ala Glu Ala Glu Lys Lys Val
            260                 265                 270
Glu Glu Ala Glu Lys Ala Lys Asp Gln Lys Glu Asp Arg Arg
            275                 280                 285
Asn Tyr Pro Thr Asn Thr Tyr Lys Thr Leu Asp Leu Glu Ile Ala Glu
            290                 295                 300
Ser Asp Val Lys Val Lys Glu Ala Glu Leu Glu Leu Val Lys Glu Glu
305                 310                 315                 320
Ala Lys Glu Pro Arg Asp Glu Lys Ile Lys Gln Ala Lys Ala Lys
                325                 330                 335
Val Glu Ser Lys Lys Ala Glu Ala Thr Arg Leu Glu Asn Ile Lys Thr
            340                 345                 350
Asp Arg Lys Lys Ala Glu Glu Ala Lys Arg Lys Ala Ala Glu Glu
            355                 360                 365
Asp Lys Val Lys Glu Lys Pro Ala Glu Gln Pro Gln Pro Ala Pro Ala
370                 375                 380
Thr Gln Pro Glu Lys Pro Ala Pro Lys Pro Glu Lys Pro Ala Glu Gln
385                 390                 395                 400
Pro Lys Ala Glu Lys Thr Asp Asp Gln Gln Ala Glu Glu Asp Tyr Ala
                405                 410                 415
Arg Arg Ser Glu Glu Glu Tyr Asn Arg Leu Thr Gln Gln Pro Pro
            420                 425                 430
Lys Thr Glu Lys Pro Ala Gln Pro Ser Thr Pro Lys Thr Gly Trp Lys
            435                 440                 445
Gln Glu Asn Gly Met Trp Tyr Phe Tyr Asn Thr Asp Gly Ser Met Ala
            450                 455                 460
Thr Gly Trp Leu Gln Asn Asn Gly Ser Trp Tyr Tyr Leu Asn Ala Asn
465                 470                 475                 480
Gly Ala Met Ala Thr Gly Trp Leu Gln Asn Asn Gly Ser Trp Tyr Tyr
            485                 490                 495
Leu Asn Ala Asn Gly Ser Met Ala Thr Gly Trp Leu Gln Asn Asn Gly
            500                 505                 510
Ser Trp Tyr Tyr Leu Asn Ala Asn Gly Ala Met Ala Thr Gly Trp Leu
            515                 520                 525
Gln Tyr Asn Gly Ser Trp Tyr Tyr Leu Asn Ser Asn Gly Ala Met Ala
            530                 535                 540
Thr Gly Trp Leu Gln Tyr Asn Gly Ser Trp Tyr Tyr Leu Asn Ala Asn
545                 550                 555                 560
Gly Asp Met Ala Thr Gly Trp Leu Gln Asn Asn Gly Ser Trp Tyr Tyr
            565                 570                 575
Leu Asn Ala Asn Gly Asp Met Ala Thr Gly Trp Leu Gln Tyr Asn Gly
            580                 585                 590
Ser Trp Tyr Tyr Leu Asn Ala Asn Gly Asp Met Ala Thr Gly Trp Val
            595                 600                 605
Lys Asp Gly Asp Thr Trp Tyr Tyr Leu Glu Ala Ser Gly Ala Met Lys
            610                 615                 620
Ala Ser Gln Trp Phe Lys Val Ser Asp Lys Trp Tyr Tyr Val Asn Gly
625                 630                 635                 640
Ser Gly Ala Leu Ala Val Asn Thr Thr Val Asp Gly Tyr Gly Val Asn
            645                 650                 655
```

Ala Asn Gly Glu Trp Val Asn
            660

<210> SEQ ID NO 9
<211> LENGTH: 254
<212> TYPE: PRT
<213> ORGANISM: Streptococcus pneumoniae

<400> SEQUENCE: 9

Glu Asn Glu Gly Ser Thr Gln Ala Ala Thr Ser Ser Asn Met Ala Lys
 1               5                  10                  15

Thr Glu His Arg Lys Ala Ala Lys Gln Val Val Asp Glu Tyr Ile Glu
                20                  25                  30

Lys Met Leu Arg Glu Ile Gln Leu Asp Arg Arg Lys His Thr Gln Asn
            35                  40                  45

Val Ala Leu Asn Ile Lys Leu Ser Ala Ile Lys Thr Lys Tyr Leu Arg
    50                  55                  60

Glu Leu Asn Val Leu Glu Glu Lys Ser Lys Asp Glu Leu Pro Ser Glu
65                  70                  75                  80

Ile Lys Ala Lys Leu Asp Ala Ala Phe Glu Lys Phe Lys Lys Asp Thr
                85                  90                  95

Leu Lys Pro Gly Glu Lys Val Ala Glu Ala Lys Lys Val Glu Glu
            100                 105                 110

Ala Lys Lys Lys Ala Glu Asp Gln Lys Glu Glu Asp Arg Arg Asn Tyr
        115                 120                 125

Pro Thr Asn Thr Tyr Lys Thr Leu Glu Leu Glu Ile Ala Glu Phe Asp
    130                 135                 140

Val Lys Val Lys Glu Ala Glu Leu Glu Leu Val Lys Glu Glu Ala Lys
145                 150                 155                 160

Glu Ser Arg Asn Glu Gly Thr Ile Lys Gln Ala Lys Glu Lys Val Glu
                165                 170                 175

Ser Lys Lys Ala Glu Ala Thr Arg Leu Glu Asn Ile Lys Thr Asp Arg
            180                 185                 190

Lys Lys Ala Glu Glu Ala Lys Arg Lys Ala Asp Ala Lys Leu Lys
        195                 200                 205

Glu Ala Asn Val Ala Thr Ser Asp Gln Gly Lys Pro Lys Gly Arg Ala
    210                 215                 220

Lys Arg Gly Val Pro Gly Glu Leu Ala Thr Pro Asp Lys Lys Glu Asn
225                 230                 235                 240

Asp Ala Lys Ser Ser Asp Ser Ser Val Gly Glu Glu Thr Leu
                245                 250

<210> SEQ ID NO 10
<211> LENGTH: 106
<212> TYPE: PRT
<213> ORGANISM: Streptococcus pneumoniae

<400> SEQUENCE: 10

Lys Ser Gly Lys Lys Val Ala Glu Ala Glu Lys Lys Val Glu Glu Ala
 1               5                  10                  15

Glu Lys Lys Ala Lys Asp Gln Lys Glu Glu Asp Arg Arg Asn Tyr Pro
                20                  25                  30

Thr Asn Thr Tyr Lys Thr Leu Asp Leu Glu Ile Ala Glu Ser Asp Val
            35                  40                  45

Lys Val Lys Glu Ala Glu Leu Glu Leu Val Lys Glu Glu Ala Lys Glu
    50                  55                  60

```
Pro Arg Asp Glu Glu Lys Ile Lys Gln Ala Lys Ala Lys Val Glu Ser
 65                  70                  75                  80

Lys Lys Ala Glu Ala Thr Arg Leu Glu Asn Ile Lys Thr Asp Arg Lys
                 85                  90                  95

Lys Ala Glu Glu Glu Ala Lys Arg Lys Ala
            100                 105

<210> SEQ ID NO 11
<211> LENGTH: 107
<212> TYPE: PRT
<213> ORGANISM: Streptococcus pneumoniae

<400> SEQUENCE: 11

Pro Gly Glu Lys Val Ala Glu Ala Lys Lys Val Glu Ala Lys
  1               5                  10                  15

Lys Lys Ala Glu Asp Gln Lys Glu Glu Asp Arg Arg Asn Tyr Pro Thr
                 20                  25                  30

Asn Thr Tyr Lys Thr Leu Glu Leu Glu Ile Ala Glu Phe Asp Val Lys
             35                  40                  45

Val Lys Glu Ala Glu Leu Glu Leu Val Lys Glu Ala Lys Glu Ser
     50                  55                  60

Arg Asn Glu Gly Thr Ile Lys Gln Ala Lys Glu Lys Val Glu Ser Lys
 65                  70                  75                  80

Lys Ala Glu Ala Thr Arg Leu Glu Asn Ile Lys Thr Asp Arg Lys Lys
                 85                  90                  95

Ala Glu Glu Glu Ala Lys Arg Lys Ala Asp Ala
            100                 105

<210> SEQ ID NO 12
<211> LENGTH: 1219
<212> TYPE: DNA
<213> ORGANISM: Streptococcus pneumoniae

<400> SEQUENCE: 12
gagaacgagg gagctaccca agtaccccact tcttctaata gggcaaatga aagtcaggca        60
gaacaaggag aacaacctaa aaaactcgat tcagaacgag ataaggcaag gaaagaggtc       120
gaggaatatg taaaaaaaat agtgggtgag agctatgcaa aatcaactaa aaagcgacat       180
acaattactg tagctctagt taacgagttg aacaacatta gaacgagta tttgaataaa        240 atagttgaat caacctcaga aagccaacta cagatactga tgatggagag tcgatcaaaa       300
gtagatgaag ctgtgtctaa gtttgaaaag gactcatctt cttcgtcaag ttcagactct       360
tccactaaac cggaagcttc agatacagcg aagccaaaca agccgacaga accaggagaa       420
aaggtagcag aagctaagaa gaaggttgaa gaagctgaga aaaagccaa ggatcaaaaa        480 gaagaagatc gtcgtaacta cccaaccatt acttacaaaa cgcttgaact tgaaattgct       540
gagtccgatg tggaagttaa aaaagcggag cttgaactag taaagtgaa agctaacgaa        600 cctcgagacg agcaaaaaat taagcaagca gaagcggaag ttgagagtaa acaagctgag       660
gctacaaggt taaaaaaaat caagacagat cgtgaagaag cagaagaaga agctaaacga       720
agagcagatg ctaaagagca aggtaaacca aaggggcggg caaaacgagg agttcctgga       780
gagctagcaa cacctgataa aaaagaaaat gatgcgaagt cttcagattc tagcgtaggt       840
gaagaaactc ttccaagccc atccctgaaa ccagaaaaaa aggtagcaga agctgagaag       900
aaggttgaag aagctaagaa aaaagccgag gatcaaaaag aagaagatcg ccgtaactac       960
ccaaccaata cttacaaaac gcttgaactt gaaattgctg agtccgatgt ggaagttaaa      1020
```

```
aaagcggagc ttgaactagt aaagaggaa gctaaggaac ctcgaaacga ggaaaaagtt    1080
aagcaagcaa aagcggaagt tgagagtaaa aaagctgagg ctacaaggtt agaaaaaatc    1140
aagacagatc gtaaaaaagc agaagaagaa gctaaacgaa aagcagcaga agaagataaa    1200
gttaaagaaa aaccagctg                                                  1219

<210> SEQ ID NO 13
<211> LENGTH: 1969
<212> TYPE: DNA
<213> ORGANISM: Streptococcus pneumoniae

<400> SEQUENCE: 13
gagaacgagg gagctaccca agtacccact tcttctaata gggcaaatga aagtcaggca      60
gaacaaggag aacaacctaa aaaactcgat tcagaacgag ataaggcaag gaaagaggtc     120
gaggaatatg taaaaaaaat agtgggtgag agctatgcaa aatcaactaa aaagcgacat     180
acaattactg tagctctagt taacgagttg aacaacatta gaacgagta tttgaataaa      240 atagttgaat caacctcaga aagccaacta cagatactga tgatggagag tcgatcaaaa     300
gtagatgaag ctgtgtctaa gtttgaaaag gactcatctt cttcgtcaag ttcagactct     360
tccactaaac cggaagcttc agatacagcg aagccaaaca agccgacaga accaggagaa     420
aaggtagcag aagctaagaa gaaggttgaa gaagctgaga aaaaagccaa ggatcaaaaa     480
gaagaagatc gtcgtaacta cccaaccatt acttacaaaa cgcttgaact tgaaattgct     540
gagtccgatg tggaagttaa aaaagcggag cttgaactag taaaagtgaa agctaacgaa     600
cctcgagacg agcaaaaaat taagcaagca gaagcggaag ttgagagtaa acaagctgag     660
gctacaaggt taaaaaaaat caagacagat cgtgaagaag cagaagaaga agctaaacga     720
agagcagatg ctaaagagca aggtaaacca aaggggcggg caaaacgagg agttcctgga     780
gagctagcaa cacctgataa aaaagaaaat gatgcgaagt cttcagattc tagcgtaggt     840
gaagaaactc ttccaagccc atccctgaaa ccagaaaaaa aggtagcaga agctgagaag     900
aaggttgaag aagctaagaa aaaagccgag gatcaaaaag aagaagatcg ccgtaactac     960
ccaaccaata cttacaaaac gcttgaactt gaaattgctg agtccgatgt ggaagttaaa    1020
aaagcggagc ttgaactag taaaagagga agctaaggaa cctcgaaacg aggaaaaagt    1080
taagcaagca aaagcggaag ttgagagtaa aaaagctgag gctacaaggt agaaaaaat    1140 caagacagat cgtaaaaaag cagaagaaga agctaaacga aaagcagcag aagaagataa    1200
agttaaagaa aaaccagctg aacaaccaca accagcgccg gctccaaaag cagaaaaacc    1260
agctccagct ccaaaaccag agaatccagc tgaacaacca aaagcagaaa accagctga    1320 tcaacaagct gaagaagact atgctcgtag atcagaagaa gaatataatc gcttgactca    1380
acagcaaccg ccaaaaactg aaaaaccagc acaaccatct actccaaaaa caggctggaa    1440
acaagaaaac ggtatgtggt acttctacaa tactgatggt tcaatggcga caggatggct    1500
ccaaaacaat ggctcatggt actacctcaa cagcaatggc gctatggcga caggatggct    1560
ccaaaacaat ggttcatggt actatctaaa cgctaatggt tcaatggcaa caggatggct    1620
ccaaaacaat ggttcatggt actacctaaa cgctaatggt tcaatggcga caggatggct    1680
ccaatacaat ggctcatggt actacctaaa cgctaatggt tcaatggcga caggatggct    1740
ccaatacaat ggctcatggt actacctaaa cgctaatggt gatatggcga caggttgggt    1800
gaaagatgga gatacctggt actatcttga agcatcaggt gctatgaaag caagccaatg    1860
```

```
gttcaaagta tcagataaat ggtactatgt caatggctca ggtgcccttg cagtcaacac   1920
aactgtagat ggctatggag tcaatgccaa tggtgaatgg gtaaactaa               1969
```

<210> SEQ ID NO 14
<211> LENGTH: 853
<212> TYPE: DNA
<213> ORGANISM: Streptococcus pneumoniae

<400> SEQUENCE: 14

```
gagaacgagg gagctaccca agtacccact tcttctaata gggcaaatga aagtcaggca     60
gaacaaggag aacaacctaa aaactcgat tcagaacgag ataaggcaag gaaagaggtc    120
gaggaatatg taaaaaaaat agtgggtgag agctatgcaa aatcaactaa aaagcgacat    180
acaattactg tagctctagt taacgagttg aacaacatta gaacgagta tttgaataaa    240 atagttgaat caacctcaga aagccaacta cagatactga tgatggagag tcgatcaaaa    300
gtagatgaag ctgtgtctaa gtttgaaaag gactcatctt cttcgtcaag ttcagactct    360
tccactaaac cggaagcttc agatacagcg aagccaaaca agccgacaga accaggagaa    420
aaggtagcaa aagctaagaa gaaggttgaa gaagctgaga aaaagccaa ggatcaaaaa     480 gaagaagatc gtcgtaacta cccaaccatt acttacaaaa cgcttgaact tgaaattgct    540
gagtccgatg tggaagttaa aaaagcggag cttgaactag taaaagtgaa agctaacgaa    600
cctcgagacg agcaaaaaat taagcaagca gaagcggaag ttgagagtaa caagctgag    660 gctacaaggt taaaaaaaat caagacagat cgtgaagaag cagaagaaga agctaaacga    720
agagcagatg ctaaagagca aggtaaacca aagggcggg caaaacgagg agttcctgga    780
gagctagcaa cacctgataa aaaagaaaat gatgcgaagt cttcagattc tagcgtaggt    840
gaagaaactc ttc                                                       853
```

<210> SEQ ID NO 15
<211> LENGTH: 318
<212> TYPE: DNA
<213> ORGANISM: Streptococcus pneumoniae

<400> SEQUENCE: 15

```
aaaccagaaa aaaaggtagc agaagctgag aagaaggttg aagaagctaa gaaaaaagcc     60
gaggatcaaa aagaagaaga tcgccgtaac tacccaacca atacttacaa aacgcttgaa    120
cttgaaattg ctgagtccga tgtgaagtt aaaaaaagcgg agcttgaact agtaaaagag    180
gaagctaagg aacctcgaaa cgaggaaaaa gttaagcaag caaaagcgga agttgagagt    240 aaaaagctg aggctacaag gttagaaaaa atcaagacag atcgtaaaaa agcagaagaa    300
gaagctaaac gaaaagca                                                  318
```

<210> SEQ ID NO 16
<211> LENGTH: 327
<212> TYPE: DNA
<213> ORGANISM: Streptococcus pneumoniae

<400> SEQUENCE: 16

```
acagaaccag gagaaaaggt agcagaagct aagaagaagg ttgaagaagc tgagaaaaaa     60
gccaaggatc aaaagaaga agatcgtcgt aactacccaa ccattactta caaaacgctt    120
gaacttgaaa ttgctgagtc cgatgtggaa gttaaaaaag cggagcttga actagtaaaa    180
gtgaaagcta acgaacctcg agacgagcaa aaaattaagc aagcagaagc ggaagttgag    240
agtaaacaag ctgaggctac aaggttaaaa aaaatcaaga cagatcgtga agaagcagaa    300
```

```
gaagaagcta aacgaagagc agatgct                                  327

<210> SEQ ID NO 17
<211> LENGTH: 1129
<212> TYPE: DNA
<213> ORGANISM: Streptococcus pneumoniae

<400> SEQUENCE: 17
gaaaacgaag gaagtaccca agcagccact tcttctaata tggcaaagac agaacatagg   60
aaagctgcta acaagtcgt cgatgaatat atagaaaaaa tgttgaggga gattcaacta  120
gatagaagaa aacatacccca aaatgtcgcc ttaaacataa agttgagcgc aattaaaacg  180
aagtatttgc gtgaattaaa tgttttagaa gagaagtcga agatgagtt gccgtcagaa  240 ataaaagcaa agttagacgc agcttttgag aagtttaaaa agatacatt gaaaccagga  300 gaaaaggtag cagaagctaa gaagaaggtt gaagaagcta agaaaaaagc cgaggatcaa  360
aaagaagaag atcgtcgtaa ctacccaacc aatacttaca aaacgcttga acttgaaatt  420
gctgagttcg atgtgaaagt taagaagcg gagcttgaac tagtaaaaga ggaagctaaa  480
gaatctcgaa acgagggcac aattaagcaa gcaaaagaga agttgagag taaaaaagct  540 gaggctacaa ggttagaaaa catcaagaca gatcgtaaaa aagcagaaga agaagctaaa  600
cgaaaagcag atgctaagtt gaaggaagct aatgtagcga cttcagatca aggtaaacca  660
aaggggcggg caaaacgagg agttcctgga gagctagcaa cacctgataa aaagaaaaat  720
gatgcgaagt cttcagattc tagcgtaggt gaagaaactc ttccaagctc atccctgaaa  780
tcaggaaaaa aggtagcaga agctgagaag aaggttgaag aagctgagaa aaaagccaag  840
gatcaaaaag aagaagatcg ccgtaactac ccaaccaata cttacaaaac gcttgaccttt  900 gaaattgctg agtccgatgt gaaagttaaa gaagcggagc ttgaactagt aaaagaggaa  960
gctaaggaac ctcgagacga ggaaaaaatt aagcaagcaa aagcgaaagt tgagagtaaa 1020
aaagctgagg ctacaaggtt agaaaacatc aagacagatc gtaaaaaagc agaagaagaa 1080
gctaaacgaa aagcagcaga agaagataaa gttaaagaaa aaccagctg              1129

<210> SEQ ID NO 18
<211> LENGTH: 1992
<212> TYPE: DNA
<213> ORGANISM: Streptococcus pneumoniae

<400> SEQUENCE: 18
gaaaacgaag gaagtaccca agcagccact tcttctaata tggcaaagac agaacatagg   60
aaagctgcta acaagtcgt cgatgaatat atagaaaaaa tgttgaggga gattcaacta  120
gatagaagaa aacatacccca aaatgtcgcc ttaaacataa agttgagcgc aattaaaacg  180
aagtatttgc gtgaattaaa tgttttagaa gagaagtcga agatgagtt gccgtcagaa  240 ataaaagcaa agttagacgc agcttttgag aagtttaaaa agatacatt gaaaccagga  300 gaaaaggtag cagaagctaa gaagaaggtt gaagaagcta agaaaaaagc cgaggatcaa  360
aaagaagaag atcgtcgtaa ctacccaacc aatacttaca aaacgcttga acttgaaatt  420
gctgagttcg atgtgaaagt taagaagcg gagcttgaac tagtaaaaga ggaagctaaa  480
gaatctcgaa acgagggcac aattaagcaa gcaaaagaga agttgagag taaaaaagct  540 gaggctacaa ggttagaaaa catcaagaca gatcgtaaaa aagcagaaga agaagctaaa  600
cgaaaagcag atgctaagtt gaaggaagct aatgtagcga cttcagatca aggtaaacca  660
```

-continued

| | |
|---|---|
| aagggcggg caaaacgagg agttcctgga gagctagcaa cacctgataa aaaagaaaat | 720 |
| gatgcgaagt cttcagattc tagcgtaggt gaagaaactc ttccaagctc atccctgaaa | 780 |
| tcaggaaaaa aggtagcaga agctgagaag aaggttgaag aagctgagaa aaaagccaag | 840 |
| gatcaaaaag aagaagatcg ccgtaactac ccaaccaata cttacaaaac gcttgacctt | 900 |
| gaaattgctg agtccgatgt gaaagttaaa gaagcggagc ttgaactagt aaaagaggaa | 960 |
| gctaaggaac ctcgagacga ggaaaaaatt aagcaagcaa aagcgaaagt tgagagtaaa | 1020 |
| aaagctgagg ctacaaggtt agaaaacatc aagacagatc gtaaaaaagc agaagaagaa | 1080 |
| gctaaacgaa aagcagcaga agaagataaa gttaaagaaa accagctga acaaccacaa | 1140 |
| ccagcgccgg ctactcaacc agaaaaacca gctccaaaac cagagaagcc agctgaacaa | 1200 |
| ccaaaagcag aaaaaacaga tgatcaacaa gctgaagaag actatgctcg tagatcagaa | 1260 |
| gaagaatata atcgcttgac tcaacagcaa ccgccaaaaa ctgaaaaacc agcacaacca | 1320 |
| tctactccaa aaacaggctg gaaacaagaa acggtatgt ggtacttcta caatactgat | 1380 |
| ggttcaatgg caacaggatg gctccaaaac aacggttcat ggtactatct aaacgctaat | 1440 |
| ggtgctatgg cgacaggatg gctccaaaac aatggttcat ggtactatct aaacgctaat | 1500 |
| ggttcaatgg caacaggatg gctccaaaac aatggttcat ggtactacct aaacgctaat | 1560 |
| ggtgctatgg cgacaggatg gctccaatac aatggttcat ggtactacct aaacagcaat | 1620 |
| ggcgctatgg cgacaggatg gctccaatac aatggctcat ggtactacct caacgctaat | 1680 |
| ggtgatatgg cgacaggatg gctccaaaac aacggttcat ggtactacct caacgctaat | 1740 |
| ggtgatatgg cgacaggatg gctccaatac aacggttcat ggtattacct caacgctaat | 1800 |
| ggtgatatgg cgacaggttg ggtgaaagat ggagataacct ggtactatct tgaagcatca | 1860 |
| ggtgctatga aagcaagcca atggttcaaa gtatcagata atggtacta tgtcaatggc | 1920 |
| tcaggtgccc ttgcagtcaa cacaactgta gatggctatg gagtcaatgc caatggtgaa | 1980 |
| tgggtaaact aa | 1992 |

<210> SEQ ID NO 19
<211> LENGTH: 763
<212> TYPE: DNA
<213> ORGANISM: Streptococcus pneumoniae

<400> SEQUENCE: 19

| | |
|---|---|
| gaaaacgaag gaagtaccca agcagccact tcttctaata tggcaaagac agaacatagg | 60 |
| aaagctgcta acaagtcgt cgatgaatat atagaaaaaa tgttgaggga gattcaacta | 120 |
| gatagaagaa aacataccca aaatgtcgcc ttaaacataa agttgagcgc aattaaaacg | 180 |
| aagtatttgc gtgaattaaa tgttttagaa gagaagtcga aagatgagtt gccgtcagaa | 240 |
| ataaaagcaa agttagacgc agcttttgag aagtttaaaa agatacatt gaaaccagga | 300 |
| gaaaaggtag cagaagctaa gaagaaggtt gaagaagcta agaaaaaagc cgaggatcaa | 360 |
| aaagaagaag atcgtcgtaa ctacccaacc aatacttaca aaacgcttga acttgaaatt | 420 |
| gctgagttcg atgtgaaagt taagaagcg gagcttgaac tagtaaaaga ggaagctaaa | 480 |
| gaatctcgaa acgagggcac aattaagcaa gcaaaagaga agttgagag taaaaaagct | 540 |
| gaggctacaa ggttagaaaa catcaagaca gatcgtaaaa aagcagaaga agaagctaaa | 600 |
| cgaaaagcag atgctaagtt gaaggaagct aatgtagcga cttcagatca aggtaaacca | 660 |
| aagggcgggg caaaacgagg agttcctgga gagctagcaa cacctgataa aaaagaaaat | 720 |
| gatgcgaagt cttcagattc tagcgtaggt gaagaaactc ttc | 763 |

<210> SEQ ID NO 20
<211> LENGTH: 318
<212> TYPE: DNA
<213> ORGANISM: Streptococcus pneumoniae

<400> SEQUENCE: 20

```
aaatcaggaa aaaaggtagc agaagctgag aagaaggttg aagaagctga gaaaaaagcc       60
aaggatcaaa aagaagaaga tcgccgtaac tacccaacca atacttacaa aacgcttgac      120
cttgaaattg ctgagtccga tgtgaaagtt aaagaagcgg agcttgaact agtaaaagag      180
gaagctaagg aacctcgaga cgaggaaaaa attaagcaag caaaagcgaa agttgagagt      240
aaaaaagctg aggctacaag gttagaaaac atcaagacag atcgtaaaaa agcagaagaa      300
gaagctaaac gaaaagca                                                   318
```

<210> SEQ ID NO 21
<211> LENGTH: 321
<212> TYPE: DNA
<213> ORGANISM: Streptococcus pneumoniae

<400> SEQUENCE: 21

```
ccaggagaaa aggtagcaga agctaagaag aaggttgaag aagctaagaa aaaagccgag       60
gatcaaaaag aagaagatcg tcgtaactac ccaaccaata cttacaaaac gcttgaactt      120
gaaattgctg agttcgatgt gaaagttaaa gaagcggagc ttgaactagt aaaagaggaa      180 gctaagaat ctcgaaacga gggcacaatt aagcaagcaa agagaaagt tgagagtaaa       240 aaagctgagg ctacaaggtt agaaaacatc aagacagatc gtaaaaaagc agaagaagaa      300
gctaaacgaa aagcagatgc t                                               321
```

<210> SEQ ID NO 22
<211> LENGTH: 121
<212> TYPE: PRT
<213> ORGANISM: Streptococcus pneumoniae

<400> SEQUENCE: 22

```
Ser Pro Ser Leu Lys Pro Glu Lys Lys Val Ala Glu Ala Glu Lys Lys
  1               5                  10                  15

Val Glu Glu Ala Lys Lys Lys Ala Glu Asp Gln Lys Glu Glu Asp Arg
             20                  25                  30

Arg Asn Tyr Pro Thr Asn Thr Tyr Lys Thr Leu Glu Leu Glu Ile Ala
         35                  40                  45

Glu Ser Asp Val Glu Val Lys Lys Ala Glu Leu Glu Leu Val Lys Glu
     50                  55                  60

Glu Ala Lys Glu Pro Arg Asn Glu Glu Lys Val Lys Gln Ala Lys Ala
 65                  70                  75                  80

Glu Val Glu Ser Lys Lys Ala Glu Ala Thr Arg Leu Glu Lys Ile Lys
                 85                  90                  95

Thr Asp Arg Lys Lys Ala Glu Glu Ala Lys Arg Lys Ala Ala Glu
            100                 105                 110

Glu Asp Lys Val Lys Glu Lys Pro Ala
            115                 120
```

<210> SEQ ID NO 23
<211> LENGTH: 122
<212> TYPE: PRT
<213> ORGANISM: Streptococcus pneumoniae

```
<400> SEQUENCE: 23

Pro Ser Ser Ser Leu Lys Ser Gly Lys Lys Val Ala Glu Ala Glu Lys
  1               5                  10                  15

Lys Val Glu Glu Ala Glu Lys Lys Ala Lys Asp Gln Lys Glu Glu Asp
                 20                  25                  30

Arg Arg Asn Tyr Pro Thr Asn Thr Tyr Lys Thr Leu Asp Leu Glu Ile
             35                  40                  45

Ala Glu Ser Asp Val Lys Val Lys Glu Ala Glu Leu Glu Leu Val Lys
     50                  55                  60

Glu Glu Ala Lys Glu Pro Arg Asp Glu Lys Ile Lys Gln Ala Lys
 65                  70                  75                  80

Ala Lys Val Glu Ser Lys Lys Ala Glu Ala Thr Arg Leu Glu Asn Ile
                 85                  90                  95

Lys Thr Asp Arg Lys Lys Ala Glu Glu Ala Lys Arg Lys Ala Ala
                100                 105                 110

Glu Glu Asp Lys Val Lys Glu Lys Arg Ala
            115                 120

<210> SEQ ID NO 24
<211> LENGTH: 428
<212> TYPE: PRT
<213> ORGANISM: Streptococcus pneumoniae

<400> SEQUENCE: 24

Glu Asn Glu Gly Ala Thr Gln Val Pro Thr Ser Ser Asn Arg Ala Asn
  1               5                  10                  15

Glu Ser Gln Ala Glu Gln Gly Glu Gln Pro Lys Lys Leu Asp Ser Glu
                 20                  25                  30

Arg Asp Lys Ala Arg Lys Glu Val Glu Tyr Val Lys Lys Ile Val
             35                  40                  45

Gly Glu Ser Tyr Ala Lys Ser Thr Lys Lys Arg His Thr Ile Thr Val
     50                  55                  60

Ala Leu Val Asn Glu Leu Asn Asn Ile Lys Asn Glu Tyr Leu Asn Lys
 65                  70                  75                  80

Ile Val Glu Ser Thr Ser Glu Ser Gln Leu Gln Ile Leu Met Met Glu
                 85                  90                  95

Ser Arg Ser Lys Val Asp Glu Ala Val Ser Lys Phe Glu Lys Asp Ser
                100                 105                 110

Ser Ser Ser Ser Ser Asp Ser Ser Thr Lys Pro Glu Ala Ser Asp
            115                 120                 125

Thr Ala Lys Pro Asn Lys Pro Thr Glu Pro Gly Glu Lys Val Ala Glu
130                 135                 140

Ala Lys Lys Lys Val Glu Glu Ala Lys Lys Ala Lys Asp Gln Lys
145                 150                 155                 160

Glu Glu Asp Arg Arg Asn Tyr Pro Thr Ile Thr Tyr Lys Thr Leu Glu
                165                 170                 175

Leu Glu Ile Ala Glu Ser Asp Val Glu Val Lys Lys Ala Glu Leu Glu
            180                 185                 190

Leu Val Lys Val Lys Ala Asn Glu Pro Arg Asp Glu Gln Lys Ile Lys
        195                 200                 205

Gln Ala Glu Ala Glu Val Glu Ser Lys Gln Ala Glu Ala Thr Arg Leu
    210                 215                 220

Lys Lys Ile Lys Thr Asp Arg Glu Glu Ala Glu Glu Ala Lys Arg
225                 230                 235                 240
```

-continued

```
Arg Ala Asp Ala Lys Glu Gln Gly Lys Pro Lys Gly Arg Ala Lys Arg
            245                 250                 255
Gly Val Pro Gly Glu Leu Ala Thr Pro Asp Lys Lys Glu Asn Asp Ala
        260                 265                 270
Lys Ser Ser Asp Ser Ser Val Gly Glu Thr Leu Pro Ser Pro Ser
    275                 280                 285
Leu Lys Pro Glu Lys Lys Val Ala Glu Ala Lys Lys Val Glu Glu
    290                 295                 300
Ala Lys Lys Lys Ala Glu Asp Gln Lys Glu Glu Asp Arg Arg Asn Tyr
305                 310                 315                 320
Pro Thr Asn Thr Tyr Lys Thr Leu Glu Leu Glu Ile Ala Glu Ser Asp
                325                 330                 335
Val Glu Val Lys Lys Ala Glu Leu Glu Leu Val Lys Glu Glu Ala Lys
            340                 345                 350
Glu Pro Arg Asn Glu Glu Lys Val Lys Gln Ala Lys Ala Glu Val Glu
        355                 360                 365
Ser Lys Lys Ala Glu Ala Thr Arg Leu Glu Lys Ile Lys Thr Asp Arg
    370                 375                 380
Lys Lys Ala Glu Glu Ala Lys Arg Lys Ala Ala Glu Glu Asp Lys
385                 390                 395                 400
Val Lys Glu Lys Pro Ala Glu Gln Pro Gln Pro Ala Pro Ala Pro Lys
                405                 410                 415
Ala Glu Lys Pro Ala Pro Ala Pro Lys Pro Glu Asn
            420                 425

<210> SEQ ID NO 25
<211> LENGTH: 23
<212> TYPE: DNA
<213> ORGANISM: Streptococcus pneumoniae

<400> SEQUENCE: 25
ggcggatcca tggaraayga rgg                                           23

<210> SEQ ID NO 26
<211> LENGTH: 33
<212> TYPE: DNA
<213> ORGANISM: Streptococcus pneumoniae

<400> SEQUENCE: 26
gccgtcgact tagtttaccc attcaccatt ggc                                33

<210> SEQ ID NO 27
<211> LENGTH: 5
<212> TYPE: PRT
<213> ORGANISM: Streptococcus pneumoniae
<220> FEATURE:
<221> NAME/KEY: VARIANT
<222> LOCATION: (1)
<223> OTHER INFORMATION: It could be any amino acid.

<400> SEQUENCE: 27

Xaa Glu Asn Glu Gly
 1               5

<210> SEQ ID NO 28
<211> LENGTH: 439
<212> TYPE: PRT
<213> ORGANISM: Streptococcus pneumoniae
<220> FEATURE:
<221> NAME/KEY: VARIANT
<222> LOCATION: (243)
```

<223> OTHER INFORMATION: It could be any amino acid.

<400> SEQUENCE: 28

```
Ala Val Ala Ser Leu Phe Met Gly Ser Val His Ala Thr Glu Lys
  1               5                  10                  15

Glu Val Thr Thr Gln Val Ala Thr Ser Ser Asn Lys Ala Asn Lys Ser
                 20                  25                  30

Gln Thr Glu His Met Lys Ala Ala Lys Gln Val Asp Glu Tyr Ile Lys
             35                  40                  45

Lys Lys Leu Gln Leu Asp Arg Arg Lys His Thr Gln Asn Val Gly Leu
     50                  55                  60

Leu Thr Lys Leu Gly Val Ile Lys Thr Glu Tyr Leu His Gly Leu Ser
 65                  70                  75                  80

Val Ser Lys Lys Ser Glu Ala Glu Leu Pro Ser Glu Ile Lys Ala
                 85                  90                  95

Lys Leu Asp Ala Ala Phe Glu Gln Phe Lys Lys Asp Thr Leu Pro Thr
                100                 105                 110

Glu Pro Gly Lys Lys Val Ala Glu Ala Glu Lys Lys Val Glu Glu Ala
            115                 120                 125

Lys Lys Lys Ala Glu Asp Gln Lys Glu Lys Asp Leu Arg Asn Tyr Pro
130                 135                 140

Thr Asn Thr Tyr Lys Thr Leu Glu Leu Asp Ile Ala Glu Ser Asp Val
145                 150                 155                 160

Glu Val Lys Lys Ala Glu Leu Glu Leu Val Lys Glu Ala Lys Glu
                165                 170                 175

Ser Arg Asp Glu Lys Lys Ile Asn Gln Ala Lys Ala Lys Val Glu Asn
            180                 185                 190

Lys Lys Ala Glu Ala Thr Arg Leu Lys Asn Ile Lys Thr Asp Arg Glu
        195                 200                 205

Lys Ala Glu Glu Ala Lys Arg Arg Ala Asp Ala Lys Leu Gln Glu Ala
    210                 215                 220

Asn Val Ala Thr Ser Glu Gln Asp Lys Ser Arg Arg Ala Lys Arg
225                 230                 235                 240

Glu Val Xaa Gly Glu Leu Ala Thr Pro Asp Lys Lys Glu Asn Asp Ala
                245                 250                 255

Lys Ser Ser Asp Ser Ser Val Gly Glu Glu Thr Leu Thr Ser Pro Ser
            260                 265                 270

Leu Lys Pro Glu Lys Lys Val Ala Glu Ala Glu Lys Lys Val Glu Glu
        275                 280                 285

Ala Lys Lys Lys Ala Glu Asp Gln Lys Glu Glu Asp Arg Arg Asn Tyr
    290                 295                 300

Pro Thr Asn Thr Tyr Lys Thr Leu Glu Leu Glu Ile Ala Glu Ser Asp
305                 310                 315                 320

Val Glu Val Lys Lys Ala Glu Leu Glu Leu Val Lys Glu Glu Ala Lys
                325                 330                 335

Glu Ser Arg Asn Glu Glu Lys Ile Lys Gln Val Lys Ala Lys Val Glu
            340                 345                 350

Ser Lys Lys Ala Glu Ala Thr Arg Leu Glu Asn Ile Lys Thr Asp Arg
        355                 360                 365

Lys Lys Ala Glu Glu Glu Ala Lys Arg Arg Ala Ala Glu Glu Asp
    370                 375                 380

Lys Val Lys Glu Lys Pro Ala Glu Gln Pro Gln Pro Ala Pro Ala Pro
385                 390                 395                 400
```

```
Gln Pro Glu Lys Pro Thr Glu Pro Glu Asn Pro Ala Pro Ala Pro
                405                 410                 415

Ala Pro Lys Pro Glu Asn Pro Ala Glu Lys Pro Lys Ala Glu Lys Pro
            420                 425                 430

Ala Asp Gln Gln Ala Glu Glu
            435

<210> SEQ ID NO 29
<211> LENGTH: 437
<212> TYPE: PRT
<213> ORGANISM: Streptococcus pneumoniae

<400> SEQUENCE: 29

Ala Val Ala Ser Leu Phe Met Gly Ser Val His Ala Thr Glu Lys
 1               5                  10                  15

Glu Val Thr Thr Gln Val Ala Thr Ser Ser Asn Arg Ala Asn Lys Ser
                20                  25                  30

Gln Thr Glu His Met Lys Ala Ala Lys Gln Val Asp Glu Tyr Ile Lys
            35                  40                  45

Lys Lys Leu Gln Leu Asp Arg Arg Lys His Thr Gln Asn Val Gly Leu
    50                  55                  60

Leu Thr Lys Leu Gly Val Ile Lys Thr Glu Tyr Leu His Gly Leu Ser
65                  70                  75                  80

Val Ser Lys Lys Lys Ser Glu Ala Glu Leu Pro Ser Glu Ile Lys Ala
                85                  90                  95

Lys Leu Asp Ala Ala Phe Glu Gln Phe Lys Lys Asp Thr Leu Pro Thr
            100                 105                 110

Glu Pro Gly Lys Lys Val Ala Glu Ala Glu Lys Lys Val Glu Glu Ala
        115                 120                 125

Lys Lys Lys Ala Glu Asp Gln Lys Glu Lys Asp Leu Arg Asn Tyr Pro
    130                 135                 140

Thr Asn Thr Tyr Lys Thr Leu Glu Leu Asp Ile Ala Glu Ser Asp Val
145                 150                 155                 160

Glu Val Lys Lys Ala Glu Leu Glu Leu Val Lys Glu Glu Ala Lys Glu
                165                 170                 175

Ser Arg Asp Glu Lys Lys Ile Asn Gln Ala Lys Ala Lys Val Glu Asn
            180                 185                 190

Lys Lys Ala Glu Ala Thr Arg Leu Lys Asn Ile Lys Thr Asp Arg Glu
        195                 200                 205

Lys Ala Glu Glu Ala Lys Arg Arg Ala Asp Ala Lys Leu Gln Glu Ala
    210                 215                 220

Asn Val Ala Thr Ser Glu Gln Asp Lys Ser Lys Arg Arg Ala Lys Arg
225                 230                 235                 240

Glu Val Leu Gly Glu Leu Ala Thr Pro Asp Lys Lys Glu Asn Asp Ala
                245                 250                 255

Lys Ser Ser Asp Ser Ser Val Gly Glu Glu Thr Leu Thr Ser Pro Ser
            260                 265                 270

Leu Lys Pro Glu Lys Lys Val Ala Glu Ala Glu Lys Lys Val Glu Glu
        275                 280                 285

Ala Lys Lys Lys Ala Glu Asp Gln Lys Glu Glu Asp Arg Arg Asn Tyr
    290                 295                 300

Pro Thr Asn Thr Tyr Lys Thr Leu Glu Leu Glu Ile Ala Glu Ser Asp
305                 310                 315                 320

Val Glu Val Lys Lys Ala Glu Leu Glu Leu Val Lys Glu Glu Ala Lys
                325                 330                 335
```

```
Glu Ser Arg Asn Glu Glu Lys Ile Lys Gln Val Lys Ala Lys Val Glu
            340                 345                 350

Ser Lys Lys Ala Glu Ala Thr Arg Leu Glu Asn Ile Lys Thr Asp Arg
            355                 360                 365

Lys Lys Ala Glu Glu Glu Ala Lys Arg Arg Ala Ala Glu Glu Asp
            370                 375                 380

Lys Val Lys Glu Lys Pro Ala Glu Gln Pro Gln Pro Ala Pro Ala Pro
385                 390                 395                 400

Gln Pro Glu Lys Pro Thr Glu Glu Pro Glu Asn Pro Ala Pro Ala Pro
            405                 410                 415

Ala Pro Lys Pro Glu Asn Pro Ala Glu Lys Pro Lys Ala Glu Lys Pro
            420                 425                 430

Ala Asp Gln Gln Ala
            435

<210> SEQ ID NO 30
<211> LENGTH: 439
<212> TYPE: PRT
<213> ORGANISM: Streptococcus pneumoniae

<400> SEQUENCE: 30

Val Ala Val Ala Ser Leu Val Met Gly Ser Val Val His Ala Thr Glu
  1               5                  10                  15

Lys Glu Val Thr Thr Gln Val Ala Thr Ser Ser Asn Arg Ala Asn Glu
                 20                  25                  30

Ser Gln Ala Gly His Arg Lys Ala Ala Glu Gln Phe Asp Glu Tyr Ile
             35                  40                  45

Lys Thr Met Ile Gln Leu Asp Arg Arg Lys His Thr Gln Asn Phe Ala
         50                  55                  60

Leu Asn Ile Lys Leu Ser Arg Ile Lys Thr Glu Tyr Leu Arg Lys Leu
 65                  70                  75                  80

Asn Val Leu Glu Glu Lys Ser Lys Ala Glu Leu Pro Ser Glu Thr Lys
                 85                  90                  95

Lys Glu Ile Asp Ala Ala Phe Glu Gln Phe Lys Lys Asp Thr Asn Arg
            100                 105                 110

Thr Lys Lys Thr Val Ala Glu Ala Glu Lys Lys Val Glu Glu Ala Lys
            115                 120                 125

Lys Lys Ala Lys Ala Gln Lys Glu Glu Asp His Arg Asn Tyr Pro Thr
            130                 135                 140

Asn Thr Tyr Lys Thr Leu Glu Leu Glu Ile Ala Glu Ser Asp Val Glu
145                 150                 155                 160

Val Lys Lys Ala Glu Leu Glu Leu Val Lys Glu Glu Ala Lys Glu Ser
                165                 170                 175

Arg Asp Asp Glu Lys Ile Lys Gln Ala Glu Ala Lys Val Glu Ser Lys
            180                 185                 190

Lys Ala Glu Ala Thr Arg Leu Glu Asn Ile Lys Thr Asp Arg Glu Lys
            195                 200                 205

Ala Glu Glu Glu Ala Lys Arg Arg Ala Glu Ala Lys Leu Lys Glu Ala
            210                 215                 220

Val Glu Lys Asn Val Ala Thr Ser Glu Gln Asp Lys Pro Lys Gly Arg
225                 230                 235                 240

Arg Lys Arg Gly Val Pro Gly Glu Gln Ala Thr Pro Asp Lys Lys Glu
                245                 250                 255

Asn Asp Ala Lys Ser Ser Asp Ser Ser Val Gly Glu Glu Ala Leu Pro
```

-continued

```
                260                 265                 270
Ser Pro Ser Leu Lys Pro Glu Lys Val Ala Glu Ala Glu Lys Lys
            275                 280                 285
Val Ala Glu Ala Glu Lys Lys Ala Lys Ala Gln Lys Glu Glu Asp Arg
290                 295                 300
Arg Asn Tyr Pro Thr Asn Thr Tyr Lys Thr Leu Glu Leu Glu Ile Ala
305                 310                 315                 320
Glu Ser Asp Val Lys Val Lys Glu Ala Glu Leu Glu Leu Val Lys Glu
                325                 330                 335
Glu Ala Lys Glu Ser Arg Asn Glu Glu Lys Val Asn Gln Ala Lys Ala
            340                 345                 350
Lys Val Glu Ser Lys Lys Ala Glu Ala Thr Arg Leu Glu Lys Ile Lys
                355                 360                 365
Thr Asp Arg Lys Lys Ala Glu Glu Ala Lys Arg Lys Ala Ala Glu
            370                 375                 380
Glu Asp Lys Val Lys Glu Lys Pro Ala Glu Gln Pro Gln Pro Ala Pro
385                 390                 395                 400
Ala Pro Gln Pro Glu Lys Pro Thr Glu Glu Pro Glu Asn Pro Ala Pro
                405                 410                 415
Ala Pro Lys Pro Glu Lys Pro Ala Glu Gln Pro Lys Ala Glu Lys Thr
            420                 425                 430
Asp Asp Gln Gln Ala Glu Glu
            435

<210> SEQ ID NO 31
<211> LENGTH: 419
<212> TYPE: PRT
<213> ORGANISM: Streptococcus pneumoniae

<400> SEQUENCE: 31

Ala Val Ala Ser Leu Val Met Gly Ser Val Val His Ala Thr Glu Asn
1               5                   10                  15
Glu Gly Thr Thr Gln Ala Pro Thr Ser Ser Asn Arg Gly Asn Glu Ser
            20                  25                  30
Gln Ala Glu His Met Lys Ala Ala Lys Gln Val Asp Glu Tyr Ile Glu
        35                  40                  45
Lys Met Leu Gln Leu Asp Arg Arg Lys His Thr Gln Asn Val Gly Leu
    50                  55                  60
Leu Thr Lys Leu Gly Ala Ile Lys Thr Glu Tyr Leu Arg Gly Leu Ser
65                  70                  75                  80
Val Ser Lys Glu Lys Ser Thr Ala Glu Leu Pro Ser Glu Ile Lys Glu
                85                  90                  95
Lys Leu Thr Ala Ala Phe Lys Gln Phe Lys Lys Asp Thr Leu Lys Pro
            100                 105                 110
Glu Lys Lys Val Ala Glu Ala Glu Lys Lys Val Ala Glu Ala Lys Lys
        115                 120                 125
Lys Ala Glu Asp Gln Lys Glu Glu Asp Arg Arg Asn Tyr Pro Thr Ile
    130                 135                 140
Thr Tyr Lys Thr Leu Glu Leu Glu Ile Ala Glu Ser Asp Val Glu Val
145                 150                 155                 160
Lys Lys Ala Glu Leu Glu Leu Val Lys Val Lys Ala Asn Glu Pro Arg
                165                 170                 175
Asp Glu Glu Lys Ile Lys Gln Ala Glu Ala Glu Val Glu Ser Lys Lys
            180                 185                 190
```

```
Ala Glu Ala Thr Arg Leu Lys Lys Ile Lys Thr Asp Arg Glu Lys Ala
            195                 200                 205

Glu Glu Glu Ala Lys Arg Arg Val Asp Ala Lys Glu Gln Asp Glu Ser
        210                 215                 220

Ser Lys Arg Arg Lys Ser Arg Val Lys Arg Gly Asp Val Gly Glu Gln
225                 230                 235                 240

Ala Thr Pro Asp Lys Lys Glu Asn Asp Ala Lys Ser Ser Asp Ser Ser
                245                 250                 255

Val Gly Glu Glu Thr Leu Pro Ser Pro Ser Leu Lys Pro Gly Lys Lys
            260                 265                 270

Val Ala Glu Ala Glu Lys Lys Val Glu Ala Asp Lys Lys Ala Lys
        275                 280                 285

Ala Gln Lys Glu Glu Asp Arg Arg Asn Tyr Pro Thr Asn Thr Tyr Lys
        290                 295                 300

Thr Leu Glu Leu Glu Ile Ala Glu Ser Asp Val Glu Val Lys Lys Ala
305                 310                 315                 320

Glu Leu Glu Leu Val Lys Glu Ala Lys Glu Pro Arg Asn Glu Glu
                325                 330                 335

Lys Val Lys Gln Ala Lys Ala Glu Val Glu Ser Lys Lys Ala Glu Ala
            340                 345                 350

Thr Arg Leu Glu Lys Ile Lys Thr Asp Arg Lys Lys Ala Glu Glu Glu
            355                 360                 365

Ala Lys Arg Lys Ala Ala Glu Glu Asp Lys Val Lys Glu Lys Pro Ala
        370                 375                 380

Glu Gln Pro Lys Pro Ala Pro Ala Pro Gln Pro Glu Lys Pro Ala Pro
385                 390                 395                 400

Lys Pro Glu Asn Pro Ala Glu Gln Pro Lys Ala Glu Lys Pro Ala Asp
                405                 410                 415

Gln Gln Ala

<210> SEQ ID NO 32
<211> LENGTH: 437
<212> TYPE: PRT
<213> ORGANISM: Streptococcus pneumoniae

<400> SEQUENCE: 32

Val Ala Ser Leu Phe Met Gly Ser Val Val His Ala Thr Glu Lys Glu
  1               5                  10                  15

Val Thr Thr Gln Val Ala Thr Ser Ser Asn Lys Ala Asn Lys Ser Gln
            20                  25                  30

Thr Glu His Met Lys Ala Lys Gln Val Asp Glu Tyr Ile Lys Lys
            35                  40                  45

Lys Leu Gln Leu Asp Arg Arg Lys His Thr Gln Asn Val Gly Leu Leu
        50                  55                  60

Thr Lys Leu Gly Val Ile Lys Thr Glu Tyr Leu His Gly Leu Ser Val
 65                  70                  75                  80

Ser Lys Lys Lys Ser Glu Ala Glu Leu Pro Ser Glu Ile Lys Ala Lys
                85                  90                  95

Leu Asp Ala Ala Phe Glu Gln Phe Lys Lys Asp Thr Leu Pro Thr Glu
            100                 105                 110

Pro Gly Lys Lys Val Ala Glu Ala Glu Lys Lys Val Glu Glu Ala Lys
        115                 120                 125

Lys Lys Ala Glu Asp Gln Lys Glu Lys Asp Leu Arg Asn Tyr Pro Thr
    130                 135                 140
```

```
Asn Thr Tyr Lys Thr Leu Glu Leu Asp Ile Ala Glu Ser Asp Val Glu
145                 150                 155                 160

Val Lys Lys Ala Glu Leu Glu Leu Val Lys Glu Ala Lys Glu Ser
            165                 170                 175

Arg Asp Glu Lys Lys Ile Asn Gln Ala Lys Ala Lys Val Glu Asn Lys
            180                 185                 190

Lys Ala Glu Ala Thr Arg Leu Lys Asn Ile Lys Thr Asp Arg Glu Lys
        195                 200                 205

Ala Glu Glu Ala Lys Arg Arg Ala Asp Ala Lys Leu Gln Glu Ala Asn
        210                 215                 220

Val Ala Thr Ser Glu Gln Asp Lys Ser Lys Arg Arg Ala Lys Arg Glu
225                 230                 235                 240

Val Phe Gly Glu Leu Ala Thr Pro Asp Lys Lys Glu Asn Asp Ala Lys
                245                 250                 255

Ser Ser Asp Ser Ser Val Gly Glu Glu Thr Leu Thr Ser Pro Ser Leu
                260                 265                 270

Lys Pro Glu Lys Lys Val Ala Glu Ala Glu Lys Lys Val Glu Glu Ala
        275                 280                 285

Lys Lys Lys Ala Glu Asp Gln Lys Glu Glu Asp Arg Arg Asn Tyr Pro
        290                 295                 300

Thr Asn Thr Tyr Lys Thr Leu Glu Leu Glu Ile Ala Glu Ser Asp Val
305                 310                 315                 320

Glu Val Lys Lys Ala Glu Leu Glu Leu Val Lys Glu Ala Lys Glu
                325                 330                 335

Ser Arg Asn Glu Glu Lys Ile Lys Gln Val Lys Ala Lys Val Glu Ser
                340                 345                 350

Lys Lys Ala Glu Ala Thr Arg Leu Glu Asn Ile Lys Thr Asp Arg Lys
        355                 360                 365

Lys Ala Glu Glu Glu Ala Lys Arg Arg Ala Ala Glu Glu Asp Lys
        370                 375                 380

Val Lys Glu Lys Pro Ala Glu Gln Pro Gln Pro Ala Pro Ala Pro Gln
385                 390                 395                 400

Pro Glu Lys Pro Thr Glu Glu Pro Glu Asn Pro Ala Pro Ala Pro Ala
                405                 410                 415

Pro Lys Pro Glu Asn Pro Ala Glu Lys Pro Lys Ala Glu Lys Pro Ala
                420                 425                 430

Asp Gln Gln Ala Glu
        435

<210> SEQ ID NO 33
<211> LENGTH: 433
<212> TYPE: PRT
<213> ORGANISM: Streptococcus pneumoniae

<400> SEQUENCE: 33

Cys Thr Val Ala Ser Leu Val Met Gly Ser Val Val His Ala Thr Glu
1               5                   10                  15

Asn Glu Arg Thr Thr Gln Val Pro Thr Ser Ser Asn Arg Gly Lys Pro
                20                  25                  30

Glu Arg Arg Lys Ala Ala Glu Gln Phe Asp Glu Tyr Ile Asn Lys Met
            35                  40                  45

Ile Gln Leu Asp Lys Arg Lys His Thr Gln Asn Leu Ala Phe Asn Ile
        50                  55                  60

Gln Leu Ser Arg Ile Lys Thr Glu Tyr Leu Asn Gly Leu Lys Glu Lys
65                  70                  75                  80
```

```
Ser Glu Ala Glu Leu Pro Ser Lys Ile Lys Ala Glu Leu Asp Ala Ala
            85                  90                  95

Phe Lys Gln Phe Lys Lys Asp Thr Leu Pro Thr Glu Pro Glu Lys Lys
        100                 105                 110

Val Ala Glu Ala Glu Lys Lys Val Glu Glu Ala Glu Lys Lys Val Ala
        115                 120                 125

Glu Ala Lys Lys Ala Lys Ala Gln Lys Glu Glu Asp His Arg Asn
    130                 135                 140

Tyr Pro Thr Ile Thr Tyr Lys Thr Leu Asp Leu Glu Ile Ala Glu Phe
145                 150                 155                 160

Asp Val Lys Val Lys Glu Ala Glu Leu Glu Leu Val Lys Lys Glu Ala
                165                 170                 175

Asp Glu Ser Arg Asn Glu Gly Thr Ile Asn Gln Ala Lys Ala Lys Val
                180                 185                 190

Glu Ser Glu Lys Ala Glu Ala Thr Arg Leu Lys Lys Ile Lys Thr Asp
    195                 200                 205

Arg Glu Lys Ala Glu Glu Glu Ala Lys Arg Arg Ala Asp Ala Lys
    210                 215                 220

Glu Gln Asp Glu Ser Lys Arg Arg Lys Ser Arg Gly Lys Arg Gly Ala
225                 230                 235                 240

Leu Gly Glu Gln Ala Thr Pro Asp Lys Lys Glu Asn Asp Ala Lys Ser
                245                 250                 255

Ser Asp Ser Ser Val Gly Glu Glu Thr Leu Pro Ser Pro Ser Leu Lys
                260                 265                 270

Pro Gly Lys Lys Val Ala Glu Ala Lys Lys Val Glu Glu Ala Asp
                275                 280                 285

Lys Lys Ala Lys Ala Gln Lys Glu Glu Asp Arg Arg Asn Tyr Pro Thr
    290                 295                 300

Asn Thr Tyr Lys Thr Leu Glu Leu Glu Ile Ala Glu Ser Asp Val Lys
305                 310                 315                 320

Val Lys Glu Ala Glu Leu Glu Leu Val Lys Glu Ala Lys Glu Ser
                325                 330                 335

Arg Asn Glu Glu Lys Ile Lys Gln Ala Lys Ala Lys Val Glu Ser Lys
                340                 345                 350

Lys Ala Glu Ala Thr Arg Leu Glu Lys Ile Lys Thr Asp Arg Lys Lys
        355                 360                 365

Ala Glu Glu Ala Lys Arg Lys Ala Ala Glu Glu Asp Lys Val Lys
    370                 375                 380

Glu Lys Pro Ala Glu Gln Pro Gln Pro Ala Pro Ala Pro Gln Pro Glu
385                 390                 395                 400

Lys Pro Ala Glu Pro Glu Asn Pro Val Pro Ala Pro Lys Pro Glu
                405                 410                 415

Asn Pro Ala Glu Gln Pro Lys Ala Glu Lys Pro Ala Asp Gln Gln Ala
                420                 425                 430

Glu

<210> SEQ ID NO 34
<211> LENGTH: 427
<212> TYPE: PRT
<213> ORGANISM: Streptococcus pneumoniae

<400> SEQUENCE: 34

Val Ala Val Ala Ser Leu Val Met Gly Ser Val Val His Ala Thr Glu
 1               5                  10                  15
```

-continued

Lys Glu Val Thr Thr Gln Val Pro Thr Tyr Ser Asn Met Ala Lys Thr
            20                  25                  30

Glu His Arg Lys Ala Ala Lys Gln Val Val Asp Glu Tyr Ile Glu Lys
        35                  40                  45

Met Leu Arg Glu Ile Gln Leu Asp Arg Arg Lys His Thr Gln Asn Phe
        50                  55                  60

Ala Phe Asn Met Lys Leu Ser Ala Ile Lys Thr Glu Tyr Leu Tyr Gly
65                  70                  75                  80

Leu Lys Glu Lys Ser Glu Ala Glu Leu Pro Ser Glu Val Lys Ala Lys
                85                  90                  95

Leu Asp Ala Ala Phe Glu Gln Phe Lys Lys Asp Thr Leu Lys Leu Gly
            100                 105                 110

Glu Lys Val Ala Glu Ala Glu Lys Val Ala Glu Ala Glu Lys Lys
            115                 120                 125

Ala Lys Ala Gln Lys Glu Glu Asp Arg Arg Asn Tyr Pro Thr Asn Thr
        130                 135                 140

Tyr Lys Thr Leu Glu Leu Glu Ile Ala Glu Ser Asp Val Glu Val Lys
145                 150                 155                 160

Lys Ala Glu Leu Glu Leu Leu Lys Glu Glu Ala Lys Thr Arg Asn Glu
                165                 170                 175

Asp Thr Ile Asn Gln Ala Lys Ala Lys Val Glu Ser Lys Lys Ala Glu
            180                 185                 190

Ala Thr Lys Leu Glu Glu Ile Lys Thr Asp Arg Lys Lys Ala Glu Glu
        195                 200                 205

Glu Ala Lys Arg Lys Ala Glu Ala Glu Asp Lys Val Lys Asp Lys
        210                 215                 220

Leu Lys Arg Arg Thr Lys Arg Ala Val Pro Gly Glu Pro Ala Thr Pro
225                 230                 235                 240

Asp Lys Lys Glu Asn Asp Ala Lys Ser Ser Asp Ser Val Gly Glu
            245                 250                 255

Glu Thr Leu Pro Ser Pro Ser Leu Lys Ser Gly Lys Lys Val Ala Glu
            260                 265                 270

Ala Glu Lys Lys Val Ala Glu Ala Glu Lys Lys Ala Lys Asp Gln Lys
        275                 280                 285

Glu Glu Asp Arg Arg Asn Tyr Pro Thr Asn Thr Tyr Lys Thr Leu Asp
        290                 295                 300

Leu Glu Ile Ala Glu Ser Asp Val Lys Val Lys Glu Ala Glu Leu Glu
305                 310                 315                 320

Leu Val Lys Glu Glu Ala Lys Gly Ser Arg Asn Glu Glu Lys Ile Asn
                325                 330                 335

Gln Ala Lys Ala Glu Val Glu Ser Lys Lys Ala Glu Ala Thr Arg Leu
            340                 345                 350

Glu Lys Ile Lys Thr Asp Arg Lys Lys Ala Glu Glu Ala Lys Arg
        355                 360                 365

Lys Ala Ala Glu Glu Asp Lys Val Lys Glu Lys Pro Ala Glu Gln Pro
        370                 375                 380

Gln Pro Ala Pro Ala Pro Gln Pro Glu Lys Pro Thr Glu Glu Pro Glu
385                 390                 395                 400

Asn Pro Ala Pro Ala Pro Lys Pro Glu Lys Pro Ala Glu Gln Pro Lys
            405                 410                 415

Ala Glu Lys Thr Asp Asp Gln Gln Ala Glu Glu
            420                 425

<210> SEQ ID NO 35
<211> LENGTH: 413
<212> TYPE: PRT
<213> ORGANISM: Streptococcus pneumoniae

<400> SEQUENCE: 35

```
Glu Asn Glu Gly Ser Thr Gln Ala Ala Thr Ser Ser Asn Met Ala Lys
 1               5                  10                  15

Thr Glu His Arg Lys Ala Ala Lys Gln Val Val Asp Glu Tyr Ile Glu
            20                  25                  30

Lys Met Leu Arg Glu Ile Gln Leu Asp Arg Arg Lys His Thr Gln Asn
        35                  40                  45

Val Ala Leu Asn Ile Lys Leu Ser Ala Ile Lys Thr Lys Tyr Leu Arg
    50                  55                  60

Glu Leu Asn Val Leu Glu Glu Lys Ser Lys Asp Glu Leu Pro Ser Glu
65                  70                  75                  80

Ile Lys Ala Lys Leu Asp Ala Ala Phe Glu Lys Phe Lys Lys Asp Thr
                85                  90                  95

Leu Lys Pro Gly Glu Lys Val Ala Glu Ala Lys Lys Val Glu Glu
            100                 105                 110

Ala Lys Lys Lys Ala Glu Asp Gln Lys Glu Glu Asp Arg Arg Asn Tyr
            115                 120                 125

Pro Thr Asn Thr Tyr Lys Thr Leu Glu Leu Glu Ile Ala Glu Phe Asp
        130                 135                 140

Val Lys Val Lys Glu Ala Glu Leu Glu Leu Val Lys Glu Glu Ala Lys
145                 150                 155                 160

Glu Ser Arg Asn Glu Gly Thr Ile Lys Gln Ala Lys Glu Lys Val Glu
                165                 170                 175

Ser Lys Lys Ala Glu Ala Thr Arg Leu Glu Asn Ile Lys Thr Asp Arg
            180                 185                 190

Lys Lys Ala Glu Glu Ala Lys Arg Lys Ala Asp Ala Lys Leu Lys
        195                 200                 205

Glu Ala Asn Val Ala Thr Ser Asp Gln Gly Lys Pro Lys Gly Arg Ala
    210                 215                 220

Lys Arg Gly Val Pro Gly Glu Leu Ala Thr Pro Asp Lys Lys Glu Asn
225                 230                 235                 240

Asp Ala Lys Ser Ser Asp Ser Val Gly Glu Thr Leu Pro Ser
                245                 250                 255

Ser Ser Leu Lys Ser Gly Lys Lys Val Ala Glu Ala Glu Lys Lys Val
            260                 265                 270

Glu Glu Ala Glu Lys Lys Ala Lys Asp Gln Lys Glu Glu Asp Arg Arg
        275                 280                 285

Asn Tyr Pro Thr Asn Thr Tyr Lys Thr Leu Asp Leu Glu Ile Ala Glu
    290                 295                 300

Ser Asp Val Lys Val Lys Glu Ala Glu Leu Glu Leu Val Lys Glu Glu
305                 310                 315                 320

Ala Lys Glu Pro Arg Asp Glu Lys Ile Lys Gln Ala Lys Ala Lys
                325                 330                 335

Val Glu Ser Lys Lys Ala Glu Ala Thr Arg Leu Glu Asn Ile Lys Thr
            340                 345                 350

Asp Arg Lys Lys Ala Glu Glu Ala Lys Arg Lys Ala Ala Glu Glu
        355                 360                 365

Asp Lys Val Lys Glu Lys Pro Ala Glu Gln Pro Gln Pro Ala Pro Ala
    370                 375                 380
```

Thr Gln Pro Glu Lys Pro Ala Pro Lys Pro Glu Lys Pro Ala Glu Gln
385                 390                 395                 400

Pro Lys Ala Glu Lys Thr Asp Asp Gln Gln Ala Glu Glu
            405                 410

<210> SEQ ID NO 36
<211> LENGTH: 425
<212> TYPE: PRT
<213> ORGANISM: Streptococcus pneumoniae

<400> SEQUENCE: 36

Tyr Ile Ala Ser Leu Phe Leu Gly Gly Val His Ala Glu Gly Val
 1               5                  10                  15

Arg Ser Glu Asn Asn Pro Thr Val Thr Ser Ser Gly Gln Asp Ile Ser
            20                  25                  30

Lys Lys Tyr Ala Asp Glu Val Lys Ser His Leu Glu Lys Ile Leu Ser
            35                  40                  45

Glu Ile Gln Thr Asn Leu Asp Arg Ser Lys His Ile Lys Thr Val Asn
        50                  55                  60

Leu Ile Asn Lys Leu Gln Asp Ile Lys Arg Thr Tyr Leu Tyr Glu Leu
65                  70                  75                  80

Asn Val Leu Glu Asp Lys Ser Lys Ala Glu Leu Pro Ser Lys Ile Lys
                85                  90                  95

Ala Glu Leu Asp Ala Ala Phe Glu Gln Phe Lys Lys Asp Thr Leu Pro
            100                 105                 110

Thr Glu Pro Gly Lys Lys Val Ala Glu Ala Lys Lys Lys Val Glu Glu
            115                 120                 125

Ala Glu Lys Lys Ala Lys Ala Gln Lys Glu Glu Asp Tyr Arg Asn Tyr
        130                 135                 140

Pro Thr Ile Thr Tyr Lys Thr Leu Glu Leu Glu Ile Ala Glu Ser Asp
145                 150                 155                 160

Val Lys Val Lys Glu Ala Glu Leu Glu Leu Val Lys Lys Glu Ala Asp
                165                 170                 175

Glu Ser Arg Asn Glu Gly Thr Ile Asn Gln Ala Lys Ala Lys Val Glu
            180                 185                 190

Ser Glu Gln Ala Glu Ala Thr Arg Leu Lys Lys Ile Lys Thr Asp Arg
        195                 200                 205

Glu Lys Ala Glu Glu Ala Lys Arg Arg Ala Asp Ala Lys Glu Gln
210                 215                 220

Asp Glu Ser Lys Arg Arg Lys Ser Arg Val Lys Arg Gly Asp Phe Gly
225                 230                 235                 240

Glu Pro Ala Thr Pro Asp Lys Lys Glu Asn Asp Ala Lys Ser Ser Asp
                245                 250                 255

Ser Ser Val Gly Glu Glu Thr Leu Pro Ser Pro Ser Leu Lys Pro Gly
            260                 265                 270

Lys Lys Val Ala Glu Ala Glu Lys Val Glu Glu Ala Glu Lys Lys
        275                 280                 285

Ala Lys Asp Gln Lys Glu Glu Asp His Arg Asn Tyr Pro Thr Ile Thr
        290                 295                 300

Tyr Lys Thr Leu Glu Leu Glu Ile Ala Glu Ser Asp Val Glu Val Lys
305                 310                 315                 320

Lys Ala Glu Leu Glu Leu Val Lys Glu Ala Lys Gly Ser Arg Asn
                325                 330                 335

Glu Glu Lys Val Lys Gln Ala Lys Ala Glu Val Glu Ser Lys Lys Ala

-continued

```
                340                 345                 350
Glu Ala Thr Arg Leu Glu Lys Ile Lys Thr Asp Arg Lys Lys Ala Glu
            355                 360                 365
Glu Glu Ala Lys Arg Lys Ala Ala Glu Glu Asp Lys Val Lys Glu Lys
        370                 375                 380
Pro Ala Glu Gln Pro Gln Pro Ala Pro Ala Pro Gln Pro Glu Lys Pro
385                 390                 395                 400
Ala Pro Ala Pro Lys Pro Glu Asn Pro Ala Gln Pro Lys Ala Glu
                405                 410                 415
Lys Pro Ala Asp Gln Gln Ala Glu Glu
            420                 425

<210> SEQ ID NO 37
<211> LENGTH: 439
<212> TYPE: PRT
<213> ORGANISM: Streptococcus pneumoniae

<400> SEQUENCE: 37

Ala Ser Leu Phe Leu Gly Gly Val Val His Ala Glu Gly Val Arg Ser
1               5                   10                  15
Gly Asn Asn Ser Thr Val Thr Ser Ser Gly Gln Asp Ile Ser Lys Lys
            20                  25                  30
Tyr Ala Asp Glu Val Glu Ser His Leu Gln Ser Ile Leu Lys Asp Val
        35                  40                  45
Asn Lys Asn Leu Lys Lys Val Gln His Thr Gln Asn Ala Asp Phe Asn
    50                  55                  60
Lys Lys Leu Ser Lys Ile Lys Thr Lys Tyr Leu Tyr Glu Leu Asn Val
65                  70                  75                  80
Leu Glu Glu Lys Ser Glu Ala Glu Leu Thr Ser Lys Thr Lys Glu Thr
                85                  90                  95
Lys Glu Glu Leu Thr Ala Ala Phe Glu Gln Phe Lys Lys Asp Thr Leu
            100                 105                 110
Ser Thr Glu Pro Glu Lys Lys Val Ala Glu Ala Lys Lys Lys Val Glu
        115                 120                 125
Glu Ala Lys Lys Lys Ala Glu Asp Gln Lys Glu Lys Asp Arg Arg Asn
    130                 135                 140
Tyr Pro Thr Ile Thr Tyr Lys Thr Leu Glu Leu Glu Ile Ala Glu Ser
145                 150                 155                 160
Asp Val Glu Val Lys Lys Ala Glu Leu Glu Leu Val Lys Val Lys Ala
                165                 170                 175
Asn Glu Pro Arg Asp Glu Glu Lys Ile Lys Gln Ala Glu Ala Lys Val
            180                 185                 190
Glu Ser Lys Gln Ala Glu Ala Thr Arg Leu Lys Lys Ile Lys Thr Asp
        195                 200                 205
Arg Glu Gln Ala Glu Ala Thr Arg Leu Glu Asn Ile Lys Thr Asp Arg
    210                 215                 220
Glu Gln Ala Glu Glu Ala Lys Val Lys Asp Glu Pro Lys Lys Arg
225                 230                 235                 240
Thr Lys Arg Gly Val Leu Gly Glu Pro Ala Thr Pro Asp Lys Lys Glu
                245                 250                 255
Asn Asp Ala Lys Ser Ser Asp Ser Ser Val Gly Glu Glu Thr Leu Pro
            260                 265                 270
Ser Pro Ser Leu Lys Pro Glu Lys Lys Val Ala Glu Ala Glu Lys Lys
        275                 280                 285
```

```
Val Glu Glu Ala Lys Lys Ala Glu Asp Gln Lys Glu Glu Asp Arg
    290             295             300
Arg Asn Tyr Pro Thr Asn Thr Tyr Lys Thr Leu Glu Leu Glu Ile Ala
305                 310             315                 320
Glu Ser Asp Val Glu Val Lys Lys Ala Glu Leu Glu Leu Val Lys Glu
                325             330             335
Glu Ala Lys Glu Pro Arg Asn Glu Glu Lys Val Lys Gln Ala Lys Ala
            340             345             350
Glu Val Glu Ser Lys Gln Ala Glu Ala Thr Arg Leu Glu Asn Ile Lys
        355             360             365
Thr Asp Arg Lys Lys Ala Glu Glu Ala Lys Arg Lys Ala Ala Glu
    370             375             380
Glu Asp Lys Val Lys Glu Lys Pro Ala Glu Gln Pro Gln Pro Ala Pro
385                 390             395                 400
Ala Pro Gln Pro Glu Lys Pro Ala Pro Lys Pro Glu Lys Pro Ala Pro
                405             410             415
Ala Pro Lys Pro Glu Asn Pro Ala Glu Gln Pro Lys Ala Glu Lys Pro
            420             425             430
Ala Asp Gln Gln Ala Glu Glu
            435
```

<210> SEQ ID NO 38
<211> LENGTH: 460
<212> TYPE: PRT
<213> ORGANISM: Streptococcus pneumoniae

<400> SEQUENCE: 38

```
Cys Ile Val Ala Ser Leu Val Met Gly Ser Val Val His Ala Thr Glu
  1               5                  10                  15
Asn Glu Gly Ala Thr Gln Val Pro Thr Ser Asn Arg Ala Asn Glu
                 20                  25                  30
Ser Gln Ala Glu Gln Gly Glu Gln Pro Lys Lys Leu Asp Ser Glu Arg
             35                  40                  45
Asp Lys Ala Arg Lys Glu Val Glu Glu Tyr Val Lys Lys Ile Val Gly
         50                  55                  60
Glu Ser Tyr Ala Lys Ser Thr Lys Lys Arg His Thr Ile Thr Val Ala
 65                  70                  75                  80
Leu Val Asn Glu Leu Asn Asn Ile Lys Asn Glu Tyr Leu Asn Lys Ile
                 85                  90                  95
Val Glu Ser Thr Ser Glu Ser Gln Leu Gln Ile Leu Met Met Glu Ser
                100                 105                 110
Arg Ser Lys Val Asp Glu Ala Val Ser Lys Phe Glu Lys Asp Ser Ser
            115                 120                 125
Ser Ser Ser Ser Ser Asp Ser Ser Thr Lys Pro Glu Ala Ser Asp Thr
        130                 135                 140
Ala Lys Pro Asn Lys Pro Thr Glu Pro Gly Glu Lys Val Ala Glu Ala
145                 150                 155                 160
Lys Lys Lys Val Glu Glu Ala Glu Lys Ala Lys Asp Gln Lys Glu
                165                 170                 175
Glu Asp Arg Arg Asn Tyr Pro Thr Ile Thr Tyr Lys Thr Leu Glu Leu
            180                 185                 190
Glu Ile Ala Glu Ser Asp Val Glu Val Lys Lys Ala Glu Leu Glu Leu
        195                 200                 205
Val Lys Val Lys Ala Asn Glu Pro Arg Asp Glu Gln Lys Ile Lys Gln
    210                 215                 220
```

```
Ala Glu Ala Glu Val Glu Ser Lys Gln Ala Glu Ala Thr Arg Leu Lys
225                 230                 235                 240

Lys Ile Lys Thr Asp Arg Glu Ala Glu Glu Ala Lys Arg Arg
            245                 250                 255

Ala Asp Ala Lys Glu Gln Gly Lys Pro Lys Gly Arg Ala Lys Arg Gly
            260                 265                 270

Val Pro Gly Glu Leu Ala Thr Pro Asp Lys Lys Glu Asn Asp Ala Lys
            275                 280                 285

Ser Ser Asp Ser Ser Val Gly Glu Glu Thr Leu Pro Ser Pro Ser Leu
            290                 295                 300

Lys Pro Glu Lys Lys Val Ala Glu Ala Glu Lys Lys Val Glu Glu Ala
305                 310                 315                 320

Lys Lys Lys Ala Glu Asp Gln Lys Glu Glu Asp Arg Arg Asn Tyr Pro
                325                 330                 335

Thr Asn Thr Tyr Lys Thr Leu Glu Leu Glu Ile Ala Glu Ser Asp Val
            340                 345                 350

Glu Val Lys Lys Ala Glu Leu Glu Leu Val Lys Glu Glu Ala Lys Glu
            355                 360                 365

Pro Arg Asn Glu Glu Lys Val Lys Gln Ala Lys Ala Glu Val Glu Ser
            370                 375                 380

Lys Lys Ala Glu Ala Thr Arg Leu Glu Lys Ile Lys Thr Asp Arg Lys
385                 390                 395                 400

Lys Ala Glu Glu Ala Lys Arg Lys Ala Ala Glu Glu Asp Lys Val
                405                 410                 415

Lys Glu Lys Pro Ala Glu Gln Pro Gln Pro Ala Pro Ala Pro Lys Ala
            420                 425                 430

Glu Lys Pro Ala Pro Ala Pro Lys Pro Glu Asn Pro Ala Glu Gln Pro
            435                 440                 445

Lys Ala Glu Lys Pro Ala Asp Gln Gln Ala Glu Glu
            450                 455                 460

<210> SEQ ID NO 39
<211> LENGTH: 459
<212> TYPE: PRT
<213> ORGANISM: Streptococcus pneumoniae

<400> SEQUENCE: 39

Ile Val Ala Ser Leu Val Met Gly Ser Val Val His Ala Thr Glu Asn
  1               5                  10                  15

Glu Gly Ala Thr Gln Val Pro Thr Ser Ser Asn Arg Ala Asn Glu Ser
                20                  25                  30

Gln Ala Glu Gln Gly Gln Pro Lys Lys Leu Asp Ser Glu Arg Asp
            35                  40                  45

Lys Ala Arg Lys Glu Val Glu Glu Tyr Val Lys Lys Ile Val Gly Glu
     50                  55                  60

Ser Tyr Ala Lys Ser Thr Lys Lys Arg His Thr Ile Thr Val Ala Leu
 65                  70                  75                  80

Val Asn Glu Leu Asn Asn Ile Lys Asn Glu Tyr Leu Asn Lys Ile Val
                85                  90                  95

Glu Ser Thr Ser Glu Ser Gln Leu Gln Ile Leu Met Met Glu Ser Arg
                100                 105                 110

Ser Lys Val Asp Glu Ala Val Ser Lys Phe Glu Lys Asp Ser Ser Ser
            115                 120                 125

Ser Ser Ser Ser Asp Ser Ser Thr Lys Pro Glu Ala Ser Asp Thr Ala
```

```
            130                 135                 140
Lys Pro Asn Lys Pro Thr Glu Pro Gly Glu Lys Val Ala Glu Ala Lys
145                 150                 155                 160

Lys Lys Val Glu Glu Val Glu Lys Lys Ala Lys Asp Gln Lys Glu Glu
                165                 170                 175

Asp Arg Arg Asn Tyr Pro Thr Ile Thr Tyr Lys Thr Leu Glu Leu Glu
                180                 185                 190

Ile Ala Glu Ser Asp Val Glu Val Lys Lys Ala Glu Leu Glu Leu Val
                195                 200                 205

Lys Val Lys Ala Asn Glu Pro Arg Asp Lys Gln Lys Ile Lys Gln Ala
210                 215                 220

Glu Ala Glu Val Glu Ser Lys Gln Ala Glu Ala Thr Arg Leu Lys Lys
225                 230                 235                 240

Ile Lys Thr Asp Arg Glu Ala Glu Glu Ala Lys Arg Arg Ala
                245                 250                 255

Asp Ala Lys Glu Gln Gly Lys Pro Lys Gly Arg Pro Lys Arg Gly Val
                260                 265                 270

Pro Gly Glu Leu Ala Thr Pro Asp Lys Glu Asn Asp Ala Lys Ser
            275                 280                 285

Ser Asp Ser Ser Val Gly Glu Glu Thr Leu Pro Ser Pro Ser Leu Lys
    290                 295                 300

Pro Glu Lys Lys Val Ala Glu Ala Glu Lys Lys Val Glu Glu Ala Lys
305                 310                 315                 320

Lys Lys Ala Glu Asp Gln Lys Glu Glu Asp Arg Arg Asn Tyr Pro Thr
                325                 330                 335

Asn Thr Tyr Lys Thr Leu Glu Leu Glu Ile Ala Glu Ser Asp Val Glu
                340                 345                 350

Val Lys Lys Ala Glu Leu Glu Leu Val Lys Glu Glu Ala Lys Glu Pro
            355                 360                 365

Arg Asn Glu Glu Lys Val Lys Gln Ala Lys Ala Glu Val Glu Ser Lys
            370                 375                 380

Lys Ala Glu Ala Thr Arg Leu Glu Lys Ile Lys Thr Asp Arg Lys Lys
385                 390                 395                 400

Ala Glu Glu Glu Ala Lys Arg Lys Ala Ala Glu Glu Asp Lys Val Lys
                405                 410                 415

Glu Lys Pro Ala Glu Gln Pro Gln Pro Ala Pro Ala Pro Lys Thr Glu
                420                 425                 430

Lys Pro Ala Pro Ala Pro Lys Pro Glu Asn Pro Ala Glu Gln Pro Lys
            435                 440                 445

Ala Glu Lys Pro Ala Asp Gln Gln Ala Glu Glu
    450                 455

<210> SEQ ID NO 40
<211> LENGTH: 437
<212> TYPE: PRT
<213> ORGANISM: Artificial Sequence
<220> FEATURE:
<223> OTHER INFORMATION: consensus sequence

<400> SEQUENCE: 40

Ala Val Ala Ser Leu Val Met Gly Ser Val His Ala Thr Glu Asn
  1               5                  10                  15

Glu Val Thr Thr Gln Val Ala Thr Ser Ser Asn Arg Ala Asn Glu Ser
                20                  25                  30

Gln Thr Glu His Arg Lys Ala Ala Lys Gln Val Asp Glu Tyr Ile Lys
```

35                  40                  45
Lys Met Leu Gln Leu Asp Arg Arg Lys His Thr Gln Asn Val Ala Leu
 50                  55                  60

Asn Thr Lys Leu Ser Ala Ile Lys Thr Glu Tyr Leu Asn Gly Leu Ser
 65                  70                  75                  80

Val Leu Glu Glu Lys Ser Glu Ala Glu Leu Pro Ser Glu Ile Lys Ala
                 85                  90                  95

Lys Leu Asp Ala Ala Phe Glu Gln Phe Lys Lys Asp Thr Leu Pro Thr
                100                 105                 110

Glu Pro Gly Lys Lys Val Ala Glu Ala Glu Lys Val Glu Glu Ala
                115                 120                 125

Lys Lys Lys Ala Glu Asp Gln Lys Glu Glu Asp Arg Arg Asn Tyr Pro
130                 135                 140

Thr Ile Thr Tyr Lys Thr Leu Glu Leu Glu Ile Ala Glu Ser Asp Val
145                 150                 155                 160

Glu Val Lys Lys Ala Glu Leu Glu Leu Val Lys Glu Ala Lys Glu
                165                 170                 175

Ser Arg Asp Glu Gly Lys Ile Asn Gln Ala Lys Ala Lys Val Glu Ser
                180                 185                 190

Lys Lys Ala Glu Ala Thr Arg Leu Lys Lys Ile Lys Thr Asp Arg Glu
                195                 200                 205

Lys Ala Glu Glu Glu Ala Lys Arg Arg Ala Asp Ala Lys Leu Gln Glu
                210                 215                 220

Ala Asn Val Ala Ser Glu Gln Asp Lys Pro Lys Gly Arg Ala Lys Arg
225                 230                 235                 240

Gly Val Pro Gly Glu Leu Ala Thr Pro Asp Lys Lys Glu Asn Asp Ala
                245                 250                 255

Lys Ser Ser Asp Ser Ser Val Gly Glu Glu Thr Leu Pro Ser Pro Ser
                260                 265                 270

Leu Lys Pro Glu Lys Lys Val Ala Glu Ala Glu Lys Lys Val Glu Glu
                275                 280                 285

Ala Lys Lys Lys Ala Glu Asp Gln Lys Glu Glu Asp Arg Arg Asn Tyr
290                 295                 300

Pro Thr Asn Thr Tyr Lys Thr Leu Glu Leu Glu Ile Ala Glu Ser Asp
305                 310                 315                 320

Val Glu Val Lys Lys Ala Glu Leu Glu Leu Val Lys Glu Glu Ala Lys
                325                 330                 335

Glu Ser Arg Asn Glu Glu Lys Val Lys Gln Ala Lys Ala Glu Val Glu
                340                 345                 350

Ser Lys Lys Ala Glu Ala Thr Arg Leu Glu Lys Ile Lys Thr Asp Arg
                355                 360                 365

Lys Lys Ala Glu Glu Glu Ala Lys Arg Lys Ala Ala Glu Glu Asp Lys
                370                 375                 380

Val Lys Glu Lys Pro Ala Glu Gln Pro Gln Pro Ala Pro Ala Pro Gln
385                 390                 395                 400

Pro Glu Lys Pro Ala Glu Glu Pro Glu Asn Pro Ala Pro Ala Pro Pro
                405                 410                 415

Lys Pro Glu Asn Pro Ala Glu Gln Pro Lys Ala Glu Lys Pro Ala Asp
                420                 425                 430

Gln Gln Ala Glu Glu
                435

<210> SEQ ID NO 41

```
-continued

<211> LENGTH: 23
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: 15
<223> OTHER INFORMATION: r = A or G
<220> FEATURE:
<221> NAME/KEY: misc_feature
<222> LOCATION: 18
<223> OTHER INFORMATION: y = C or T
<220> FEATURE:
<221> NAME/KEY: misc_feature
<222> LOCATION: 21
<223> OTHER INFORMATION: r = A or G

<400> SEQUENCE: 41 ggc gga tcc atg gar aay gar gg                                    23

<210> SEQ ID NO 42
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 42 gcc gtc gac tta gtt tac cca ttc acc att ggc                       33
```

POLYPEPTIDE COMPRISING THE AMINO ACID OF AN N-TERMINAL CHOLINE BINDING PROTEIN A TRUNCATE, VACCINE DERIVED THEREFROM AND USES THEREOF

FIELD OF THE INVENTION

The present invention relates generally to a polypeptide of a N-terminal choline binding protein A truncate. The invention also relates to vaccines which provide protection or elicit protective antibodies to bacterial infection, specifically *pneumococcus*, and to antibodies and antagonists against such polypeptide for use in diagnosis and passive immune therapy. The polypeptide and/or the nucleic acid encoding the polypeptide are also useful as a competitive inhibitor of bacterial adhesin of *pneumococcus*. Lastly, this invention is directed to therapeutics using the polypeptide.

BACKGROUND OF THE INVENTION

*Streptococcus pneumoniae* is a gram positive bacteria which is a major cause of invasive infections such as sepsis, meningitis, otitis media and lobar pneumonia (Tuomanen et al NEJM 322:1280–1284, 1995). Pneumococci bind avidly to cells of the upper and lower respiratory tract. Like most bacteria, adherence of pneumococci to human cells is achieved by presentation of bacterial surface proteins that bind to eukaryotic carbohydrates in a lectin-like fashion (Cundell, D. & Tuomanen, E. (1994) *Microb Pathog* 17:361–374). Pneumococci bind to non-inflamed epithelium, a process that can be viewed as asymptomatic carriage. It has been proposed that the conversion to invasive disease involves the local generation of inflammatory factors which, activating the human cell, change the number and type of receptors available on the human cells (Cundell, D. et al. (1995) *Nature,* 377:435–438). Presented with an opportunity in this new setting, pneumococci appear to take advantage and engage one of these unregulated receptors, the platelet activating factor (PAF) receptor (Cundell et al. (1995) *Nature,* 377:435–438. Within minutes of the appearance of the PAF receptor, pneumococci undergo waves of enhanced adherence and invasion. Inhibition of bacterial binding to activated cells, for instance by soluble receptor analogs, blocks the progression to disease in animal models (Idanpaan-Heikkila, I. et al. (1997) *J. Infect. Dis.,* 176:704–712). Particularly effective in this regard are soluble carbohydrates containing lacto-N-neotetraose with or without an additional sialic acid which prevent pneumococcal attachment to human cells in vitro and prevent colonization in the lung in vivo.

Choline Binding Proteins: Candidate Structural Adhesin Gene:

Pneumococci produce a family of surface proteins capable of binding to the bacterial surface by non-covalent association to the cell wall teichoic acid or lipoteichoic acid. The surface of *Streptococcus pneumoniae* is decorated with a family of CBPs (Choline Binding Proteins) that are non-covalently bound to the phosphorylcholine. CbpA, is an 75 kD surface-exposed choline binding protein that shows a chimeric architecture. There is a unique N-terminal domain a proline rich region followed by a C-terminal domain comprised of 10 repeated region responsible for binding to choline.

CbpA, is an adhesin (ligand) for the glycoconjugate containing receptors present on the surface of eucaryotic cells. Mutants with defects in cbpA showed reduced virulence in the infant rat model for nasopharyngeal colonization. This binding is directed to choline determinants which decorate the teichoic acid and is mediated by a signature choline binding domain in each of the members of this family of proteins. The choline binding domain was discovered and fully characterized by Lopez et al. in his studies of the autolytic enzyme (Ronda et al. (1987) *Eur. J. Biochem,* 164:621–624). Other proteins containing this domain include the autolysin of the pneumococcal phage and the protective antigen, pneumococcal surface protein A (PspA) (Ronda, C. et al. (1987) *Eur. J Biochem,* 164:621–624 and McDaniel, L. S., et al. (1992)*Microb Pathog,* 13:261–269). CbpA, fails to colonize the nasopharynx domain which is shared with its other family members C terminus) but its activity of binding to human cells arises from its unique N-terminal domain. Since the process of colonization and the progression to disease depend on pneumococcal attachment to human cells as a primary step, interruption of the function of the N terminal domain, either by cross reactive antibody or by competitive inhibition with a peptide mimicking this domain, may be critical to blocking disease.

Choline binding proteins for anti-pneumococcal vaccines are discussed in PCT International Application No. PCT/US97107198 and such PCT Application is incorporated in its entirety by reference. Current vaccines against *S. pneumoniae* employ purified carbohydrates of the capsules of the 23 most common serotypes of this bacterium, but such vaccine is only 50% protective (Shapiro et al. NJEM 325:1453, 1991) and is not immunogenic under the age of 2. Further, a therapeutic polypeptide would offer a therapeutic option in cases of infection with multi resistant organisms. Therefore, the invention herein fills a long felt need by providing a protective vaccines.

SUMMARY OF THE INVENTION

The present invention provides an isolated polypeptide comprising an amino acid sequence of a N-terminal choline binding protein A truncate. The polypeptide comprises the amino acid sequence as set forth in SEQ ID NOS 1, 3–7, or 9–11, including fragments, mutants, variants, analogs, or derivatives, thereof. Also, this invention provides an isolated polypeptide comprising an amino acid sequence of a N-terminal choline binding protein A truncate having the amino acid as set forth in SEQ ID NO 24, wherein the polypeptide exhibits its tertiary structure and methods of preparation such a polypeptide. The isolated polypeptide are suitable for use in immunizing animals and humans against bacterial infection, preferably pneumococci.

In a still further aspect, the present invention extends to an N-terminal choline binding protein A truncate having lectin activity and no choline binding activity. Still further, this invention provides an immunogenic N-terminal choline binding protein A truncate or a fragment thereof.

The present invention also relates to isolated nucleic acids, such as recombinant DNA molecules or cloned genes, or degenerate variants thereof, mutants, analogs, or fragments thereof, which encode the isolated polypeptide or which competitively inhibit the activity of the polypeptide. Preferably, the isolated nucleic acids which includes degenerates, variants, mutants, analogs, or fragments thereof, has a sequence as set forth in SEQ ID NOS: 12, 14–17, 19–22 or 23. In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present invention, and more particularly, the DNA sequences or fragments thereof determined from the sequences set forth above.

Antibodies against the isolated polypeptide include naturally raised and recombinantly prepared antibodies. These may include both polyclonal and monoclonal antibodies prepared by known genetic techniques, as well as bi-specific (chimeric) antibodies, and antibodies including other functionalities suiting them for diagnostic use conjunctive with their capability of modulating bacterial adherence including but not limited to acting as competitive agents.

It is still a further object of the present invention to provide a method for the treatment of mammals to control the amount or activity of the bacteria or its subunits, so as to treat or avert the adverse consequences of invasive, spontaneous, or idiopathic pathological states. This invention provides pharmaceutical compositions for use in therapeutic methods which comprise or are based upon the isolated polypeptides, their subunits or their binding partners.

Lastly, this invention provides pharmaceutical compositions, vaccines, and diagnostic and therapeutic methods of use thereof.

BRIEF DESCRIPTION OF THE DRAWINGS

FIG. 2A-B. Comparison of homologies of various serotypes of the nucleic acid and amino acid sequence of the N-terminal region of CbpA (SEQ ID NOS: 28–39). Specifically, SPB328 corresponds to SEQ ID NO:28; SPB365 corresponds to SEQ ID NO:29; SPB105 corresponds to SEQ ID NO:30; SPSJ12 corresponds to SEQ ID NO:31; SPB331 corresponds to SEQ ID NO:32; SPR332 corresponds to SEQ ID NO: 33; ATCC2 corresponds to SEQ ID NO:34; R6 corresponds to SEQ ID NO:35; SPSJ9 corresponds to SEQ ID NO:36; ATCC6B corresponds to SEQ ID NO:37; Ntype4 corresponds to SEQ ID NO:38; and ATCC4 corresponds to SEQ ID NO:39. The consensus sequence appearing in FIG. 2 is set forth in SEQ ID NO:40.

FIG. 7. Results of active protection in mice. Immune sera against recombinant R1 protected mice from lethal *S. pneumoniae* challenge (challenge 560 cfu serotype 6B).

DETAILED DESCRIPTION

The present invention is directed to an isolated polypeptide comprising an amino acid sequence of a N-terminal choline binding protein A truncate. The polypeptides are suitable for use in immunizing animals against pneumococcal infection. These polypeptide or peptide fragments thereof, when formulated with an appropriate adjuvant, are used in vaccines for protection against pneumococci, and against other bacteria with cross-reactive proteins.

This invention provides an isolated polypeptide comprising an amino acid sequence of a N-terminal choline binding protein A truncate. In one embodiment the polypeptide has the amino acid sequence as set forth in any of SEQ ID NO 1, 3–5, 7, or 9–11, including fragments, mutants, variants, analogs, or derivatives, thereof. In another embodiment the polypeptide has the amino acid KXXE (SEQ ID NO 6).

Figures 2, 2B, 3:
Figure 3:
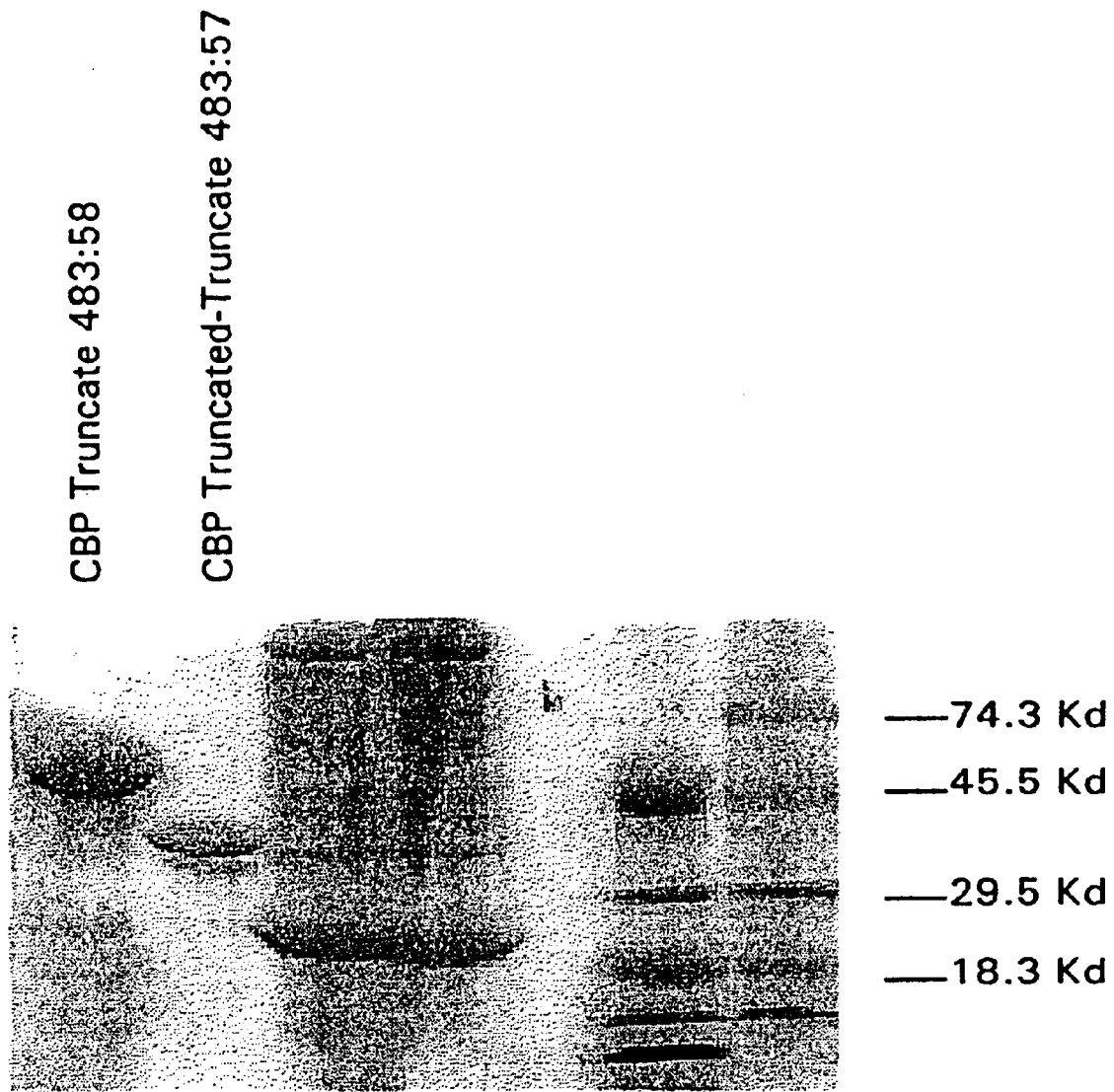
FIG. 3. Expression and purification of recombinant R1 and R2.

This invention provides an isolated polypeptide comprising an amino acid sequence of a N-terminal choline binding protein A truncate as set forth in FIG. 2. In one embodiment, the polypeptide has an amino acid sequence which is a conserved region as set forth in FIG. 2. For example, conserved regions include but are not limited to amino acid sequence 158 to 210; 158 to 172; 300 to 321; 331 to 339; 355 to 365; 367 to 374; 379 to 389; 409 to 427; and 430 to 447. FIG. 2 sets forth homologies of various serotypes of the nucleic acid and amino acid sequence of the N-terminal region of CbpA which are contemplated by this invention.

Further, this invention provides an isolated polypeptide comprising an amino acid sequence of a N-terminal choline binding protein A truncate having the amino acid as set forth in SEQ ID NO 24, wherein the polypeptide exhibits its tertiary structure. In one embodiment the polypeptide is an analog, fragment, mutant, or variant thereof. Variants contemplated are set forth in FIG. 2. This invention also provides an isolated polypeptide comprising an amino acid sequence of a N-terminal choline binding protein A truncate having the amino acid from about position 16 to about position 475 of serotype 4 as set forth in FIG. 2 or a corresponding amino acid of serotype 4 as shown in FIG. 2, wherein the polypeptide exhibits its tertiary structure. In one embodiment tertiary structure corresponds to that present in the native protein.

Methods of preparation of the polypeptide are for example as follows: cleaving a full length choline binding protein A with hydroxylamine, wherein the hydroxylamine cleaves the choline binding protein A at amino acid Asparagine (N) at position 475 of serotype R6x and serotype 4, or the corresponding amino acid of serotype R6x or serotype 4 in a different serotype as shown in FIG. 2, thereby creating the N-terminal choline binding protein A truncate. Alternative methods which create a truncated choline binding protein A or fragment thereof, and retain the native tertiary structure (i.e. that of the full length choline binding protein A) are contemplated and known to those skilled in the art. Because the polypeptide retains its tertiary structure, the isolated polypeptide is suitable for use as an immunogen in immunizing animals and humans against bacterial infection, preferably pneumococci.

The polypeptide comprising the amino acid sequence of choline binding protein A (CbpA) serotype type 4 is as follows:
ENEGATQVPTSSNRANESQAEQGEQP-
KKLDSERDKARKEVEEYVKKIVGESY AKST-
KKRHTITVALVNELNNIKNEY-
LNKIVESTSESQLQILMMESRSKVDEAV
SKFEKDSSSSSSSDSSTKPEASDTAKP- NKPTEPGEKVAEAKKKVEEAEKKAKD
QKEEDRRNYPTITYKTLELEIAESD-
VEVKKAELELVKVKANEPRDEQKIKQAE
AEVESKQAEATRLKKIKTDREEAEEE-
AKRRADAKEQGKPKGRAKRGVPGEL ATPDKK-
ENDAKSSDSSVGEETLPSPSLKPEKK-
VAEAEKKVEEAKKKAEDQKE
EDRRNYPTNTYKTLELEIAESDVEVK-
KAELELVKEEAKEPRNEEKVKQAKAE VESKKAE-
ATRLEKIKTDRKKAEEEAKRKAAEED-
KVKEKPAEQPQPAPAPKAE KPAPAPKPEN (SEQ ID NO 24).

"Polypeptide R2" means a polypeptide comprising the amino acid sequences from position 16 to position 444 of the N-terminal truncate of choline binding protein A (CbpA) serotype type 4 (see FIG. 1) which has the following sequence:
ENEGATQVPTSSNRANESQAEQGEQP-
KKLDSERDKARKEVEEYVKKIVGESY AKST-
KKRHTITVALVNELNNIKNEY-
LNKIVESTSESQLQILMMESRSKVDEAVS
KFEKDSSSSSSSDSSTKPEASDTAKP-
NKPTEPGEKVAEAKKKVEEAEKKAKDQ
KEEDRRNYPTITYKTLELEIAESDVEVK-
KAELELVKVKANEPRDEQKIKQAEA EVESKQAE-
ATRLKKIKTDREEAEEE-
AKRRADAKEQGKPKGRAKRGVPGELAT
PDKKENDAKSSDSSVGEETLPSPSLKPE-
KKVAEAEKKVEEAKKKAEDQKEED RRNYPTNTYK-
TLELEIAESDVEVKKAELELVKEE-
AKEPRNEEKVKQAKAEVE
SKKAEATRLEKIKTDRKKAEEEAKR-
KAAEEDKVKEKPA (SEQ ID NO I).

The DNA sequence which encodes polypeptide R2 of the N-terminal truncate of choline binding protein A (CbpA) serotype type 4:
GAGAACGAGGGAGCTACCCAAGTAC-
CCACTTCTTCTAATAGGGCAAATGAAAGTCAGGCA-
GAACAAGGAGAACAACCTAAAAAACTC-
GATTCAGAACGA
GATAAGGCAAGGAAAGAGGTCGAG-
GAATATGTAAAAAAAATAGTGGGTG AGAGCTATG-
CAAAATCAACTAAAAAGCGACATACAAT-
TACTGTAGCTCTA
GTTAACGAGTTGAACAACATTAAGAAC-
GAGTATTTGAATAAAATAGTTGA ATCAACCTCA-
GAAAGCCAACTACAGATACTGATGATG-
GAGAGTCGATCAA
AAGTAGATGAAGCTGT-
GTCTAAGTTTGAAAAGGACTCATCTTCTTCGTCAA
GTTCAGACTCTTCCACTAAACCG-
GAAGCTTCAGATACAGCGAAGCCAAAC AAGC-
CGACAGAACCAGGAGAAAAGGTAGCA-
GAAGCTAAGAAGAAGGTTG
AAGAAGCTGAGAAAAAAGCCAAGGAT-
CAAAAAGAAGAAGATCGTCGTAA CTACCCAAC-
CATTACTTACAAAACGCTTGAACT-
TGAAATTGCTGAGTCCGA
TGTGGAAGTTAAAAAAGCGGAGCT-
TGAACTAGTAAAAGTGAAAGCTAAC GAACCTC-
GAGACGAGCAAAAAATTAAGCAAGCA-
GAAGCGGAAGTTGAGA
GTAAACAAGCTGAGGCTACAAGGT-
TAAAAAAAATCAAGACAGATCGTGA AGAAGCA-
GAAGAAGAAGCTAAACGAAGAGCAGAT-
GCTAAAGAGCAAGGT
AAACCAAAGGGGCGGGCAAAACGAG-
GAGTTCCTGGAGAGCTAGCAACAC
CTGATAAAAAAGAAAATGATGC-
GAAGTCTTCAGATTCTAGCGTAGGTGAA
GAAACTCTTCCAAGCCCATCCCTGAAAC-
CAGAAAAAAAGGTAGCAGAAG CTGAGAAGAAG-
GTTGAAGAAGCTAAGAAAAAAGCCGAG-
GATCAAAAAGA
AGAAGATCGCCGTAACTACCCAAC-
CAATACTTACAAAACGCTTGAACTTG AAATTGCT-
GAGTCCGATGTGGAAGTTAAAAAAGCG-
GAGCTTGAACTAGTA
AAAGAGGAAGCTAAGGAACCTCGAAAC-
GAGGAAAAAGTTAAGCAAGCAA AAGCGGAAGT-
TGAGAGTAAAAAAGCTGAGGCTACAAG-
GTTAGAAAAAAT
CAAGACAGATCGTAAAAAAGCAGAAGAA-
GAAGCTAAACGAAAAGCAGCA GAAGAA-
GATAAAGTTAAAGAAAAACCAGCTG (SEQ ID NO 12).

Amino acid sequence of CbpA of serotype 4:
ENEGATQVPTSSNRANESQAEQGEQP-
KKLDSERDKARKEVEEYVKKIVGESY AKST-
KKRHTITVALVNELNNIKNEY-
LNKIVESTSESQLQILMMESRSKVDEAV
SKFEKDSSSSSSSDSSTKPEASDTAKP-
NKPTEPGEKVAEAKKKVEEAEKKAKD
QKEEDRRNYPTITYKTLELEIAESD-
VEVKKAELELVKVKANEPRDEQKIKQAE
AEVESKQAEATRLKKIKTDREEAEEE-
AKRRADAKEQGKPKGRAKRGVPGEL ATPDKK-
ENDAKSSDSSVGEETLPSPSLKPEKK-
VAEAEKKVEEAKKKAEDQKE
EDRRNYPTNTYKTLELEIAESDVEVK-
KAELELVKEEAKEPRNEEKVKQAKAE VESKKAE-
ATRLEKIKTDRKKAEEEAKRKAAEED-
KVKEKPAEQPQPAPAPKAE
KPAPAPKPENPAEQPKAEKPADQQAEED-
YARRSEEEYNRLTQQQPPKTEKPA QPSTPKTG-
WKQENGMWYFYNTDGSMATGWLQNNGSW-
YYLNSNGAMATG
WLQNNGSWYYLNANGSMATGWLQNNGSW-
YYLNANGSMATGWLQYNGS WYYLNANGSMATG-
WLQYNGSWYYLNANGDMATGWVKDGDTW-
YYLEAS
GAMKASQWFKVSDKWYYVNGSGALAVNT-
TVDGYGVNANGEWVN. (SEQ ID NO 2)

Figure 1:
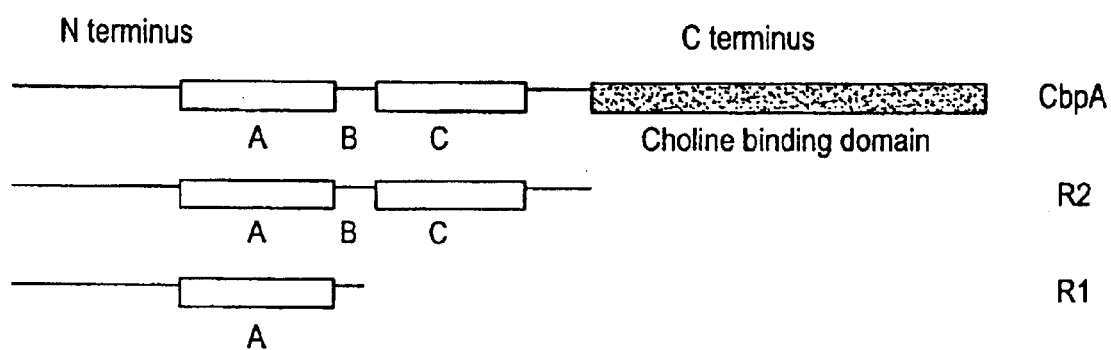
FIG. 1. Schematic representation of choline binding protein A (CbpA) and recombinant truncates R1 (from about amino acid 16 to amino acid 321 from the N-terminus of CbpA as set forth in FIG. 2) and R2 (from about amino acid 16 to amino acid 444 from the N-terminus of CbpA as set forth in FIG. 2). Domain A is from about amino acid 153 to amino acid 321 from the N-terminus of CbpA amino acid sequence as set forth in FIG. 2; domain B is from about amino acid 270 to amino acid 326 from the N-terminus of CbpA amino acid sequence as set forth in FIG. 2); and C is from about amino acid 327 to amino acid 433 from the N-terminus of CbpA amino acid sequence as set forth in FIG. 2.

DNA sequence encoding the amino acid sequence of the CbpA of serotype 4:
GAGAACGAGGGAGCTACCCAAGTAC-
CCACTTCTTCTAATAGGGCAAATGAAAGTCAGGCA-
GAACAAGGAGAACAACCTAAAAAACTC-
GATTCAGAACGA
GATAAGGCAAGGAAAGAGGTCGAG-
GAATATGTAAAAAAAATAGTGGGTG AGAGCTATG-
CAAAATCAACTAAAAAGCGACATACAAT-
TACTGTAGCTCTA
GTTAACGAGTTGAACAACATTAAGAAC-
GAGTATTTGAATAAAATAGTTGA ATCAACCTCA-
GAAAGCCAACTACAGATACTGATGATG-
GAGAGTCGATCAA
AAGTAGATGAAGCTGT-
GTCTAAGTTTGAAAAGGACTCATCTTCTTCGTCAA
GTTCAGACTCTTCCACTAAACCG-
GAAGCTTCAGATACAGCGAAGCCAAAC AAGC-
CGACAGAACCAGGAGAAAAGGTAGCA-
GAAGCTAAGAAGAAGGTTG
AAGAAGCTGAGAAAAAAGCCAAGGAT- CAAAAAGAAGAAGATCGTCGTAA CTACCCAAC-
CATTACTTACAAAACGCTTGAACT-
TGAAATTGCTGAGTCCGA
TGTGGAAGTTAAAAAAGCGGAGCT-
TGAACTAGTAAAAGTGAAAGCTAAC GAACCTC-
GAGACGAGCAAAAAATTAAGCAAGCA-
GAAGCGGAAGTTGAGA
GTAAACAAGCTGAGGCTACAAGGT-
TAAAAAAAATCAAGACAGATCGTGA AGAAGCA-
GAAGAAGAAGCTAAACGAAGAGCAGAT-
GCTAAAGAGCAAGGT
AAACCAAAGGGGCGGGCAAAACGAG-
GAGTTCCTGGAGAGCTAGCAACAC
CTGATAAAAAGAAAATGATGC-
GAAGTCTTCAGATTCTAGCGTAGGTGAA
GAAACTCTTCCAAGCCCATCCCTGAAAC-
CAGAAAAAAGGTAGCAGAAG CTGAGAAGAAG-
GTTGAAGAAGCTAAGAAAAAGCCGAG-
GATCAAAAAGA
AGAAGATCGCCGTAACTACCCAAC-
CAATACTTACAAAACGCTTGAACTTG AAATTGCT-
GAGTCCGATGTGGAAGTTAAAAAAGCG-
GAGgCTTGAACTAGT
AAAAGAGGAAGCTAAGGAACCTCGAAAC-
GAGGAAAAAGTTAAGCAAGCA AAAGCGGAAGT-
TGAGAGTAAAAAAGCTGAGGCTACAAG-
GTTAGAAAAA
TCAAGACAGATCGTAAAAAAGCAGAA-
GAAGAAGCTAAACGAAAAGCAGC AG "Polypeptide A/R2" means a polypeptide comprising a repeat region A within R2, wherein the repeat region A has the amino acid sequences from position 153 to position 269 of the N-terminal of choline binding protein A (CbpA) serotype type 4 which has the following sequence: TEPGEKVAEAKKKVEEAEKKAKDQ-KEEDRRNYPTITYKTLELEIAESDVEVK KAELELVKVKANEPRDEQKIKQAEAE-VESKQAEATRLKKIKTDREEAEEEAK RRADA (SEQ ID NO 5). As shown in FIG. 1, region A of polypeptide R2 is the same region A as within R1.

The DNA sequence which encodes the polypeptide A/R2 is:
ACAGAACCAGGAGAAAAGGTAGCA-GAAGCTAAGAAGAAGGTTGAAGAAG CTGAGAAAAAAGCCAAGGATCAAAAA-GAAGAAGATCGTCGTAACTACCC AACCATTACTTA-CAAAACGCTTGAACTTGAAATTGCT-GAGTCCGATGTGG AAGTTAAAAAAGCGGAGCTTGAACTAG-TAAAAGTGAAAGCTAACGAACC TCGAGACGAG-CAAAAAATTAAGCAAGCAGAAGCG-GAAGTTGAGAGTAAA CAAGCTGAGGCTACAAGGT-TAAAAAAAATCAAGACAGATCGTGAAGAAG CAGAAGAAGAAGCTAAACGAAGAGCAGATGCT (SEQ ID NO 16).

The identity or location of one or more amino acid residues may be changed or modified to include variants such as, for example, deletions containing less than all of the residues specified for the protein, substitutions wherein one or more residues specified are replaced by other residues and additions wherein one or more amino acid residues are added to a terminal or medial portion of the polypeptide (see FIG. 2). These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors. Specifically, examples of the amino acid substitutions of serotype 4, included but not limited to, are as follows: E at position 154 is substituted with K; P at position 155 is substituted with L; G at position 156 is substituted with E; E at position 157 is substituted with K; K at position 181 is substituted with E; D at position 182 is substituted with A; R at position 187 is substituted with Y, H, or L; I at position 194 is substituted with N; E at position 200 is substituted with D; E at position 202 is substituted with D; E at position 209 is substituted with K; K at position 212 is substituted with E; V at position 218 is substituted with L; V at position 220 is substituted with K or E; K at position 221 is substituted with E; N at position 223 is substituted with D or K; P at position 225 is substituted with S, T, or R; D at position 227 is substituted with N; E at position 228 is substituted with K; Q at position 229 is substituted with E, G, or D; K at position 230 is substituted with T; K at position 232 is substituted with N; E at position 235 is substituted with K; A at position 236 is substituted with E; E at position 237 is substituted with K; S at position 240 is substituted with N; K at position 241 is substituted with E; Q at position 242 is substituted with K; K at position 249 is substituted with E; K at position 250 is substituted with N; E at position 257 is substituted with Q or K; A at position 263 is substituted with L; K at position 264 is substituted with E; R at position 265 is substituted with N; R at position 266 is substituted with I; A at position 267 is substituted with K or V; D at position 258 is substituted with T; A at position 269 is substituted with D; A at position 291 is substituted with T, V, P, G, or X; G at position 294 is substituted with G, A, or E; V at position 295 is substituted with D, or A; P at position 295 is substituted with L or F; L at position 299 is substituted with P or Q; P at position 328 is substituted with S; E at position 329 is substituted with G; E at position 340 is substituted with A; K at position 343 is substituted with E or D; E at position 347 is substituted with K; D at position 349 is substituted with A; R at position 354 is substituted with H; E at position 366 is substituted with D; E at position 375 is substituted with K; K at position 378 is substituted with E; E at position 390 is substituted with G; P at position 391 is substituted with S; N at position 393 is substituted with D; V at position 397 is substituted with I; and K at position 408 is substituted with Q.

"Polypeptide R2 serotype —R6x" means an polypeptide comprising the amino acid sequences from position 16 to position 444 of the N-terminal truncate of Choline Binding Protein A (CbpA) serotype R6x which has the following sequence:
ENEGSTQAATSSNMAKTEHRKAAKQV-VDEYIEKMLREIQLDRRKHTQNVAL NIKLSAIKTKY-LRELNVLEEKSKDELPSEIKAK-LDAAFEKFKKDTLKPGEKVA EAKKKVEEAKKKAEDQKEEDRRNYPT-NTYKTLELEIAEFDVKVKEAELELVK EEAKESRNEG-TIKQAKEKVESKKAEATRLENIKTDRK-KAEEEAKRKADAKLK EANVATSDQGKPKGRAKRGVPGELATPD-KKENDAKSSDSSVGEETLPSSSLK SGKKVAE-AEKKVEEAEKKAKDQKEEDRRNYPT-NTYKTLDLEIAESDVKVKE AELELVKEE-AKEPRDEEKIKQAKAKVESKKAEATR-LENIKTDRKKAEEEAKR KAAEEDKVKEKPA (SEQ ID NO 7)

The DNA sequence which encodes polypeptide R2 serotype R6x:
GAAAACGAAGGAAGTACCCAAGCAGC-CACTTCTTCTAATATGGCAAAGAC AGAACATAG-GAAAGCTGCTAAACAAGTCGTCGAT-GAATATATAGAAAAA ATGTTGAGGGAGATTCAACTAGATAGAA-GAAAACATACCCAAAATGTCGC CTTAAACAT-AAAGTTGAGCGCAATTAAAACGAAG-TATTTGCGTGAATTAA ATGTTTTAGAAGAGAAGTCGAAAGAT-GAGTTGCCGTCAGAAATAAAAGCA AAGTTAGACG-CAGCTTTTGAGAAGTTTAAAAAAGATA-CATTGAAACCAGG AGAAAAGGTAGCAGAAGCTAAGAAGAAG-GTTGAAGAAGCTAAGAAAAAA GCCGAGGAT-CAAAAAGAAGAAGATCGTCGTAACTAC-CCAACCAATACTTA CAAAACGCTTGAACTTGAAATTGCT-GAGTTCGATGTGAAAGTTAAAGAAG CGGAGCT-TGAACTAGTAAAAGAGGAAGCTAAA-GAAtCTCGAAACGAGGGC ACAATTAAGCAAGCAAAAGAGAAAGT-TGAGAGTAAAAAAGCTGAGGCTA CAAGGTTA-GAAAACAtCAAGACAGAtCGTAAAAAAG-CAGAAGAAGAAGCT AAACGAAAAGCAGATGCTAAGTTGAAG-GAAGCTAATGTAGCGACTTCAG AtCAAGGTAAAC-CAAAGGGGCGGGCAAAACGAGGAGTTC-CTGGAGAGCTA GCAACACCTGATAAAAAAGAAAATGAT-
GCGAAGTCTTCAGATTCTAGCGT AGGTGAA-
GAAACTCTTCCAAGCTCATCCCTGAAAT-
CAGGAAAAAAGGTAG
CAGAAGCTGAGAAGAAGGTTGAA-
GAAGCTGAGAAAAAAGCCAAGGATCA AAAAGAA-
GAAGATCGCCGTAACTACCCAAC-
CAATACTTACAAAACGCTTG
ACCTTGAAATTGCTGAGTCCGATGT-
GAAAGTTAAAGAAGCGGAGCTTGAA CTAGTAAAA-
GAGGAAGCTAAGGAACCTCGAGACGAG-
GAAAAAATTAAGC
AAGCAAAAGCGAAAGTTGAGAG-
TAAAAAAGCTGAGGCTACAAGGTTAGA AAACAT-
CAAGACAGATCGTAAAAAAGCAGAAGAA-
GAAGCTAAACGAAAA
GCAGCAGAAGAAGATAAAGTTAAAA-
GAAAAACCAGCTG (SEQ ID NO 17)

Amino acid sequence of CbpA of serotype R6x:
ENEGSTQAATSSNMAKTEHRKAAKQV-
VDEYIEKMLREIQLDRRKHTQNVAL NIKLSAIKTKY-
LRELNVLEEKSKDELPSEIKAK-
LDAAFEKFKKDTLKPGEKVA
EAKKKVEEAKKKAEDQKEEDRRNYPT-
NTYKTLELEIAEFDVKVKEAELELVK EEAKESRNEG-
TIKQAKEKVESKKAEATRLENIKTDRK-
KAEEEAKRKADAKLK
EANVATSDQGKPKGRAKRGVPGELATPD-
KKENDAKSSDSSVGEETLPSSSLK SGKKVAE-
AEKKVEEAEKKAKDQKEEDRRNYPT-
NTYKTLDLEIAESDVKVKE
AELELVKEE-
AKEPRDEEKIKQAKAKVESKKAEATR-
LENIKTDRKKAEEEAKR KAAEEDKVKEKPAEQPQ-
PAPATQPEKPAPKPEKPAEQPKAEKTDDQQAEEDY
ARRSEEEYNRLTQQQPPKTEKPAQPSTP-
KTGWKQENGMWYFYNTDGSMATG WLQNNGSW-
YYLNANGAMATGWLQNNGSWYYLNANGS-
MATGWLQNNGS
WYYLNANGAMATGWLQYNGSWYYLNSN-
GAMATGWLQYNGSWYYLNAN GDMATGWLQNNG-
SWYYLNANGDMATGWLQYNGSWYYL-
NANGDMATGW
VKDGDTWYYLEASGAMKASQWFKVSDKW-
YYVNGSGALAVNTTVDGYGV NANGEWVN (SEQ ID NO 8).

DNA sequence encoding the amino acid sequence of the CbpA of serotype R6x:
GAAAACGAAGGAAGTACCCAAGCAGC-
CACTTCTTCTAATATGGCAAAGAC AGAACATAG-
GAAAGCTGCTAAACAAGTCGTCGAT-
GAATATATAGAAAA
ATGTTGAGGGAGATTCAACTAGATAGAA-
GAAAACATACCCAAAATGTCGC CTTAAACAT-
AAAGTTGAGCGCAATTAAAACGAAG-
TATTTGCGTGAATTAA
ATGTTTTAGAAGAGAAGTCGAAAGAT-
GAGTTGCCGTCAGAAATAAAAGCA AAGTTAGACG-
CAGCTTTTGAGAAGTTTAAAAAAGATA-
CATTGAAACCACG
AGAAAAGGTAGCAGAAGCTAAGAAGAAG-
GTTGAAGAAGCTAAGAAAAAA GCCGAGGAT-
CAAAAAGAAGAAGATCGTCGTAACTAC-
CCAACCAATACTTA
CAAAACGCTTGAACTTGAAATTGCT-
GAGTTCGATGTGAAAGTTAAAGAAG CGGAGCT-
TGAACTAGTAAAAGAGGAAGCTAAA-
GAAtCTCGAAACGAGGGC
ACAATTAAGCAAGCAAAAGAGAAAGT-
TGAGAGTAAAAAAGCTGAGGCTA CAAGGTTA-
GAAAACAtCAAGACAGAtCGTAAAAAAG-
CAGAAGAAGAAGCT
AAACGAAAAGCAGATGCTAAGTTGAAG-
GAAGCTAATGTAGCGACTtCAGAt CAAGGTAAAC-
CAAAGGGGCGGGCAAAACGAGGAGTTC-
CTGGAGAGCTAG
CAACACCTGATAAAAAAGAAAATGATGC-
GAAGTCTTCAGATTCTAGCGTA GGTGAA-
GAAACTCTTCCAAGCTCATCCCTGAAAT-
CAGGAAAAAAGGTAGC
AGAAGCTGAGAAGAAGGTTGAAGAAGCT-
GAGAAAAAAGCCAAGGATCAA AAGAAGAA-
GATCGCCGTAACTACCCAACCAATACT-
TACAAAACGCTTGA
CCTTGAAATTGCTGAGTCCGATGT-
GAAAGTTAAAGAAGCGGAGCTTGAAC TAGTAAAA-
GAGGAAGCTAAGGAACCTCGAGACGAG-
GAAAAAATTAAGCA
AGCAAAAGCGAAAGTTGAGAG-
TAAAAAAGCTGAGGCTACAAGGTTAGAA AACAT-
CAAGACAGATCGTAAAAAAGCAGAAGAA-
GAAGCTAAACGAAAAG
CAGCAGAAGAAGATAAAGTTAAA-
GAAAAACCAGCTGAACAACCACAACC AGCGCCG-
GCTACTCAACCAGAAAACCAGCTC-
CAAAACCAGAGAAGCCA
GCTGAACAACCAAAAGCAGAAAAAACA-
GATGATCAACAAGCTGAAGAAG ACTATGCTCGTA-
GATCAGAAGAAGAATATAATCGCT-
TGACTCAACAGCAA
CCGCCAAAAACTGAAAAACCAGCACAAC-
CATCTACTCCAAAAACAGGCTG GAAACAA-
GAAAACGGTATGTGGTACTTCTA-
CAATACTGATGGTTCAATGG
CAACAGGATGGCTCCAAAACAACGGT-
TCATGGTACTATCTAAACGCTAAT GGTGCTATGGC-
GACAGGATGGCTCCAAAACAATGGT-
TCATGGTACTATCT
AAACGCTAATGGTTCAATGGCAACAG-
GATGGCTCCAAAACAATGGTTCAT GGTACTAC-
CTAAACGCTAATGGTGCTATGGCGACAG-
GATGGCTCCAATAC
AATGGTTCATGGTACTACCTAAACAG-
CAATGGCGCTATGGCGACAGGATG GCTCCAATA-
CAATGGCTCATGGTACTACCT-
CAACGCTAATGGTGATATGG
CGACAGGATGGCTCCAAAACAACGGT-
TCATGGTACTACCTCAACGCTAAT GGTGATATGGC-
GACAGGATGGCTCCAATACAACGGT-
TCATGGTATTACCT
CAACGCTAATGGTGATATGGCGACAGGT-
TGGGTGAAAGATGGAGATACCT GGTACTATCT-
TGAAGCATCAGGTGCTATGAAAGCAAGC-
CAATGGTTCAAA
GTATCAGATAAATGGTACTATGTCAATG-
GCTCAGGTGCCCTTGCAGTCAAC ACAACTGTA-
GATGGCTATGGAGTCAATGCCAATGGT-
GAATGGGTAAACTAA (SEQ ID NO 18).

Polypeptide R1 Serotype R6x" means an polypeptide comprising the amino acid sequences from position 16 to position 321 of the N-terminal truncate/truncate of choline binding protein A (CbpA) serotype R6x which has the following sequence:
ENEGSTQAATSSNMAKTEHRKAAKQV-
VDEYIEKMLREIQLDRRKHTQNVAL NIKLSAIKTKY- LRELNVLEEKSKDELPSEIKAK-
LDAAFEKFKKDTLKPGEKVA
EAKKKVEEAKKKAEDQKEEDRRNYPT-
NTYKTLELEIAEFDVKVKEAELELVK EEAKESRNEG-
TIKQAKEKVESKKAEATRLENIKTDRK-
KAEEEAKRKADAKLK
EANVATSDQGKPKGRAKRGVPGELATPD-
KKENDAKSSDSSVGEETL (SEQ ID NO 9).

The DNA sequence which encodes polypeptide R1 is:
GAAAACGAAGGAAGTACCCAAGCAGC-
CACTTCTTCTAATATGGCAAAGAC AGAACATAG-
GAAAGCTGCTAAACAAGTCGTCGAT-
GAATATATAGAAAAA
ATGTTGAGGGAGATTCAACTAGATAGAA-
GAAAACATACCCAAAATGTCGC CTTAAACAT-
AAAGTTGAGCGCAATTAAAACGAAG-
TATTTGCGTGAATTAA
ATGTTTTAGAAGAGAAGTCGAAAGAT-
GAGTTGCCGTCAGAAATAAAAGCA AAGTTAGACG-
CAGCTTTTGAGAAGTTTAAAAAAGATA-
CATTGAAACCAGG
AGAAAAGGTAGCAGAAGCTAAGAAGAAG-
GTTGAAGAAGCTAAGAAAAAA GCCGAGGAT-
CAAAAAGAAGAAGATCGTCGTAACTAC-
CCAACCAATACTTA
CAAAACGCTTGAACTTGAAATTGCT-
GAGTTCGATGTGAAAGTTAAAGAAG CGGAGCT-
TGAACTAGTAAAAGAGGAAGCTAAA-
GAATCTCGAAACGAGGG
CACAATTAAGCAAGCAAAAGAGAAAGT-
TGAGAGTAAAAAAGCTGAGGCT ACAAGGTTA-
GAAAACAtCAAGACAGATCGTAAAAAAG-
CAGAAGAAGAAG
CTAAACGAAAAGCAGATGCTAAGT-
TGAAGGAAGCTAATGTAGCGACTTCA GATCAAGG-
TAAACCAAAGGGGCGGGCAAAACGAG-
GAGTTCCTGGAGAGC
TAGCAACACCTGATAAAAAAGAAAAT-
GATGCGAAGTCTTCAGATTCTAGC GTAGGTGAA-
GAAACTCTTC (SEQ ID NO 19).

"Polypeptide C/R2 serotype R6x" means an polypeptide comprising a repeat region C within R2 (see FIG. 2), wherein the repeat region C has the amino acid sequences from position 327 to position 433 of the N-terminal of choline binding protein A (CbpA) serotype R6x which has the following sequence:
KSGKKVAEAEKKVEEAEKKAKDQ-
KEEDRRNYPTNTYKTLDLEIAESDVKVK EAELELV-
KEEAKEPRDEEKIKQAKAKVESKKAE-
ATRLENIKTDRKKAEEEAK RKA (SEQ ID NO 10)

The DNA sequence of polypeptide C/R2 serotype R6x:
AAATCAGGAAAAAGGTAGCAGAAGCT-
GAGAAGAAGGTTGAAGAAGCTG AGAAAAAAGC-
CAAGGATCAAAAAGAAGAAGATCGCCG-
TAACTACCCAAC
CAATACTTACAAAACGCTTGACCT-
TGAAATTGCTGAGTCCGATGTGAAAG TTAAA-
GAAGCGGAGCTTGAACTAGTAAAAGAG-
GAAGCTAAGGAACCTCG
AGACGAGGAAAAAATTAAGCAAG-
CAAAAGCGAAAGTTGAGAGTAAAAAA GCTGAG-
GCTACAAGGTTAGAAAACATCAAGACA-
GATCGTAAAAAGCAG
AAGAAGAAGCTAAACGAAAAGCA (SEQ ID NO 20).

Polypeptide A/R2 serotype R6x" means an polypeptide comprising a repeat region A within R2 (see FIG. 2), wherein the repeat region A has the amino acid sequences from position 155 to position 265 of the N-terminal of choline binding protein A (CbpA) serotype R6X which has the following sequence:
PGEKVAEAKKKVEEAKKKAEDQ-
KEEDRRNYPTNTYKTLELEIAEFDVKVKE AELELV-
KEEAKESRNEGTIKQAKEKVESKKAE-
ATRLENIKTDRKKAEEEAKR KADA (SEQ ID NO 11)

The DNA sequence which encodes the polypeptide A/R2 serotype R6x is:
CCAGGAGAAAAGGTAGCAGAAGCTAA-
GAAGAAGGTTGAAGAAGCTAAGA AAAAAGC-
CGAGGATCAAAAAGAAGAAGATCGTCG-
TAACTACCCAACCAA
TACTTACAAAACGCTTGAACTTGAAAT-
TGCTGAGTTCGATGTGAAAGTTAA AGAAGCG-
GAGCTTGAACTAGTAAAAGAG-
GAAGCTAAAGAAtCTCGAAACG
AGGGCACAATTAAGCAAGCAAAA-
GAGAAAGTTGAGAGTAAAAAAGCTGA GGCTA-
CAAGGTTAGAAAACAtCAAGACAGATCG-
TAAAAAAGCAGAAGAA
GAAGCTAAACGAAAAGCAGATGCT (SEQ ID NO 21).

This invention is directed to an isolated polypeptide, wherein the isolated polypeptide consists of the amino acid sequence as set forth in SEQ ID NOS 22 or 23, including fragments, mutants, variants, or analogs, or derivatives, thereof.
SPSLKPEKKVAEAEKKVEEAKKKAEDQ-
KEEDRRNYPTNTYKTLELEIAESDV EVKKAELELV-
KEEAKEPRNEEKVKQAKAEVESKKAE-
ATRLEKIKTDRKKAEE EAKRKAAEEDKVKEKPA (SEQ ID NO 22; serotype 4; position 323–434); or PSSS-
LKSGKKVAEAEKKVEEAEKKAKDQ-
KEEDRRNYPTNTYKTLDLEIAESD VKVKEAELELV-
KEEAKEPRDEEKIKQAKAKVESKKAEATRLENIKTD RKKAE EEAKRKAAEEDKVKEKRA (SEQ ID NO 23, serotype R6x; position 322–434).

"Polypeptide B/R2" means a polypeptide comprising the amino acid sequences from position 270 to position 326 of the N-terminal truncate of choline binding protein A (CbpA) serotype type 4 as set forth in FIG. 2. "Polypeptide B/R2 serotype —R6x" means an polypeptide comprising the amino acid sequences from position 264 to position 326 of the N-terminal truncate of Choline Binding Protein A (CbpA) serotype R6x as set forth in FIG. 2. This invention contemplates a polypeptide having the amino acid sequence of regions A, B, C, A+B, B+C, A+C as shown in FIG. 1.

Further, this invention provides an isolated polypeptide comprising an amino acid sequence of a N-terminal choline binding protein A truncate, wherein the polypeptide has the amino acid KXXE (SEQ ID NO 6).

This invention is directed to a polypeptide comprising an amino acid sequence of a N-terminal choline binding protein A truncate, wherein the amino acid sequence is set forth in FIG. 2. In one embodiment, the polypeptide has an amino acid sequence which is a conserved region as set forth in FIG. 2. For example, conserved regions include but are not limited to amino acid sequence 158 to 172; 300 to 321; 331 to 339; 355 to 365; 367 to 374; 379 to 389; 409 to 427; and 430 to 447 FIG. 2 sets forth homologies of various serotypes of the nucleic acid and amino acid sequence of the N-terminal region of CbpA which are contemplated by this invention.

This invention provides an isolated polypeptide comprising an amino acid sequence of a N-terminal choline binding protein A truncate, wherein the polypeptide has lectin activity and does not bind to choline. In one embodiment the polypeptide has the amino acid sequence as set forth in any of SEQ ID NO 1, 3–5, 7, or 9–11 including fragments, mutants, variants, analogs, or derivatives, thereof.

As used herein, "a polypeptide having a lectin activity" means a polypeptide, peptide or protein which binds non-covalently to a carbohydrate. As defined herein, "adhesin" means noncovalent binding of a bacteria to a human cell or secretion that is stable enough to withstand washing. As defined herein, "binds to the LNnT means binds to Lacto-N-neotetraose coated substrates more than albumin-control.

This invention provides an isolated immunogenic polypeptide comprising an amino acid sequence of a N-terminal choline binding protein A truncate. It is contemplated by this invention that the immunogenic polypeptide has the amino acid In one embodiment the polypeptide has the amino acid sequence as set forth in any of SEQ ID NOS 1, 3–7, or 9–11, including fragments, mutants, variants, analogs, or derivatives, thereof. This invention provides an isolated polypeptide comprising an amino acid sequence of a N-terminal choline binding protein A truncate as set forth in FIG. 2. In one embodiment, the polypeptide has an amino acid sequence which is a conserved region as set forth in FIG. 2.

This invention is directed to analogs of the polypeptide which comprise the amino acid sequence as set forth above. The analog polypeptide may have an N-terminal methionine or an N-terminal polyhistidine optionally attached to the N or COOH terminus of the polypeptide which comprise the amino acid sequence.

In another embodiment, this invention contemplates peptide fragments of the polypeptide which result from proteolytic digestion products of the polypeptide. In another embodiment, the derivative of the polypeptide has one or more chemical moieties attached thereto. In another embodiment the chemical moiety is a water soluble polymer. In another embodiment the chemical moiety is polyethylene glycol. In another embodiment the chemical moiety is mon-, di-, tri- or tetrapegylated. In another embodiment the chemical moiety is N-terminal monopegylated.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicty and antigenicity of heterologous compounds. For example, a PEG adduct of a human protein might be useful for the treatment of disease in other mammalian species without the risk of triggering a severe immune response. The compound of the present invention may be delivered in a microencapsulation device so as to reduce or prevent an host immune response against the compound or against cells which may produce the compound. The compound of the present invention may also be delivered microencapsulated in a membrane, such as a liposome.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

In one embodiment, the amino acid residues of the polypeptide described herein are preferred to be in the "L" isomeric form. In another embodiment, the residues in the "D" isomeric form can be substituted for any L-amino acid residue, as long as the desired functional property of lectin activity is retained by the polypeptide. $NH_2$ refers to the free amino group present at the amino terminus of a polypeptide. COOH refers to the free carboxy group present at the carboxy terminus of a polypeptide. Abbreviations used herein are in keeping with standard polypeptide nomenclature, J. Biol. Chem., 243:3552–59(1969).

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

Synthetic polypeptide, prepared using the well known techniques of solid phase, liquid phase, or peptide condensation techniques, or any combination thereof, can include natural and unnatural amino acids. Amino acids used for peptide synthesis may be standard Boc ($N^\alpha$-amino protected $N^\alpha$-t-butyloxycarbonyl) amino acid resin with the standard deprotecting, neutralization, coupling and wash protocols of the original solid phase procedure of Merrifield (1963, J. Am. Chem. Soc. 85:2149–2154), or the base-labile $N^\alpha$-amino protected 9-fluorenylmethoxycarbonyl (Fmoc) amino acids first described by Carpino and Han (1972, J. Org. Chem. 37:3403–3409). Thus, polypeptide of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In one aspect of the invention, the peptides may comprise a special amino acid at the C-terminus which incorporates either a $CO_2H$ or $CONH_2$ side chain to simulate a free glycine or a glycine-amide group. Another way to consider this special residue would be as a D or L amino acid analog with a side chain consisting of the linker or bond to the bead. In one embodiment, the pseudo-free C-terminal residue may be of the D or the L optical configuration; in another embodiment, a racemic mixture of D and L-isomers may be used.

In an additional embodiment, pyroglutamate may be included as the N-terminal residue of the peptide. Although pyroglutamate is not amenable to sequence by Edman degradation, by limiting substitution to only 50% of the peptides on a given bead with N-terminal pyroglutamate, there will remain enough non-pyroglutamate peptide on the bead for sequencing. One of ordinary skill would readily recognize that this technique could be used for sequencing of any peptide that incorporates a residue resistant to Edman degradation at the N-terminus. Other methods to characterize individual peptides that demonstrate desired activity are described in detail infra. Specific activity of a peptide that comprises a blocked N-terminal group, e.g., pyroglutamate, when the particular N-terminal group is present in 50% of the peptides, would readily be demonstrated by comparing activity of a completely (100%) blocked peptide with a non-blocked (0%) peptide.

In addition, the present invention envisions preparing peptides that have more well defied structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity (Hruby, 1982, Life Sciences 31:189–199; Hruby et at., 1990, Biochem J. 268:249–262); the present invention provides a method to produce a constrained peptide that incorporates random sequences at all other positions.

A constrained, cyclic or rigidized peptide may be prepared synthetically, provided that in at least two positions in the sequence of the peptide an amino acid or amino acid analog is inserted that provides a chemical functional group capable of cross-linking to constrain, cyclise or rigidize the peptide after treatment to form the cross-link. Cyclization will be favored when a turn-inducing amino acid is incorporated. Examples of amino acids capable of cross-linking a peptide are cysteine to form disulfide, aspartic acid to form a lactone or a lactase, and a chelator such as y-carboxyl-glutamic acid (Gla) (Bachem) to chelate a transition metal and form a cross-link. Protected γ-carboxyl glutamic acid may be prepared by modifying the synthesis described by Zee-Cheng and Olson (1980, Biophys. Biochem. Res. Commun. 94:1128–1132). A peptide in which the peptide sequence comprises at least two amino acids capable of cross-linking may be treated, e.g., by oxidation of cysteine residues to form a disulfide or addition of a metal ion to form a chelate, so as to cross-link the peptide and form a constrained, cyclic or rigidized peptide.

The present invention provides strategies to systematically prepare cross-links. For example, if four cysteine residues are incorporated in the peptide sequence, different protecting groups may be used (Hiskey, 1981, in The Peptides: Analysis, Synthesis, Biology, Vol. 3, Gross and Meienhofer, eds., Academic Press: New York, pp. 137–167; Ponsanti et al., 1990, Tetrahedron 46:8255–8266). The first pair of cysteine may be deprotected and oxidized, then the second set may be deprotected and oxidized. In this way a defined set of disulfide cross-links may be formed. Alternatively, a pair of cysteine and a pair of collating amino acid analogs may be incorporated so that the cross-links are of a different chemical nature.

The following non-classical amino acids may be incorporated in the peptide in order to introduce particular conformational motifs: 1,2,3,4-tetrahydroisoquinoline-3-carboxylate (Kazmierski et al., 1991, J. Am. Chem. Soc. 113:2275–2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby, 1991, Tetrahedron Lett.); 2-aminotetrahydronaphthalene-2-carboxylic acid (Landis, 1989, Ph.D. Thesis, University of Arizona); hydroxy-1,2,3,4-tetrahydroisoquinoline-3-carboxylate (Miyake et al., 1989, J. Takeda Res. Labs. 43:53–76); β-carboline (D and L) (Kazmierski, 1988, Ph.D. Thesis, University of Arizona); HIC (histidine isoquinoline carboxylic acid) (Zechel et al., 1991, Int. J. Pep. Protein Res. 43); and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al., 1985, J. Org. Chem. 50:5834–5838); β-sheet inducing analogs (Kemp et al., 1988, Tetrahedron Lett. 29:5081–5082); β-turn inducing analogs (Kemp et al., 1988, Tetrahedron Lett. 29:5057–5060); α-helix inducing analogs (Kemp et al., 1988, Tetrahedron Lett. 29:4935–4938); γ-turn inducing analogs (Kemp et al., 1989, J. Org. Chem. 54:109:115); and analogs provided by the following references: Nagai and Sato, 1985, Tetrahedron Lett. 26:647–650; DiMaio et al., 1989, J. Chem. Soc. Perkin Trans. p. 1687; also a Gly-Ala turn analog (Kahn et al., 1989, Tetrahedron Lett. 30:2317); amide bond isostere (Jones et al., 1988, Tetrahedron Lett. 29:3853–3856); tretrazol (Zabrocki et al., 1988, J. Am. Chem. Soc. 110:5875–5880); DTC (Samanen et al., 1990, Int. J. Protein Pep. Res. 35:501:509); and analogs taught in Olson et al., 1990, J. Am. Chem. Sci. 112:323–333 and Garvey et al., 1990, J. Org. Chem. 56:436. Conformationally restricted mimetics of beta turns and beta bulges, and peptides containing them, are described in U.S. Pat. No. 5,440,013, issued Aug. 8, 1995 to Kahn.

The present invention further provides for modification or derivatization of the polypeptide or peptide of the invention. Modifications of peptides are well known to one of ordinary skill, and include phosphorylation, carboxymethylation, and acylation. Modifications may be effected by chemical or enzymatic means. In another aspect, glycosylated or fatty acylated peptide derivatives may be prepared. Preparation of glycosylated or fatty acylated peptides is well known in the art. Fatty acyl peptide derivatives may also be prepared. For example, and not by way of limitation, a free amino group (N-terminal or lysyl) may be acylated, e.g., myristoylated. In another embodiment an amino acid comprising an aliphatic side chain of the structure —$(CH_2)_n CH_3$ may be incorporated in the peptide. This and other peptide-fatty acid conjugates suitable for use in the present invention are disclosed in U.K. Patent GB-8809162.4, International Patent Application PCT/AU89/00166, and reference 5, supra.

Mutations can be made in a nucleic acid encoding the polypeptide such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutanic acid. Such alterations will not be expected to affect apparent molecular weight as determined by polyacrylamide gel electrophoresis, or isoelectric point. Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Synthetic DNA sequences allow convenient construction of genes which will express analogs or "muteins". A general method for site-specific incorporation of unnatural amino acids into proteins is described in Noren, et al. *Science,* 244:182–188 (April 1989). This method may be used to create analogs with unnatural amino acids.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

In an additional embodiment, pyroglutamate may be included as the N-terminal residue of the peptide. Although pyroglutamate is not amenable to sequence by Edman degradation, by limiting substitution to only 50% of the peptides on a given bead with N-terminal pyroglutatamate, there will remain enough non-pyroglutamate peptide on the bead for sequencing. One of ordinary skill in would readily recognize that this technique could be used for sequencing of any peptide that incorporates a residue resistant to Edman degradation at the N-terminus. Other methods to characterize individual peptides that demonstrate desired activity are described in detail infra. Specific activity of a peptide that comprises a blocked N-terminal group, e.g., pyroglutamate, when the particular N-terminal group is present in 50% of the peptides, would readily be demonstrated by comparing activity of a completely (100%) blocked peptide with a non-blocked (0%) peptide.

Chemical Moieties For Derivatization. Chemical moieties suitable for derivatization may be selected from among water soluble polymers. The polymer selected should be water soluble so that the component to which it is attached does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/component conjugate will be used therapeutically, and if so, the desired dosage, circulation time, resistance to proteolysis, and other considerations. For the present component or components, these may be ascertained using the assays provided herein.

The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols and polyvinyl alcohol. Polyethylene glycol propionaldenhyde may have advantages in manufacturing due to its stability in water.

The polymer may be of any molecular weight, and may be branched or unbranched. For polyethylene glycol, the preferred molecular weight is between about 2 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to component or components molecules will vary, as will their concentrations in the reaction mixture. In general, the optimum ratio (in terms of efficiency of reaction in that there is no excess unreacted component or components and polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the component or components with consideration of effects on functional or antigenic domains of the protein. There are a number of attachment methods available to those skilled in the art, e.g., EP 0 401 384 herein incorporated by reference (coupling PEG to G-CSF), see also Malik et al., 1992, Exp. Hematol. 20.1028–1035 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group include lysine residues and the—terminal amino acid residues; those having a free carboxyl group include aspartic acid residues glutamic acid residues and the C-terminal amino acid residue. Sulfhydrl groups may also be used as a reactive group for attaching the polyethylene glycol molecule(s). Preferred for therapeutic purposes is attachment at an amino group, such as attachment at the N-terminus or lysine group.

This invention provides an isolated nucleic acid encoding a polypeptide comprising an amino acid sequence of a N-terminal choline binding protein A truncate. This invention provides an isolated nucleic acid encoding a polypeptide comprising an amino acid sequence of a N-terminal choline binding protein A truncate as set forth in FIG. 2. In one embodiment the nucleic acid is set forth in any of SEQ ID NOS 12, 14–17, or 19–21, including fragments, mutants, variants, analogs, or derivatives, thereof. The nucleic acid is DNA, cDNA, genomic DNA, RNA. Further, the isolated nucleic acid may be operatively linked to a promoter of RNA transcription. It is contemplated that the nucleic acid is used to competitively inhibit the lectin activity.

A "vector" is a replicon, such as plasmid, phage or cosmid, to which another DNA segment may be attached so as to bring about the replication of the attached segment.

A "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

Further this invention also provides a vector which comprises the above-described nucleic acid molecule. The promoter may be, or is identical to, a bacterial, yeast, insect or mammalian promoter. Further, the vector may be a plasmid, cosmid, yeast artificial chromosome (YAC), bacteriophage or eukaryotic viral DNA.

Other numerous vector backbones known in the art as useful for expressing protein may be employed. Such vectors include, but are not limited to: adenovirus, simian virus 40 (SV40), cytomegalovirus (CMV), mouse mammary tumor virus (MMTV), Moloney murine leukemia virus, DNA delivery systems, i.e. liposomes, and expression plasmid delivery systems. Further, one class of vectors comprises DNA elements derived from viruses such as bovine papilloma virus, polyoma virus, baculovirus, retroviruses or Semliki Forest virus. Such vectors may be obtained commercially or assembled from the sequences described by methods well-known in the art.

This invention also provides a host vector system for the production of a polypeptide which comprises the vector of a suitable host cell. Suitable host cells include, but are not limited to, prokaryotic or eukaryotic cells, e.g. bacterial cells (including gram positive cells), yeast cells, fungal cells, insect cells, and animals cells. Numerous mammalian cells may be used as hosts, including, but not limited to, the mouse fibroblast cell NIH 3T3, CHO cells, HeLa cells, Ltk cells, Cos cells, etc.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

This invention further provides a method of producing a polypeptide which comprises growing the above-described host vector system under suitable conditions permitting the production of the polypeptide and recovering the polypeptide so produced.

This invention further provides an antibody capable of specifically recognizing or binding to the isolated polypeptide. The antibody may be a monoclonal or polyclonal antibody. Further, the antibody may be labeled with a detectable marker that is either a radioactive, colorimetric, fluorescent, or a luminescent marker. The labeled antibody may be a polyclonal or monoclonal antibody. In one embodiment, the labeled antibody is a purified labeled antibody. Methods of labeling antibodies are well known in the art.

The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. Such antibodies include but are not limited to polyclonal, monoclonal, chimeric, single chain, Fab fragments, and an Fab expression library.

Various procedures known in the art may be used for the production of polyclonal antibodies to polypeptide or derivatives or analogs thereof (see, e.g., *Antibodies—A Laboratory Manual*, Harlow and Lane, eds., Cold Spring Harbor Laboratory Press: Cold Spring Harbor, Ne York, 1988). For the production of antibody, various host animals can be immunized by injection with the truncated CbpA, or a derivative (e g., fragment or fusion protein) thereof, including but not limited to rabbits, mice, rats, sheep, goats, etc. In one embodiment, the polypeptide can be conjugated to an immunogenic carrier, e.g., bovine serum albumin (BSA) or keyhole limpet hemocyanin (KLH). Various adjuvant may be used to increase the immunological response, depending on the host species.

For preparation of monoclonal antibodies, or fragment, analog, or derivative thereof, any technique that provides for the production of antibody molecules by continuous cell lines in culture may be used (see, e.g., *Antibodies—A Laboratory Manual*, Harlow and Lane, eds., Cold Spring Harbor Laboratory Press: Cold Spring Harbor, Ne York, 1988). These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, J. Bacteriol. 159–870; Neuberger et al., 1984, Nature 312:604–608; Takeda et al., 1985, Nature 314:452–454) by splicing the genes from a mouse antibody molecule specific for a polypeptide together with genes from a human antibody molecule of appropriate biological activity can be used; such antibodies are within the scope of this invention.

Such human or humanized chimeric antibodies are preferred for use in therapy of human diseases or disorders (described infra), since the human or humanized antibodies are much less likely than xenogenic antibodies to induce an immune response, in particular an allergic response, themselves. An additional embodiment of the invention utilizes the techniques described for the construction of Fab expression libraries (Huse et al., 1989, Science 246:1275–1281) to allow rapid and easy identification of monoclonal Fab fragments with the desired specificity for the polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Antibodies can be labeled for detection in vitro, e.g., with labels such as enzymes, fluorophores, chromophores, radioisotopes, dyes, colloidal gold, latex particles, and chemiluminescent agents. Alternatively, the antibodies can be labeled for detection in vivo, e.g., with radioisotopes (preferably technetium or iodine); magnetic resonance shift reagents (such as gadolinium and manganese); or radioopaque reagents.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The polypeptide can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}CO$. $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

In a further embodiment of this invention, commercial test kits suitable for use by a medical specialist may be prepared to determine the presence or absence of predetermined binding activity or predetermined binding activity capability to suspected target cells. In accordance with the testing techniques discussed above, one class of such kits will contain at least the labeled polypeptide or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for predetermined bacterial binding activity, comprising:

(a) a predetermined amount of at least one labeled immunochemically reactive component obtained by the direct or indirect attachment of the present the polypeptide or a specific binding partner thereto, to a detectable label;

(b) other reagents; and (c) directions for use of said kit.

This invention provides antagonist or blocking agents which include but are not limited to: peptide fragments, mimetic, a nucleic acid molecule, a ribozyme, a polypeptide, a small molecule, a carbohydrate molecule, a monosaccharide, an oligosaccharide or an antibody. Also, agents which competitively block or inhibit pneumococcal bacterium are contemplmated by this invention. This invention provides an agent which comprises an inorganic compound, a nucleic acid molecule, an oligonucleotide, an organic compound, a peptide, a peptidomimetic compound, or a protein which inhibits the polypeptide.

This invention provides a vaccine which comprises the polypeptide having the amino acid sequence as set forth in any of SEQ ID NOS: 1, 3–7, 9–11, 22, and 23 and a pharmaceutically acceptable adjuvant or carrier. The polypeptide may comprise an amino acid sequence of a N-terminal choline binding protein A truncate as set forth in FIG. 2. This invention provides a vaccine which comprises the polypeptide having the amino acid sequence which comprises a conserved region as set forth in FIG. 2 and a pharmaceutically acceptable adjuvant or carrier. For example, conserved regions include but are not limited to amino acid sequence 158 to 172; 300 to 321; 331 to 339; 355 to 365; 367 to 374; 379 to 389; 409 to 427; and 430 to 447. This invention provides a vaccine comprising the isolated nucleic acid encoding the polypeptide and a pharmaceutically acceptable adjuvant or carrier.

Active immunity against Gram positive bacteria, particularly *pneumococcus*, can be induced by immunization (vaccination) with an immunogenic amount of the polypeptide, or peptide derivative or fragment thereof, and an adjuvant, wherein the polypeptide, or antigenic derivative or fragment thereof, is the antigenic component of the vaccine.

The present invention, or fragments thereof, can be prepared in an admixture with an adjuvant to prepare a vaccine. Preferably, the derivative or fragment thereof, used as the antigenic component of the vaccine is an adhesin. More preferably, the polypeptide or peptide derivative or fragment thereof, used as the antigenic component of the vaccine is an antigen common to all or many strains of a species of Gram positive bacteria, or common to closely related species of bacteria. Most preferably, the antigenic component of the vaccine is an adhesin that is a common antigen.

Vectors containing the nucleic acid-based vaccine of the invention can be introduced into the desired host by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

The vaccine can be administered via any parenteral route, including but not limited to intramuscular, intraperitoneal, intravenous, and the like. Preferably, since the desired result of vaccination is to elucidate an immune response to the antigen, and thereby to the pathogenic organism, administration directly, or by targeting or choice of a viral vector, indirectly, to lymphoid tissues, e.g., lymph nodes or spleen, is desirable. Since immune cells are continually replicating, they are ideal target for retroviral vector-based nucleic acid vaccines, since retroviruses require replicating cells.

Passive immunity can be conferred to an animal subject suspected of suffering an infection with a Gram positive bacterium, preferably streptococcal, and more preferably pneumoccal, by administering antiserum, polyclonal antibodies, or a neutralizing monoclonal antibody against a polypeptide of the invention to the patient. Although passive immunity does not confer long term protection, it can be a valuable tool for the treatment of a bacterial infection of a subject who has not been vaccinated. Passive immunity is particularly important for the treatment of antibiotic resistant strains of Gram positive bacteria, since no other therapy may be available. Preferably, the antibodies administered for passive immune therapy are autologous antibodies. For example, if the subject is a human, preferably the antibodies are of human origin or have been "humanized," in order to minimize the possibility of an immune response against the antibodies. The active or passive vaccines of the invention, or the administration of an adhesin, can be used to protect an animal subject from infection of a Gram positive bacteria, preferably *streptococcus*, and more preferably, *pneumococcus*.

This invention provides a pharmaceutical composition comprising an amount of the polypeptide as described and a pharmaceutically acceptable carrier or diluent.

For example, such pharmaceutical composition for preventing pneumococcal attachment to mucosal surface may include antibody to lectin domain and/or soluble excess lectin domain proteins. Blocking adherence by either mechanism blocks the initial step in infection thereby reducing colonization. This in turn decreases person to person transmission and prevents development of symptomatic disease.

This invention provides a method of inducing an immune response in a subject which has been exposed to or infected with a pneumococcal bacterium comprising administering to the subject an amount of the pharmaceutical composition, thereby inducing an immune response.

This invention provides a method for preventing infection by a pneumococcal bacterium in a subject comprising administering to the subject an amount of the pharmaceutical composition effective to prevent pneumococcal bacterium attachment, thereby preventing infection by a pneumococcal bacterium.

This invention provides a method for preventing infection by a pneumococcal bacterium in a subject comprising administering to the subject an amount of a pharmaceutical composition comprising the antibody and a pharmaceutically acceptable carrier or diluent, thereby preventing infection by a pneumococcal bacterium.

This invention provides a method for treating a subject infected with or exposed to pneumococcal bacterium comprising administering to the subject a therapeutically effective amount of the vaccine, thereby treating the subject.

This invention provides a method of inhibiting colonization of host cells in a subject which has been exposed to or infected with a pneumococcal bacterium comprising administering to the subject an amount of the pharmaceutical composition comprising the polypeptide consisting of the amino acid sequence as set forth in any of SEQ ID NOS 1, 3–5, 7, or 9–11, thereby inducing an immune response. The therapeutic peptide that blocks colonization is delivered by the respiratory mucosal. The pharmaceutical composition comprising the polypeptide consisting of the amino acid sequence as set forth in FIG. 2.

As used herein, "pharmaceutical composition" could mean therapeutically effective amounts of polypeptide products of the invention together with suitable diluents, preservatives, solubilizers, emulsifiers, adjuvant and/or carriers useful in SCF (stem cell factor) therapy. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), antioxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of clearance of SCF. The choice of compositions will depend on the physical and chemical properties of the protein having SCF activity. For example, a product derived from a membrane-bound form of SCF may require a formulation containing detergent. Controlled or sustained release compositions include formulation in lipophilic depots (e.g., fatty acids, waxes, oils). Also comprehended by the invention are particulate compositions coated with polymers (e.g., poloxamers or poloxamines) and SCF coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

Further, as used herein "pharmaceutically acceptable carrier" are well known to those skilled in the art and include, but are not limited to, 0.01–0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed,* 1984, Benjamin/Cummings: Menlo Park, Calif., p. 384). Often, a primary challenge with an antigen alone, in the absence of an adjuvant, will fail to elicit a humoral or cellular immune response. Adjuvant include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (*bacille Calmette-Guerin*) and *Corynebacterium parvum*. Preferably, the adjuvant is pharmaceutically acceptable.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, compounds are often cleared rapidly from mucosal surfaces or the circulation and may therefore elicit relatively short-lived pharmacological activity. Consequently, frequent administrations of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Dosages. The sufficient amount may include but is not limited to from about 1 $\mu$g/kg to about 1000 mg/kg. The amount may be 10 mg/kg. The pharmaceutically acceptable form of the composition includes a pharmaceutically acceptable carrier.

As noted above, the present invention provides therapeutic compositions comprising pharmaceutical compositions comprising vectors, vaccines, polypeptides, nucleic acids and antibodies, anti-antibodies, and agents, to compete with the *pneumococcus* bacterium for pathogenic activities, such as adherence to host cells.

The preparation of therapeutic compositions which contain an active component is well understood in the art. Typically, such compositions are prepared as an aerosol of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An active component can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. In the context of the present invention, a deficit in the response of the host is evidenced by continuing or spreading bacterial infection. An improvement in a clinically significant condition in the host includes a decrease in bacterial load, clearance of bacteria from colonized host cells, reduction in fever or inflammation associated with infection, or a reduction in any symptom associated with the bacterial infection.

According to the invention, the component or components of a therapeutic composition of the invention may be introduced parenterally, transmucosally, e.g., orally, nasally, pulmonaraily, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. Oral or pulmonary delivery may be preferred to activate mucosal immunity; since pneumococci generally colonize the nasopharyngeal and pulmonary mucosa, mucosal immunity may be a particularly effective preventive treatment. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

In another embodiment, the active compound can be delivered in a vesicle, in particular a liposome (see Langer, Science 249:1527–1533 (1990); Treat et al., in *Liposomes in the Therapy of Infectious Disease and Cancer*, Lopez-Berestein and Fidler (eds.), Liss, New York, pp. 353–365 (1989); Lopez-Berestein, ibid., pp. 317–327; see generally ibid).

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)). Preferably, a controlled release device is introduced into a subject in proximity of the site of inappropriate immune activation or a tumor. Other controlled release systems are discussed in the review by Langer (Science 249:1527–1533 (1990)).

A subject in whom administration of an active component as set forth above is an effective therapeutic regimen for a bacterial infection is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

In the therapeutic methods and compositions of the invention, a therapeutically effective dosage of the active component is provided. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing. Generally, for intravenous injection or infusion, dosage may be lower than for intraperitoneal, intramuscular, or other route of administration. The dosing schedule may vary, depending on the circulation half-life, and the formulation used. The compositions are administered in a manner compatible with the dosage formulation in the therapeutically effective amount. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Administration with other compounds. For treatment of a bacterial infection, one may administer the present active component in conjunction with one or more pharmaceutical compositions used for treating bacterial infection, including but not limited to (1) antibiotics; (2) soluble carbohydrate inhibitors of bacterial adhesin; (3) other small molecule inhibitors of bacterial adhesin; (4) inhibitors of bacterial metabolism, transport, or transformation; (5) stimulators of bacterial lysis, or (6) anti-bacterial antibodies or vaccines directed at other bacterial antigens. Other potential active components include anti-inflammatory agents, such as steroids and non-steroidal anti-inflammatory drugs. Administration may be simultaneous (for example, administration of a mixture of the present active component and an antibiotic), or may be in seriatim.

Accordingly, in specific embodiment, the therapeutic compositions may further include an effective amount of the active component, and one or more of the following active ingredients: an antibiotic, a steroid, etc. Exemplary formulations are given below:

| Formulations | |
|---|---|
| Ingredient | mg/ml |
| Intravenous Formulation I | |
| cefotaxime | 250.0 |
| Polypeptide | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation II | |
| ampicillin | 250.0 |
| Polypeptide | 10.0 |
| sodium bisulfite USP | 3.2 |
| disodium edetate USP | 0.1 |
| water for injection q.s.a.d. | 1.0 ml |
| Intravenous Formulation III | |
| gentamicin (charged as sulfate) | 40.0 |
| Polypeptide | 10.0 |
| sodium bisulfite USP | 3.2 |
| disodium edetate USP | 0.1 |
| water for injection q.s.a.d. | 1.0 ml |

-continued

| Formulations | |
|---|---|
| Ingredient | mg/ml |
| Intravenous Formulation IV | |
| Polypeptide | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation V | |
| Polypeptide antagonist | 5.0 |
| sodium bisulfite USP | 3.2 |
| disodium edetate USP | 0.1 |
| water for injection q.s.a.d. | 1.0 ml |

Thus, in a specific instance where it is desired to reduce or inhibit the infection resulting from a bacterium mediated binding of bacteria to a host cell, or an antibody thereto, or a ligand thereof or an antibody to that ligand, the polypeptide is introduced to block the interaction of the bacteria with the host cell.

Also contemplated herein is pulmonary delivery of the present polypeptide having lectin activity which acts as adhesin inhibitory agent (or derivatives thereof), of the invention. The adhesin inhibitory agent (or derivative) is delivered to the lungs of a mammal, where it can interfere with bacterial, ie., streptococcal, and preferably pneumococcal binding to host cells. Other reports of preparation of proteins for pulmonary delivery are found in the art [Adjei et al. *Pharmaceutical Research,* 7:565–569 (1990); Adjei et al., *International Journal of Pharmaceutics,* 63:135–144 (1990) (leuprolide acetate); Braquet et al., *Journal of Cardiovascular Pharmacology,* 13(suppl. 5):143–146 (1989) (endothelin-1); Hubbard et al., *Annals of internal Medicine,* Vol. 111, pp. 206–212 (1989) (αl-antitrypsin); Smith et al., *J. Clin. Invest.* 84:1145–1146 (1989) (α-1-proteinase); Oswein et al., "Aerosolization of Proteins", *Proceedings of Symposium on Respiratory Drug Delivery II,* Keystone, Colo., March, (1990) (recombinant human growth hormone); Debs et al., *J. Immunol.* 140:3482–3488 (1988) (interferon-γ and tumor necrosis factor alpha); Platz et al., U.S. Pat. No. 5,284,656 (granulocyte colony stimulating factor)]. A method and composition for pulmonary delivery of drugs is described in U.S. Pat. No. 5,451,569, issued Sep. 19, 1995 to Wong et al.

All such devices require the use of formulations suitable for the dispensing of adhesin inhibitory agent (or derivative). Typically, each formulation is specific to the type of device employed and may involve the use of an appropriate propellant material, in addition to the usual diluents, adjuvant and/or carriers useful in therapy. Also, the use of liposomes, microcapsules or microspheres, inclusion complexes, or other types of carriers is contemplated. Chemically modified adhesin inhibitory agent may also be prepared in different formulations depending on the type of chemical modification or the type of device employed.

Formulations suitable for use with a nebulizer, either jet or ultrasonic, will typically comprise adhesin inhibitory agent (or derivative) dissolved in water at a concentration of about 0.1 to 25 mg of biologically active adhesin inhibitory agent per ml of solution. The formulation may also include a buffer and a simple sugar (e.g., for adhesin inhibitory agent stabilization and regulation of osmotic pressure). The nebulizer formulation may also contain a surfactant, to reduce or prevent surface induced aggregation of the adhesin inhibitory agent caused by atomization of the solution in forming the aerosol.

Formulations for use with a metered-dose inhaler device will generally comprise a finely divided powder containing the adhesin inhibitory agent (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

The liquid aerosol formulations contain adhesin inhibitory agent and a dispersing agent in a physiologically acceptable diluent. The dry powder aerosol formulations of the present invention consist of a finely divided solid form of adhesin inhibitory agent and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of pulmonary administration of a drug are well known in the art, and manipulation of formulations, aerosolization means and construction of a delivery device require at most routine experimentation by one of ordinary skill in the art. In a particular embodiment, the mass median dynamic diameter will be 5 micrometers or less in order to ensure that the drug particles reach the lung alveoli [Wearley, L. L., *Crit. Rev. in Ther. Drug Carrier Systems* 8:333 (1991)].

Systems of aerosol delivery, such as the pressurized metered dose inhaler and the dry powder inhaler are disclosed in Newman, S. P., *Aerosols and the Lung*, Clarke, S. W. and Davia, D. editors, pp. 197–22 and can be used in connection with the present invention.

In a further embodiment, as discussed in detail infra, an aerosol formulation of the present invention can include other therapeutically or pharmacologically active ingredients in addition to adhesin inhibitory agent, such as but not limited to an antibiotic, a steroid, a non-steroidal anti-inflammatory drug, etc.

Liquid Aerosol Formulations. The present invention provides aerosol formulations and dosage forms for use in treating subjects suffering from bacterial, e.g., streptococcal, in particularly pneumococcal, infection. In general such dosage forms contain adhesin inhibitory agent in a pharmaceutically acceptable diluent. Pharmaceutically acceptable diluents include but are not limited to sterile water, saline, buffered saline, dextrose solution, and the like. In a specific embodiment, a diluent that may be used in the present invention or the pharmaceutical formulation of the present invention is phosphate buffered saline, or a buffered saline solution generally between the pH 7.0–8.0 range, or water.

The liquid aerosol formulation of the present invention may include, as optional ingredients, pharmaceutically acceptable carriers, diluents, solubilizing or emulsifying agents, surfactants and excipients. The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure. Examples of the agents include but are not limited to salts, such as sodium chloride, or potassium chloride, and carbohydrates, such as glucose, galactose or mannose, and the like.

The present invention further contemplates liquid aerosol formulations comprising adhesin inhibitory agent and another therapeutically effective drug, such as an antibiotic, a steroid, a non-steroidal anti-inflammatory drug, etc.

Aerosol Dry Powder Formulations. It is also contemplated that the present aerosol formulation can be prepared as a dry powder formulation comprising a finely divided powder form of adhesin inhibitory agent and a dispersant.

Formulations for dispensing from a powder inhaler device will comprise a finely divided dry powder containing adhesin inhibitory agent (or derivative) and may also include a bulking agent, such as lactose, sorbitol, sucrose, or mannitol in amounts which facilitate dispersal of the powder from the device, e.g., 50 to 90% by weight of the formulation. The adhesin inhibitory agent (or derivative) should most advantageously be prepared in particulate form with an average particle size of less than 10 mm (or microns), most preferably 0.5 to 5 mm, for most effective delivery to the distal lung. In another embodiment, the dry powder formulation can comprise a finely divided dry powder containing adhesin inhibitory agent, a dispersing agent and also a bulking agent. Bulking agents useful in conjunction with the present formulation include such agents as lactose, sorbitol, sucrose, or mannitol, in amounts that facilitate the dispersal of the powder from the device.

The present invention further contemplates dry powder formulations comprising adhesin inhibitory agent and another therapeutically effective drug, such as an antibiotic, a steroid, a non-steroidal anti-inflammatory drug, etc.

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics Edited* by G. S. Banker and C. T. Rhodes Chapter 10, 1979, herein incorporated by reference. In general, the formulation will include the component or components (or chemically modified forms thereof) and inert ingredients which allow for protection against the stomach environment, and release of the biologically active material in the intestine.

Also specifically contemplated are oral dosage forms of the above derivatized component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Abducts" In: *Enzymes as Drugs*, Hocenberg and Roberts, eds., Wiley-Interscience, New York, N.Y., pp. 367–383; Newmark, et al., 1982, J. Appl. Biochem. 4:185–189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The peptide therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextran and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the polypeptide (or derivative) are for instance the fatty acids oleic acid, linoleic acid and linolenic acid.

Pulmonary Delivery. Also contemplated herein is pulmonary delivery of the present polypeptide (or derivatives thereof). The polypeptide (or derivative) is delivered to the lungs of a mammal while inhaling and coats the mucosal surface of the alveoli. Other reports of this include Adjei et al., 1990, Pharmaceutical Research, 7:565–569; Adjei et al., 1990, International Journal of Pharmaceutics, 63:135–144 (leuprolide acetate); Braquet et al., 1989, Journal of Cardiovascular Pharmacology, 13(suppl. 5):143–146 (endothelin-1); Hubbard et al., 1989, Annals of Internal Medicine, Vol. III, pp. 206–212 (al-antitrypsin); Smith et al., 1989, J. Clin. Invest. 84:1145–1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482–3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Formulations suitable for use with a nebulizer, either jet or ultrasonic, will typically comprise polypeptide (or derivative) dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the polypeptide (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing polypeptide (or derivative) and may also include a bulking agent, such as lactose, sorbitol, sucrose, or mannitol in amounts which facilitate dispersal of the powder from the device, e.g., 50 to 90% by weight of the formulation. The protein (or derivative) should most advantageously be prepared in particulate form with an average particle size of less than 10 mm (or microns), most preferably 0.5 to 5 mm, for most effective delivery to the distal lung.

Nasal Delivery. Nasal or nasopharyngeal delivery of the polypeptide (or derivative) is also contemplated. Nasal delivery allows the passage of the polypeptide directly over the upper respiratory tract mucosal after administering the therapeutic product to the nose, without the necessity for deposition of the product in the lung. Formulations for nasal delivery include those with dextran or cyclodextran.

Experimental Details Section

EXAMPLE 1

Peptide Truncates of Choline Binding Protein A (CbpA)

A polypeptide comprising a truncated N-terminal fragment of the CbpA (serotype 4) was generated. Full length CbpA was amplified with PCR primers SJ533 and SJ537, the primers were designed based on the derived N-terminal amino acid sequence of the CbpA polypeptide. 5' forward primer SJ533=5' GGC GGA TCC ATG GA(A,G) AA(C,T) GA(A,G) GG 3' (SEQ ID NO:41). This degenerate primer designed from the amino acid sequence XENEG, incorporates both BamHI and NcoI restriction sites and an ATG start codon. 3' reverse primer SJ537=5' GCC GTC GAC TTA GTT TAC CCA TTC ACC ATT GGC 3' (SEQ ID NO:42). This primer incorporates a SalI restriction site for cloning purposes, and the natural stop codon from CbpA, and is based on both type 4 and R6×sequence.

PCR product was generated from genomic DNA as a template with primers SJ533 and SJ537 amplified 30 cycles with an annealing temperature of 50EC using High Fidelity™ enzyme (Boehringer Mannheim). The resulting PCR products were purified using QLAquick PCR Purification Kit™ (Qiagen, Inc.) then digested with BamHI and SalI restriction enzymes and cloned into the pQE30 expression vector (Qiagen, Inc.) digested with BamHI, XbaI, and SmaI restriction enzymes.

Polypeptide R2:

The naturally occuring PvuII site at the end of the second repeat region, namely the C region as shown in FIG. 1, (nucleic acid 1228 of Type 4 sequence) was exploited to create a truncated version of the cbpA gene, containing only the 5' portion of the gene. To create the truncate clone, the full length clone PM1580 (Type 4) or PM1581(R6x) was digested with PvuII and XbaI, the resulting fragment was ligated into the expression vector, PQE30 and transformed into the appropriate host. The protein was expressed and purified. In this instance the stop codon utilized by the expression vector is downstream of the insert, so the protein expressed is larger than the predicted size of the insert due to additional nucleic acids at the 5' end of the cloning site. The amino acid sequence of polypeptide R2 is set forth in SEQ ID NO 1.

Polypeptide R1:

A similar strategy was used to express only the first repeat region within the N-terminal region of CbpA, namely the A region of polypeptide R1. Here the naturally occuring XmnI site between the two amino repeats (nucleic acid 856 of the Type 4 sequence) was utilized. cbpA full length clone PM1580 was digested with XmnI and AatII. The vector pQE30 was digested with AatII and SmaI. Once again the two sized fragments were ligated, transformed into *E. coli* and clones screened for inserts. One positive clone was selected and recombinant protein purified from this stain.

All polypeptides were expressed and purified with the Qia Expression System™ (Qiagen) using an *E. coli* the pQE30 vector. The amino terminus of the His tagged proteins are detected by host and Western analysis using both anti-histidine antibodies and protein specific antibodies.

Purification of R1 and R2:

To induce production of and purify recombinant proteins from *E. coli* a single colony was selected from plated bacteria containing the recombinant plasmid and grown overnight at 37° in 6.0 mls LB buffer with 50 μg/ml kanamycin and 100 μg/ml ampicillin. This 6.0 ml culture was added to 1L LB with antibiotics at above concentrations. The culture was shaken at 37° C. until $A_{600}$=~0.400.1M IPTG was added to the 1L culture to a final concentration of 1 mM. The culture was then shaken at 37° C. for 3–4 hrs. The 1 L culture was spun for 15 min at 4000 rpm in a model J-6B centrifuge. The supernatant was discarded and the pellet stored at −20° C.

The 1L pellet was re-suspended in 25 ml 50 mM $NaH_2PO_4$, 10 mM Tris, 6M GuC1, 300 mM NaCl, pH 8.0 (Buffer A). This mixture was rotated at room temperature for 30 minutes and sonicated on a (VibraCell Sonicator (Sonics and Materials, Inc., Danbury, Conn.) using the micro tip, two times, for 30 secs, at 50% Cuty Cycle and with the output setting at 7. The mixture was spun 5 min at 10 K in a JA20 rotor and the supernatant removed and discarded. The supernatant was loaded onto a 10 ml Talon™ (Clonetech, Palo Alto, Calif.) resin column attached to a GradiFrac System™ (Pharmacia Biotech, Upsala, Sweden). The column was equilibrated with 100 ml Buffer A and washed with an additional 200 ml of this buffer. A volume based pH gradient using 100% 50 mM $NaH_2PO_4$, 8M Urea, 20 mM MES, pH6.0 (Buffer B) as the final target buffer was run over a total volume of 100 ml. Protein eluted at −30% Buffer B. Eluted peaks were collected and pooled.

For refolding, dialysis was carried out with a 2L volume of PBS at room temperature for approximately 3 hrs using dialysis tubing with a molecular weight cutoff of 14,000. The sample was then dialyzed overnight in 2L of PBS at 4° C. Additional buffer exchange was accomplished during the concentration of the protein using Centriprep-30 spin columns by adding PBS to the spun retenate and re-spinning. The protein concentration was determined using the BCA protein assay and the purity visualized using a Coomassie stained 4–20% SDS-PAGE gel (FIG. 3).

EXAMPLE 2

Lectin Activity of Polypeptides R1 and R2

LNnt is a carbohydrate analog of the receptors for pneumococci present on eukaryotic cells. It has been shown that a CbpA defective pneumococcal mutant failed to adhere to either eukaryotic cells or immobilized sugar indicating that CbpA is the adhesive ligand. CbpA is a modular protein that can be divided into two regions: the N-Terminal functional domain and the C-terminal choline binding domain (FIG. 1). Polypeptides R1 and R2 were analyzed for biological activity to determine if the activities of the entire CbpA were localized in the unique N terminus (modelled by R2) or a fragment thereof (modelled by R1). It was determined whether or not the N-terminal domain alone (R2) contained the lectin binding biological activity in the absence of the choline binding domain (CBD). This was tested using the full length CbpA and polypeptide R2 (truncate missing the CBD region beyond the Pvu II site in the proline rich region).

The assay was to coat tissue culture wells with glycoconjugates known to be recognized by CbpA: LNnT-albumin, 3' sialyl lactose-albumin, and the negative control albumin. The plates were then blocked with the albumin, washed and either full length CbpA Polypeptide R2, or polypeptide R1 were added for 15 minutes (0.8 µg/ml), then, without washing, fluoresein labelled R6 pneumococci were added for 30 minutes, washed and adherent bacteria counted visually.

Binding of R6 to carbohydrate without any peptide addition was the positive control and was calibrated at 100% (Table 1). In three separate experiments, CbpA full length or Polypeptide R2 competitively inhibited binding of pneumococci to LNnT coated surfaces. CbpA full length inhibited to 71, 64% and 63% of control: polypeptide R2 inhibited to 65%, 53% and 74% of control. The equivalent activity of CbpA and R2 indicates the choline binding domain is not necessary for LNnT lectin activity of CbpA, and that R2 is a candidate LNnT lectin.

In contrast to binding to LNnT, binding of pneumococci to 3' sialyl lactose was not inhibited by R2 (79 and 101%) compared to the full length CbpA (74 and 66%). This indicates that the sialic acid recognition activity is lost when the CBD is missing. In contrast R1 seems to be active in recognition of sialic acid, a property shared with CbpA but apparently masked in R2. This indicates that folding of polypeptide into functional domains is influenced by the composition and length of the polypeptide. Slight sequence variation is found in other strains (see FIG. 2). Given the high degree of homology of sequence between R1 and R2, it is further possible that both R1 and R2 are needed for lectin activity or that they are both lectin with slightly different specificities (±sialic acid).

TABLE 1

Inhibition of Binding of R6 pneumococci to purified glycoconjugate by soluble forms of CbpA

| | LNnT | | 3' sialyl lactose | |
|---|---|---|---|---|
| Cbp form | # pneumococci per monolayer (SD) | % control | # pneumococci per monolayer | % control per well |
| No peptide | 3282<br>2421 (489)<br>2210 (350) | 100% | 2611<br>2115 (125) | 100% |
| Full length CbpA | 2075<br>1740 (167)<br>1415 (50) | 63, 71, 64 | 1933<br>1405 (240) | 74<br>66 |
| Polypeptide R2 | 2461<br>1288 (672)<br>1440 (530) | 74, 53, 65 | 2639<br>1670 (420) | 101<br>79 |
| Polypeptide R1 | 3002<br>2245 (182)<br>2500 (310) | 91, 92, 112 | 1052<br>1445 (526) | 40<br>68 |

N = 3 experiments LNnt each 3 wells
N = 2 experiments SiL each 3 wells

Lectin Activity Correlates with Cell Binding Activity

Human cells bear surface molecules that contain carbohydrates (glycoprotein, and glycolipid) and bacteria bind to these glycoconjugates by the carbohydrate despite very different protein or lipid backbones. Thus, bacteria bearing polypeptide with lectin activity in vitro can adhere to human cell surfaces. This direct correlation between in vitro lectin activity and cell binding action is known for pneumococci. For example, LNnT competitively inhibits binding of pneumococci to TNF activated A549 human lung cells and blocks the progression of pneumonia in vivo. To establish that the lectin activity of truncates of CbpA reflects cell binding activity, CbpA and truncates were tested for inhibition of binding of pneumococci to lung cells (Table 2). Full length CbpA and polypeptide R2 competitively inhibited adherence of pneumococci to lung ells to 58% and 63% of controls respectively. Polypeptide R1 was not effective, indicating the LNnt binding activity of R2 is needed for and explains pneumococcal binding to lung cells.

TABLE 2

Binding of R6 pneumococci to TNF activated human lung cells

| | A549 Lung | |
|---|---|---|
| Cbp form | # pneumococci per monolayer (mean) | % control |
| No peptide | 697,704,674<br>702,722<br>(700) | 100% |
| Full length CbpA | 376,431<br>(403) | 58% |
| Polypeptide R2 | 517,693<br>314,342,350<br>(443) | 63% |
| Polypeptide R1 | 696,642,552<br>(630) | 90% |

N = 2 experiments of 2 or 3 wells each

LNnT Lectin Activity is Dependent on R2

The N-terminal region of CbpA contains two repeats of ~110 amino acids each (see FIG. 1, regions A and C within polypeptide R2). To study the relative contribution of the two domains to bio-activity R1, containing only domain A was compared to R2 and full length CbpA. When tested in the adherence assay, polypeptide R1 did not inhibit adherence to LNnT at all (91, 92, and 112% of wild type).

However, polypeptide R1 demonstrated some inhibition of binding to Sialyl lactose (68 and 40% of control). This demonstrates that the polypeptide R2 is required for LNnT lectin activity and R2 is a candidate LNnT lectin domain. In contrast R1 seems to be active in recognition of sialic acid.

Antibodies to N-terminal Domain of CbpA Block Cell Binding:

Given that the N-terminal domain of CbpA binds cells, interference with the N-terminal domain activity will prevent or reverse bacterial binding to cells or purified glycoconjugates. One such mechanism of interference is antibody.

TABLE 3

Inhibition of binding of R6 pneumococci to LNnT coated surfaces by anti-CbpA R2 antibodies

| | # pneumococci per monolayer (SD) | % control (mean) |
|---|---|---|
| PreImmune Antibody | 198 (64); 88 (4) | 100% |
| Antibody to Truncate R2 | 56 (11); 9 (2) | 28%; 10% |

5 μl of rabbit antibody undiluted + 5 μl 2 × $10^7$ R6x Preincubate, 6 at RT × 30 min, then add to LNnT coated wells for adherence assay. Two independent experiments are shown.

Figure 5:
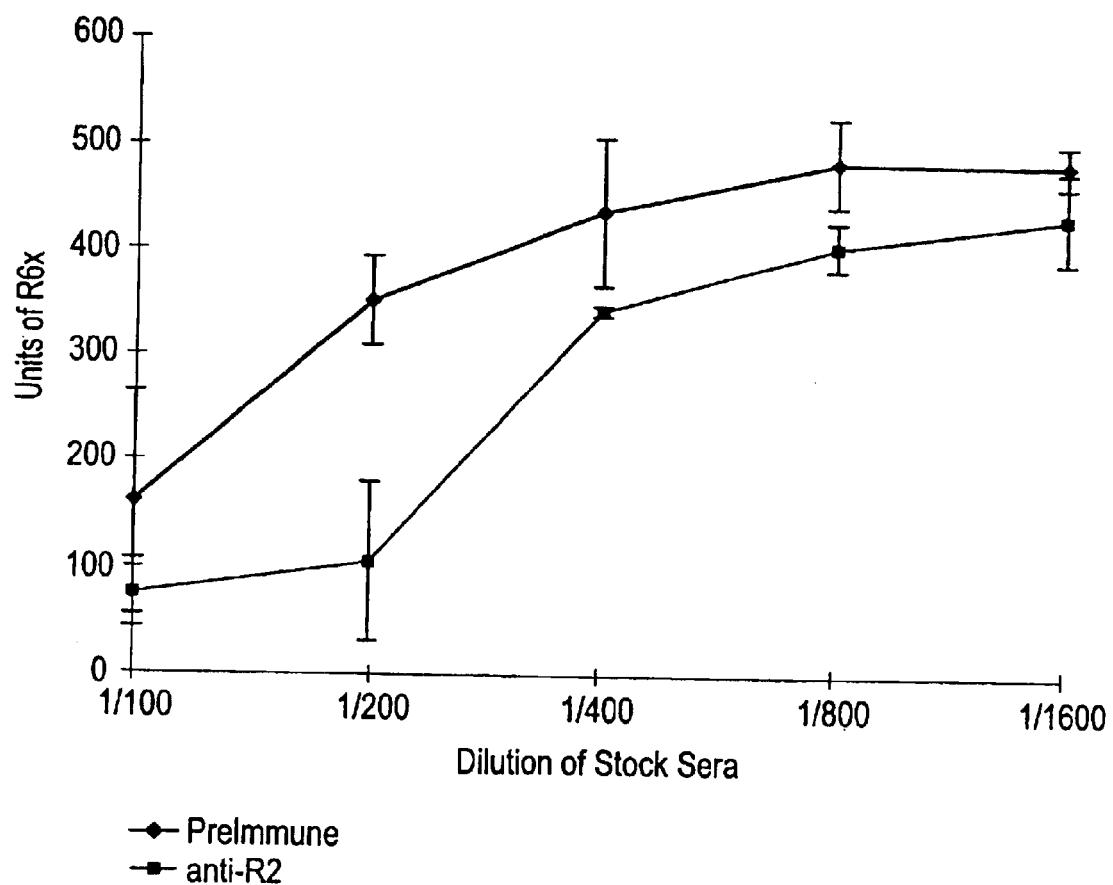
FIG. 5. Titration of anti-R2 antibody on R6x adhering to LNnT-HSA coated plates.
Figure 6:
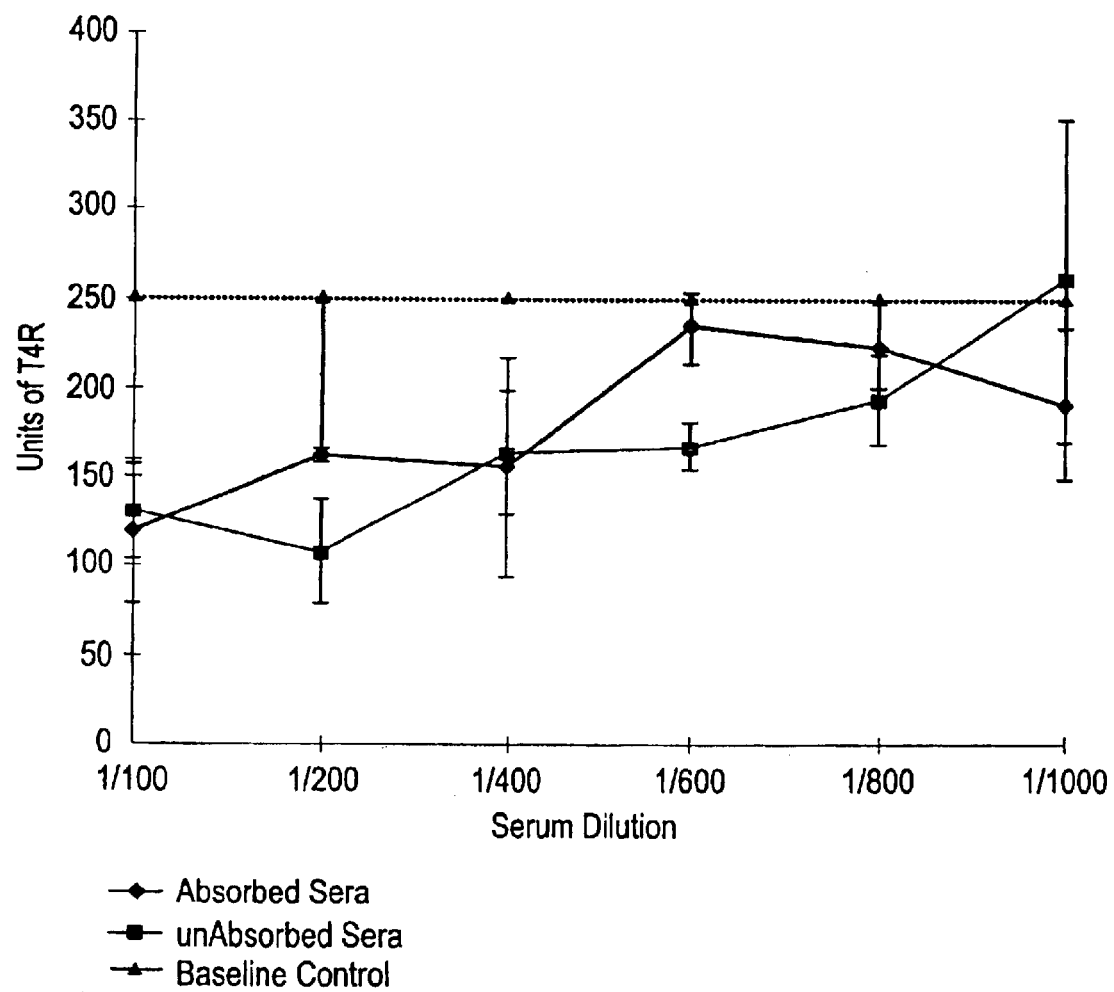
FIG. 6. Titration of anti-Cbp-A and absorbed anti-CbpA antibodies for activity blocking pneumococcal adherence to LNnT-HSA coated plates.

Antisera raised to the recombinant N-terminal domain of CbpA (R2) was tested for the ability to block adherence of pneumococci to LNnT. Rabbit polyclonal anti CbpA antisera (51 μl) plus 5 μl of 2×$10^7$ of labeled bacteria were incubated at room temperature for 30 min. This mixture was overlaid onto immobilized LNnT for 30 min., and then washed 3 times with PBS to remove unbound bacteria. Bacteria bound to the plates were enumerated microscopically and results are presented as the mean values plus the standard deviation from six wells. Results shown in Table 3 demonstrate that antisera raised against the R2 polypeptide blocked the binding of pneumococci to LNnT. FIG. 5 demonstrates a titration curve of preImmune versus anti-CbpA R2 antibody for inhibition of binding of pneumococci R6x to the model receptor LNnT. Greater than 70% of pneumococcal adherence was blocked by anti-R2 at dilutions of 1:100 and 1:200. Further dilution to 1:400 eliminated activity indicating the specificity of the effect.

The CbpA used to prepare the antisera shown in Table 3 and FIG. 5 was raised against CbpA from serotype 4. The R6xstrain pneumococci used in the inhibition of adherence assay was derived from serotype 2. The ability of the antibody to block adherence of a heterologous serotype of bacteria indicates cross protective activity across serotypes. Such activity is highly desired for an effective vaccine immunogen.

Activity of Antibodies to Native Conformation of N Terminus of CbpA:

CbpA can be purified over a choline affinity column from its natural host, the *pneumococcus*. Alternatively, a polyhistidine tag can be engineered onto the end of the gene such that the transcribed protein is extended by several histidine residues. These residues facilitate purification over a nickel affinity matrix Purification of full length polypeptides as opposed to shorter truncates favors retention of the native tertiary structure. CbpA purified especially from *pneumococcus* but also from *E. coli* or other host bacteria by these biochemical means retains its native tertiary structure. Used as an immunogen, natively folded CbpA engenders antibodies that potentially differ from those elicited by immunization with the truncate which may fold differently. Similarly, CbpA used as a therapeutic may have tertiary structure differing from the truncate which would improve its ability to block adherence. Given these considerations, it may be advantageous to produce CbpA as full length protein allowing it to fold to its native tertiary structure and then cleave the C terminal (CBD) away biochemically. For example, treatment with hydroxylamine will cleave CbpA at amino acid position 475 of serotype R6x and of serotype 4 of choline binding protein A, separating the N and C termini. The N terminal fragment is then suitable as a therapeutic or an immunogen.

Alternatively, native CbpA can be used as an immunogen and antisera to the active structure. The bioactive anti-N terminal antibodies in this mixture can be enriched by removing antibodies to the BD by absorption. Such an antibody was prepared by incubating 200, ul serum with 1×$10^8$ CbpA defective-bacteria for 1 hour at R1. The other choline binding proteins on this mutant absorb out anti-CBD antibodies which are then removed from the antiserum by centrifuging and removing the bacteria.

To demonstrate the bioactivity of absorbed anti CbpA antibodies, the ability of the absorbed antiserum to block pneumococcal adherence to the model receptor LNnT was determined. R6x pneumococci were incubated with 1:600 dilution of antiserum and then added to wells coated with LNnT albumin.

TABLE 4

Absorbed anti CbpA antiserum blocks adherence

| Antisera (1:600) | Number of pneumococci per well ± SD | (% of control) |
|---|---|---|
| No antibody | 563 ± 11 | (100%) |
| PreImmune antiserum | 479 ± 11 | (85%) |
| Anti CbpA antiserum | 294 ± 72 | (52%) |
| Anti CbpA antiserum absorbed to remove CBD antibodies | 175 ± 38 | (31%) |

These results indicate that antibodies to the N terminal domain of Cbp/A in its native conformation strongly block adherence. This activity is greater than that to the truncate of FIG. 5 which was inactive at 1:600 dilution. Further demonstration of this activity of absorbed anti CbpA antiserum is shown by the titration study of FIG. 5. Baseline adherence of pneumococci Type 4 to LNnT coated wells is shown by the triangles. Pre-incubation of pneumoccoci with unabsorbed (squares) or absorbed (diamonds) antiserum at the various dilutions indicated yielded decreased adherence. The fact that both antisera showed similar decreases in adherence demonstrates that the majority of the blocking activity of antibody to CbpA resides in the N-terminus (i.e., removal of antibodies to the choline binding domain by absorption does not decrease bioactivity.

EXAMPLE 3

Passive Protection With Anti-R2 Antiserum

Generation of Rabbit Immune Sera:

Rabbit immune sera against polypeptide R2 (CbpA truncate) and CbpA were generated at Covance (Denver, Pa.). Following collection of pre-immune serum, a New Zealand white rabbit was immunized with 250 μg R2 containing both amino terminal repeats (preparation 483:58 above), in Complete Freund's Adjuvant. The rabbit was given a boost of 125 μg R2 in Incomplete Freund's Adjuvant on day 21 and bled on day 31. A second rabbit was similarly immunized with purified CbpA.

Figure 4:
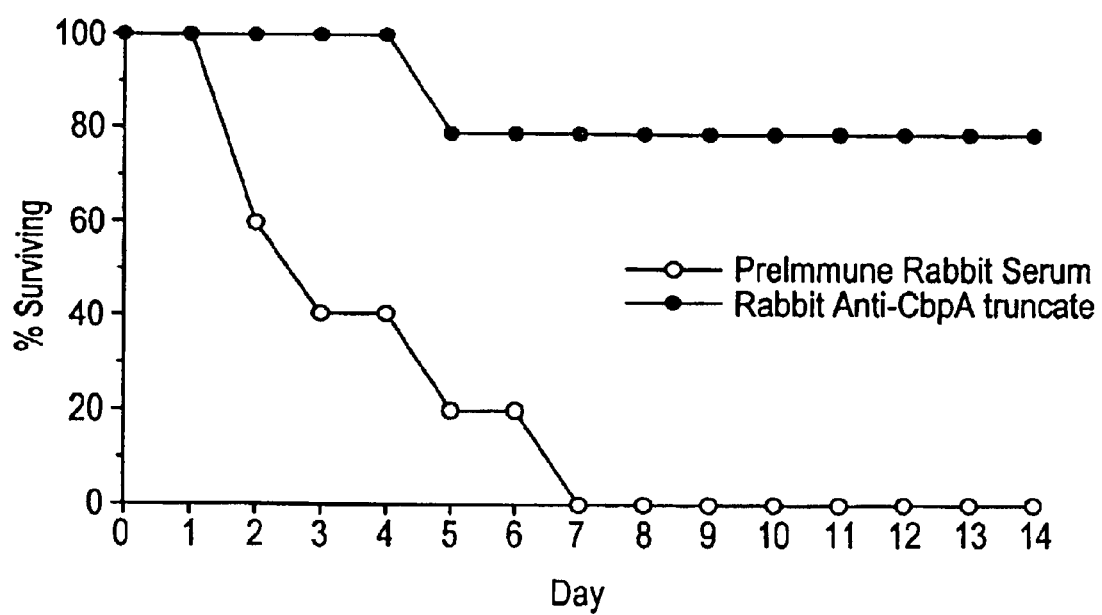
FIG. 4. Results of passive protection in mice. Immune sera against recombinant R2 protected mice from lethal *S. pneumoniae* challenge.

Passive Protection in Mice:

$C_3H/HeJ$ mice (5/group) were passively immunized intraperitoneally by with 100 μl of a 1:2 dilution of rabbit anti R2 or preimmune sera in sterile PBS (pre-immune and day 31 immune sera). One hour after administration of serum, mice were challenged with 1600 CFU *Streptococcus pneumoniae* serotype 6B (strain SP317). Mice were monitored for 14 days for survival. Eighty percent of the mice immunized with rabbit immune serum raised against polypeptide R2 survived challenge (FIG. 4). All mice immunized with pre-immune rabbit serum were dead by day 7.

This data demonstrates that antibodies specific for CbpA are protective against systemic pneumococcal infection. The data further indicate that the choline-binding region is not necessary for protection, as antibody specific for the truncated protein polypeptide R2, lacking the conserved choline binding repeats, was sufficient for protection. In addition, serum directed to CbpA of serotype 4 was protective against challenge with serotype 6B.

EXAMPLE 4

Active Protection With Anti-R1 Antiserum

C3H/HeJ mice (10/group) were immunized intraperitoneally with CbpA truncate protein R1 (15 µg in 50 µl PBS, plus 50 µl Complete Freund's Adjuvant). A group of 10 sham immunized mice received PBS and adjuvant. A second immunization was administered four weeks later, 15 µg protein i.p. with Incomplete Freund's Adjuvant (sham received PBS plus IFA). Blood was drawn (retro-orbital bleed) at weeks 3, 6, and 9 for analysis of immune response. The ELISA end point anti-CbpA truncate titer of pooled sera from the 10 CbpA immunized mice at 9 weeks was 4,096,000. No antibody was detected in sera from sham immunized mice. Mice were challenged at week 10 with 560 CFU *Streptococcus pneumoniae* serotype 6B (strain SPSJ2p, provided by P. Flynn, St. Jude Children's Research Hospital, Memphis, Tenn.). Mice were monitored for 14 days for survival. Eighty percent of the mice immunized with CbpA truncate protein R1 survived challenge. All sham immunized mice were dead by day 8 (FIG. 7).

This data demonstrates that immunization with a recombinant fragment of CbpA elicits production of specific antibodies capable of protecting against systemic pneumococcal infection and death. The data further indicates that the choline-binding region is not necessary for protection, as the immunogen is the truncated protein R1. Additionally, the results suggest that a single amino terminal repeat may be sufficient to elicit a protective response. Cross protection is also demonstrated as the recombinant pneumococcal protein was generated based on serotype 4 DNA sequence and protection was observed following challenge with a serotype 6β late.

EXAMPLE 5

Prophylaxis Against Nasopharyngeal Colonization in the Infant Rat

In vitro the N terminal domain of CbpA competitively inhibited pneumococcal attachment. To demonstrate the therapeutic utility of peptides with this activity, infant rats were administered truncate peptides, then challenged with pneumococci and colonization of the nasopharynx was evaluated.

Rats were treated intranasally with 10 µl of PBS containing 0.8 µg of polypeptide R2 or R1 or no protein. 15 min later Type 3 pneumococci (Strain SIII) (10 µl containing $1 \times 10^5$ cfer) were introduced intranasally. To determine the ability of the polypeptide to competitively inhibit pneumococcal adherence and colonization, nasal washing was performed at 72 hours and the number of pneumococci recovered was quantitated in each of 4 animals per group. Rats receiving SIII alone displayed 2200, 6500, 6900 and 8700 (mean 6075) colonies per 10 µl. Animals treated with truncate R2 showed the greatest decrease (3600, 3500, 2500, 2100) to mean 2925 bacteria 10 µl (48% of control). Animals treated with truncate R1 also showed decreased colonization (5000, 4800, 3500, 1600) to mean 3725 (61% of control).

This experiment demonstrates that administration of the peptide of the instant invention to animals in a therapeutic study design to animals can protect against subsequent pneumococcal challenge.

Discussion:

As demonstrated by the experiments, polypeptide R2 when: 1) administered as a vaccine antigen elicits protective antibodies and is a preferred composition for a vaccine formulation; and 2) delivered as a peptide to the respiratory tract and/or nasopharynx receptor, competitively prevents pneumococcal attachment and is a preferred composition for a prophylactic and therapeutic agent against colonization or invasive disease. Also, truncates of CbpA function as lectins without the CBD. Two carbohydrates are recognized: LNnT by a peptide containing both N-terminal repeats (A and C) in FIG. 1 and sialic acid by a peptide containing only the single most N-terminal repeat (A). The truncate containing the N-terminal repeat polypeptide R1 and R2 demonstrates lectin activity in cell culture assays as well.

Important features of polypeptide R2 activity include: 1) complete correlation of bioactivity of polypeptide R2 and full length CbpA for recognition of purified glycoconjugate receptor analogs, lung cells and animal models. Correlation is also demonstrated for antibodies to them; and 2) cross protection between type 4 derived agents and bacteria in in vitro assays using other serotype (e.g. 6B and 2) which is important for useful vaccine, prophylactic and therapeutic modalities.

---

What is claimed is:

1. An isolated polypeptide comprising an amino acid sequence as set forth in SEQ ID NO:5, wherein said polypeptide does not bind to choline.

2. The isolated polypeptide of claim 1, wherein said polypeptide comprises SEQ ID NO:3.

3. The isolated polypeptide of claim 1, wherein said polypeptide comprises SEQ ID NO:1.

4. The isolated polypeptide of claim 1, wherein said polypeptide comprises SEQ ID NO:24.

5. The isolated polypeptide of claim 1, wherein said polypeptide is immunogenic.

6. The isolated polypeptide of claim 1, wherein said polypeptide comprises an amino acid sequence having up to 475 amino acids.

7. The isolated polypeptide of claim 6, wherein said polypeptide comprises an amino acid sequence having up to 460 amino acids.

8. A pharmaceutical composition comprising the polypeptide of claim 1 and a pharmaceutically acceptable carrier, or diluent.

9. An isolated polypeptide comprising an amino acid sequence as set forth in SEQ ID NO:4, wherein said polypeptide does not bind to choline.

10. The isolated polypeptide of claim 9, wherein said polypeptide comprises SEQ ID NO:22.

11. The isolated polypeptide of claim 9, wherein said polypeptide is immunogenic.

12. The isolated polypeptide of claim 9, wherein said polypeptide comprises an amino acid sequence having up to 475 amino acids.

13. The isolated polypeptide of claim 9, wherein said polypeptide comprises an amino acid sequence having up to 460 amino acids.

14. An isolated polypeptide comprising a fragment of the amino acid sequence of SEQ ID NO:24, wherein said fragment does not bind to choline, and comprises at least 138 consecutive amino acids of SEQ ID NO:24, wherein said polypeptide is immunogenic.

15. An isolated polypeptide comprising the amino acid sequence set forth in SEQ ID NO:5, wherein said amino acid sequence comprises at least one to 57 amino acid substitutions, wherein said polypeptide does not bind choline, is immunogenic and said polypeptide comprises up to 398 amino acids.

16. An isolated polypeptide comprising the amino acid sequence set forth in SEQ ID NO:3, wherein said amino acid sequence comprises at least one to 57 amino acid substitutions, and said polypeptide does not bind choline and wherein said polypeptide is immunogenic.

17. The isolated polypeptide of claim 16, wherein said polypeptide comprises the amino acid sequence set forth in SEQ ID NO:1, wherein said amino acid sequence comprises at least one to 57 amino acid substitutions, and said polypeptide does not bind choline and wherein said polypeptide is immunogenic.

18. The isolated polypeptide of claim 16, wherein said polypeptide comprises the amino acid sequence set forth in SEQ ID NO:24, wherein said amino acid sequence comprises at least one to 57 amino acid substitutions, and said polypeptide does not bind choline and wherein said polypeptide is immunogenic.

19. The isolated polypeptide of claim 15, wherein said amino acid substitutions comprise conservative amino acid substitutions.

20. An isolated polypeptide comprising the amino acid sequence set forth in SEQ ID NO:4, wherein said amino acid sequence comprises at least one to 57 amino acid substitutions, wherein said polypeptide does not bind choline and wherein said polypeptide is immunogenic and said polypeptide comprises up to 398 amino acids.

21. The isolated polypeptide of claim 20, wherein said polypeptide comprises the amino acid sequence set forth in SEQ ID NO:22, wherein said amino acid sequence comprises at least one to 57 amino acid substitutions, and said polypeptide does not bind choline and wherein said polypeptide is immunogenic.

22. An isolated polypeptide comprising an amino acid sequence selected from the group consisting of:
   a) an analog of the amino acid sequence set forth in SEQ ID NO:5, wherein said polypeptide does not bind choline and is immunogenic;
   b) an analog of the amino acid sequence set forth in SEQ ID NO:4, wherein said polypeptide does not bind choline and is immunogenic;
   c) an analog of the amino acid sequence set forth in SEQ ID NO:11, wherein said polypeptide does not bind choline, is immunogenic, and comprise up to 328 amino acids;
   d) an analog of the amino acid sequence set forth in SEQ ID NO:9, wherein said polypeptide does not bind choline, is immunogenic, and comprises up to 376 amino acids; and,
   e) an analog of the amino acid sequence set forth in SEQ ID NO:10, wherein said polypeptide does not bind choline, is immunogenic and comprises up to 328 amino acids.

23. An isolated polypeptide comprising an amino acid sequence selected from the group consisting of:
   a) a derivative of the amino acid sequence set forth in SEQ ID NO:5, wherein said polypeptide does not bind choline and is immunogenic;
   b) a derivative of the amino acid sequence set forth in SEQ ID NO:4, wherein said polypeptide does not bind choline and is immunogenic;
   c) a derivative of the amino acid sequence set forth in SEQ ID NO:11, wherein said polypeptide does not bind choline, is immunogenic, and comprise up to 328 amino acids;
   d) a derivative of the amino acid sequence set forth in SEQ ID NO:9, wherein said polypeptide does not bind choline, is immunogenic, and comprises up to 376 amino acids; and,
   e) a derivative of the amino acid sequence set forth in SEQ ID NO:10, wherein said polypeptide does not bind choline, is immunogenic and comprises up to 328 amino acids.

24. An isolated polypeptide comprising an amino acid sequence selected from the group consisting of:
   a) the amino acid sequence set forth in SEQ ID NO:5 wherein said amino acid sequence comprises at least one to 57 amino acid substitutions and said polypeptide comprises up to 398 amino acids, does not bind choline and is immunogenic, wherein said polypeptide interacts with an antibody, said antibody is capable of interacting with a full-length CbpA polypeptide;
   b) the amino acid sequence set forth in SEQ ID NO:4 wherein said amino acid sequence comprises at least one to 57 amino acid substitutions and said polypeptide comprises up to 398 amino acids, does not bind choline and is immunogenic, wherein said polypeptide interacts with an antibody, said antibody is capable of interacting with a full-length CbpA polypeptide;
   c) the amino acid sequence set forth in SEQ ID NO:11 wherein said amino acid sequence comprises at least one to 57 amino acid substitutions and said polypeptide, does not bind choline and is immunogenic, and comprise up to 328 amino acids, wherein said polypeptide interacts with an antibody, said antibody is capable of interacting with a full-length CbpA polypeptide;
   d) the amino acid sequence set forth in SEQ ID NO:9 wherein said amino acid sequence comprises at least one to 57 amino acid substitutions and said polypeptide does not bind choline and is immunogenic, and comprises up to 376 amino acids, wherein said polypeptide interacts with an antibody, said antibody is capable of interacting with a full-length CbpA polypeptide;
   e) the amino acid sequence set forth in SEQ ID NO:10 wherein said amino acid sequence comprises at least one to 57 amino acid substitutions and said polypeptide does not bind choline, is immunogenic and comprises up to 147 amino acids, wherein said polypeptide interacts with an antibody, said antibody is capable of interacting with a full-length CbpA polypeptide; and,
   f) the amino acid sequence set forth in SEQ ID NO:3 wherein said amino acid sequence comprises at least one to 57 amino acid substitutions and said polypeptide, does not bind choline and is immunogenic, wherein said polypeptide interacts with an antibody, said antibody is capable of interacting with a full-length CbpA polypeptide.

25. An isolated polypeptide comprising an amino acid sequence selected from the group consisting of:
   a) the amino acid sequence set forth in SEQ ID NO:5, wherein said polypeptide does not bind choline, wherein said polypeptide interacts with an antibody, said antibody is capable of interacting with a full-length CbpA polypeptide;
   b) the amino acid sequence set forth in SEQ ID NO:4, wherein said polypeptide does not bind choline, wherein said polypeptide interacts with an antibody, said antibody is capable of interacting with a full-length CpbA polypeptide;
   c) the amino acid sequence set forth in SEQ ID NO:11, wherein said polypeptide does not bind choline, is immunogenic and comprise up to 328 amino acids, wherein said polypeptide interacts with an antibody, said antibody is capable of interacting with a full-length CbpA polypeptide;
   d) the amino acid sequence set forth in SEQ ID NO:9, wherein said polypeptide does not bind choline, is immunogenic and comprises up to 376 amino acids, wherein said polypeptide interacts with an antibody, said antibody is capable of interacting with the full-length CbpA polypeptide; and,
   e) the amino acid sequence set forth in SEQ ID NO:10, wherein said polypeptide does not bind choline, is immunogenic and comprises up to 328 amino acids, wherein said polypeptide interacts with an antibody, said antibody is capable of interacting with a full-length CbpA polypeptide.

26. An isolated polypeptide comprising an amino acid sequence as set forth in SEQ ID NO:11, wherein said polypeptide does not bind to choline and comprises up to 328 amino acids.

27. An isolated polypeptide comprising an amino acid sequence as set forth in SEQ ID NO:9, wherein said polypeptide does not bind to choline and comprises up to 376 amino acids.

28. The isolated polypeptide of claim 27, wherein said polypeptide comprises SEQ ID NO:7.

29. The isolated polypeptide of claim 26, wherein said polypeptide is immunogenic.

30. The isolated polypeptide of claim 27, wherein said polypeptide is immunogenic.

31. A pharmaceutical composition comprising the polypeptide of claim 26, and a pharmaceutically acceptable carrier, or diluent.

32. An isolated polypeptide comprising an amino acid sequence as set forth in SEQ ID NO:10, wherein said polypeptide does not bind to choline, and said polypeptide comprises up to 328 amino acids.

33. The isolated polypeptide of claim 32, wherein said polypeptide comprises SEQ ID NO:23.

34. The isolated polypeptide of claim 32, wherein said polypeptide is immunogenic.

35. An isolated polypeptide comprising an amino acid sequence set forth in SEQ ID NO:11, wherein said amino acid sequence comprises at least one to 57 amino acid substitutions, and said polypeptide does not bind choline, is immunogenic and comprises up to 328 amino acids.

36. The isolated polypeptide of claim 35, wherein said polypeptide comprises the amino acid sequence set forth in SEQ ID NO:9, wherein said amino acid sequence comprises at least one to 57 amino acid substitutions, and said polypeptide does not bind choline and is immunogenic.

37. The isolated polypeptide of claim 36, wherein said polypeptide comprises the amino acid sequence set forth in SEQ ID NO:7, wherein said amino acid sequence comprises at least one to 57 amino acid substitutions, and said polypeptide does not bind choline and is immunogenic.

38. The isolated polypeptide of claim 35, wherein said amino acid substitutions comprise conservative amino acid substitutions.

39. An isolated polypeptide comprising an amino acid sequence set forth in SEQ ID NO:10, wherein said amino acid sequence comprises at least one to 57 amino acid substitutions, and said polypeptide does not bind choline, is immunogenic and comprises up to 147 amino acids.

40. The isolated polypeptide of claim 39, wherein said polypeptide comprises the amino acid sequence set forth in SEQ ID NO:23, wherein said amino acid sequence comprises at least one to 57 amino acid substitutions, and said polypeptide does not bind choline and is immunogenic.

41. A pharmaceutical composition comprising the polypeptide of claim 27, and a pharmaceutically acceptable carrier, or diluent.

42. The isolated polypeptide of claim 16, wherein said amino acid substitutions comprise conservative amino acid substitutions.

43. The isolated polypeptide of claim 14, wherein said polypeptide has lectin activity.

44. The isolated polypeptide of claim 15, wherein said polypeptide has lectin activity.

45. The isolated polypeptide of claim 16, wherein said polypeptide has lectin activity.

46. The isolated polypeptide of claim 14, wherein said polypeptide has lectin activity.

47. The isolated polypeptide of claim 18, wherein said polypeptide has lectin activity.

48. The isolated polypeptide of claim 20, wherein said polypeptide has lectin activity.

49. The isolated polypeptide of claim 21, wherein said polypeptide has lectin activity.

50. The isolated polypeptide of claim 35, wherein said polypeptide has lectin activity.

51. The isolated polypeptide of claim 36, wherein said polypeptide has lectin activity.

52. The isolated polypeptide of claim 37, wherein said polypeptide has lectin activity.

53. The isolated polypeptide of claim 39, wherein said polypeptide has lectin activity.

54. The isolated polypeptide of claim 40, wherein said polypeptide has lectin activity.

* * * * *

UNITED STATES PATENT AND TRADEMARK OFFICE
CERTIFICATE OF CORRECTION

PATENT NO. : 6,858,706 B2
DATED : February 22, 2005
INVENTOR(S) : Tuomanen et al.

It is certified that error appears in the above-identified patent and that said Letters Patent is hereby corrected as shown below:

Title page,
Item [56], References Cited, FOREIGN PATENT DOCUMENTS, "WO 99/52166 10/1999" should read -- WO 99/51266 10/1999 --.

Column 107,
Lines 33 and 53, the second occurrence of "an" should read -- the --;

Column 109,
Lines 5, 26 and 46, the second occurrence of "an" should read -- the --;

Column 110,
Lines 26, 56 and 60, the second occurrence of "an" should read -- the --.

Column 111,
Lines 6, 14 and 32, the second occurrence of "an" should read -- the --.

Column 112,
Line 17, "claim 14" should read -- claim 17 --.

Signed and Sealed this

Tenth Day of May, 2005

JON W. DUDAS
*Director of the United States Patent and Trademark Office*